(12) United States Patent
Zimering et al.

(10) Patent No.: US 7,972,798 B2
(45) Date of Patent: Jul. 5, 2011

(54) METHOD FOR IDENTIFYING DIABETIC PATIENTS AT INCREASED RISK FOR PATHOLOGICAL COMPLICATIONS

(75) Inventors: Mark B. Zimering, Lyons, NJ (US); Zui Pan, Piscataway, NJ (US); Janet Alder, Piscataway, NJ (US); Smita Thakker-Varia, Piscataway, NJ (US)

(73) Assignee: The United States of America as represented by the Department of Veterans Affairs, Washington, DC (US)

( * ) Notice: Subject to any disclaimer, the term of this patent is extended or adjusted under 35 U.S.C. 154(b) by 342 days.

(21) Appl. No.: 12/315,526

(22) Filed: Dec. 4, 2008

(65) Prior Publication Data

US 2009/0208511 A1   Aug. 20, 2009

Related U.S. Application Data

(60) Provisional application No. 61/005,515, filed on Dec. 4, 2007.

(51) Int. Cl.
*G01N 33/53* (2006.01)
*G01N 33/564* (2006.01)
*A61K 38/28* (2006.01)
*A61K 31/192* (2006.01)

(52) U.S. Cl. ............ 435/7.1; 435/7.5; 514/5.9; 514/576

(58) Field of Classification Search ........................ None
See application file for complete search history.

(56) References Cited

OTHER PUBLICATIONS

Antibodies to endothelial cells. Lancet. Mar 16, 1991;337(8742):649-50.*
Fillit et al. Association of autoimmunity to vascular heparan sulfate proteoglycan and vascular disease in the aged. Gerontology. 1993;39(4)177-82.*
Jones et al. Vascular endothelial cell antibodies in diabetic patients. Association with diabetic retinopathy. Diabetes Care. Apr. 1992;15(4):552-5.*
Petty et al. Diabetes is associated with a high incidence of endothelial-binding antibodies which do not correlate with retinopathy, von Willebrand factor, angiotensin-converting enzyme or C-reactive protein. Diabetes Res. Jul. 1991;17(3):115-23.*
Powers, A.C. "Diabetes Mellitus", Chapter 323 in, Harrison's principles of internal medicine, 16th ed., editors, Dennis L. Kasper et al., New York : McGraw-Hill, c2005, pp. 2152, 2161.*

* cited by examiner

*Primary Examiner* — David S Romeo
(74) *Attorney, Agent, or Firm* — Adriano & Associates

(57) ABSTRACT

The present invention provides methods for detecting and measuring, in a sample from a subject, the plasma levels of endothelial cell antibodies to diagnose an increased risk of pathological complications, such as visual impairment, associated with diabetes.

11 Claims, 29 Drawing Sheets

A)

B)

C)

A

B

C

A.  1:25 dilution of Pt 1

B.  1:100 dilution of Pt 1

1:200 dilution of Pt 1

C.

A.

B.

A.

B.

Figure 14
Figure 14a
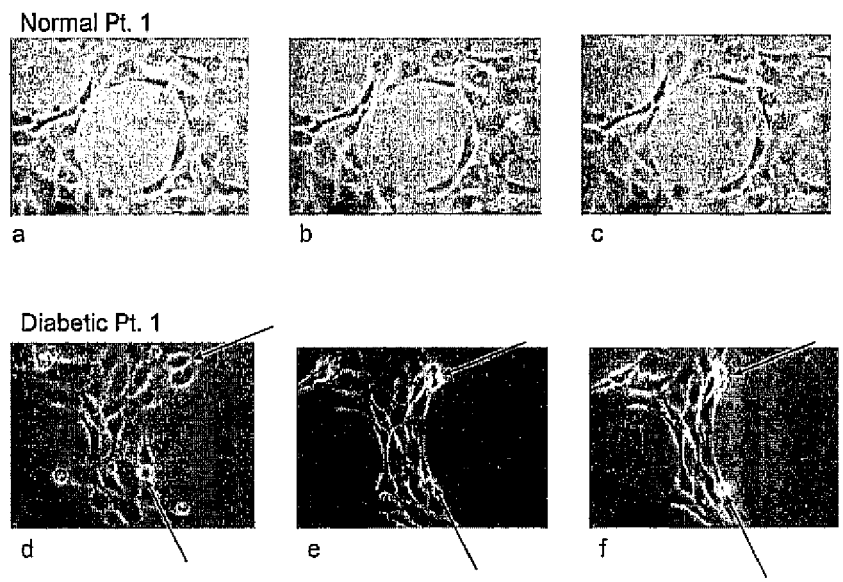
Figure 14b
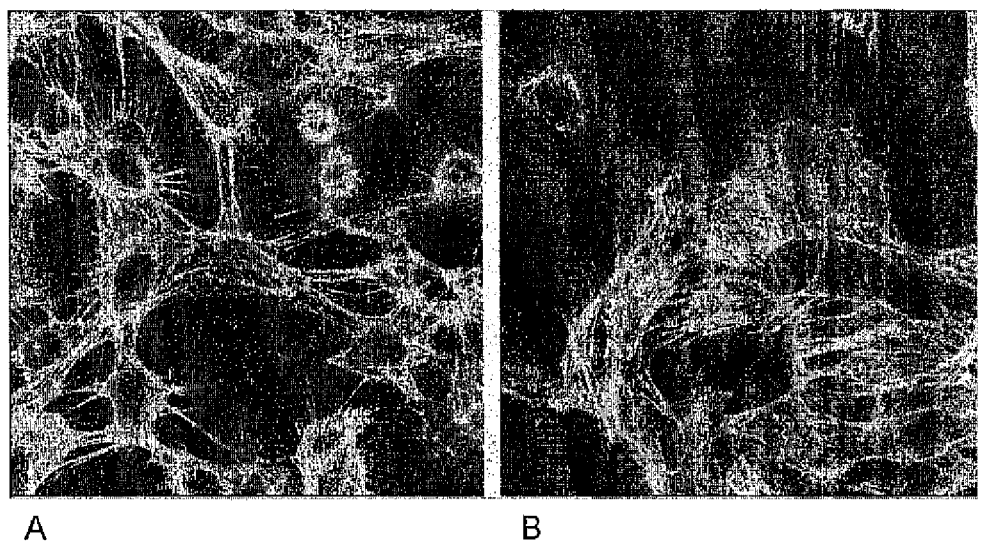

Fig 21. Comparison of antibody level effect on occurrence of laser events

METHOD FOR IDENTIFYING DIABETIC PATIENTS AT INCREASED RISK FOR PATHOLOGICAL COMPLICATIONS

This application claims the priority of U.S. Provisional Patent Application Ser. No. 61/005,515, filed Dec. 4, 2007, the contents of which are hereby incorporated by reference in their entirety.

Throughout this application various publications are referenced. The disclosures of these publications in their entireties are hereby incorporated by reference into this application in order to more fully describe the state of the art to which this invention pertains.

FIELD OF THE INVENTION

The present invention relates to methods for testing blood samples by measuring plasma levels of endothelial cell antibodies (e.g., autoantibodies). In particular, the invention relates to methods for diagnosing or monitoring pathological complications of diabetes, such as visual impairment or neuropathy, in a subject, by measuring the plasma levels of endothelial cell antibodies (e.g., autoantibodies).

BACKGROUND OF THE INVENTION

Diabetic patients often suffer a variety of pathological complications such as visual impairment and neuropathy. Neuropathy can be disabling because of unremitting pain.

Diabetic retinopathy is one of the leading causes of new cases of adult blindness in the United States. Approximately 15 million people in the United States suffer with type 2 diabetes, and the prevalence of this disease, especially in the young obese, is increasing dramatically. Population-based epidemiological studies indicate that macular edema, the leakage of plasma proteins from capillaries onto the retina, is the most common form of vision threatening retinopathy in type 2 diabetes. Macular edema is under-recognized and can only be diagnosed through an examination by a trained eye care professional, optometrist or ophthalmologist. Leakage of protein from damaged retinal capillaries can cause progressive visual impairment and may be a precursor for a more serious vision-threatening form of diabetic retinopathy-proliferative retinopathy. Leakage from capillaries, diabetic macular edema, requiring therapeutic intervention with laser photocoagulation, is not easy to predict by any known method other than frequent opthalmologic examinations which may be costly, inconvenient, or even unavailable to patients residing in rural areas or a great distance from limited opthalmologic resources. The advent of a simple blood test which is predictive of an increased risk for diabetic macular edema, could help identify the high risk subset of diabetic patients needing more urgent referral to eye care professionals, for examination and treatments to prevent visual impairment.

A test for detecting endothelial cell autoantibodies has been previously described (Zimering, M B and Thakker-Varia, S. Increased fibroblast growth factor-like autoantibodies in serum from a subset of patients with cancer-associated hypercalcemia. Life Sciences, 71 (2002) 2939-2959).

Endothelial cell autoantibodies are highly prevalent in a wide range of autoimmune disorders, e.g. lupus, vasculitis. Our group published findings that endothelial cell inhibitory autoantibodies also occur in a subset of advanced cancer patients (Zimering, M B and Thakker-Varia, S. Increased fibroblast growth factor-like autoantibodies in serum from a subset of patients with cancer-associated hypercalcemia. Life Sciences, 71 (2002) 2939-2959).

Circulating autoantibodies which bind to endothelial cells have been recognized for some time in a number of autoimmune disorders. The occurrence of such antibodies has been implicated in a number of possible disease manifestations including proliferative diabetic retinopathy in type 1, autoimmune diabetes (Jones D B, Wallace R, Frier B M. Vascular cell antibodies in diabetic patients. Association with diabetic retinopathy. Diabetes Care. 1992, 15(4), p. 552-555). However, in the same small study of endothelial cell binding autoantibodies in type 2, adult-onset diabetes, the same authors found no correlation between such antibodies and retinopathy or the lack of diabetic retinopathy (23-26% of both kinds of patients had such circulating antibodies, Jones D B, Wallace R, Frier B M. Vascular cell antibodies in diabetic patients. Association with diabetic retinopathy. Diabetes Care. 1992, 15(4), p. 552-555). Two larger studies, the first involving 176 type 1 diabetic subjects (Wangel A G, Kontiainen S, Scheinin T, Schlenzka A, Wangel D, Mäenpää J. Anti-endothelial cell antibodies in insulin-dependent diabetes mellitus. Clin Exp Immunol 1992 88 (3) p. 410-413) and the second involving 777 diabetics (Petty R G, Pottinger B E, Greenwood R M, Pearson J D, Mahler R F. Diabetes is associated with a high incidence of endothelial-binding antibodies which do not correlate with retinopathy, von Willebrand factor, angiotensin-converting enzyme or C-reactive protein. Diabetes Res. 1991 July; 17(3):115-23) each found no correlation between endothelial antibodies retinopathy or other diabetic microvascular complications. For this reason, the possibility that endothelial cell autoantibodies might mediate diabetic macular edema in non-insulin dependent, non-autoimmune type 2 diabetes was not previously explored systemically, in any known published study.

In summary, previous published studies indicated a relationship between plasma endothelial cell binding antibodies and proliferative diabetic retinopathy in type 1, "auto-immune" diabetes (Jones et al., 1992, supra). No such relationship, however, was demonstrated for a more common form of retinal complication suffered by patients with type 2 diabetes, so-called macular edema. In fact, the data shown herein for type 2 diabetes differs from the conclusions reached by Jones et al., 1992 (supra) that endothelial cell binding autoantibodies do not correlate with retinopathy in type 2 diabetes.

The invention herein describes the novel application of detecting endothelial cell antibodies for the detection and monitoring of specific diabetic complications associated with diabetes, particularly visual impairment.

SUMMARY OF THE INVENTION

The present invention provides methods for measuring, in a sample from a diabetic subject, the levels of endothelial cell antibodies (e.g., autoantibodies) as an indication of increased risk for pathological complications.

In an embodiment, the invention provides a method for diagnosing an increased risk of visual impairment in patients (e.g., diabetic patients) having endothelial cell antibodies (in some embodiments also referred to as endothelial cell plasma antibodies), by contacting a sample taken from the patient with a detectable agent for detecting endothelial cell antibodies in the sample.

In another embodiment, the invention further provides a method for monitoring the course of any visual impairment associated with diabetes, which comprises quantitatively determining in a first sample from the subject, the presence of endothelial cell antibodies, then comparing the amount so determined with the amount present in a later, second sample from the subject, such samples being taken at different points in time, a difference in the amounts determined, being indicative of the course of the visual impairment: an increase in amount indicating progression of the impairment, and a decrease in the amount indicating regression of the impairment.

In another embodiment, the invention provides a method for diagnosing an increased risk of neuropathy in a diabetic patient having endothelial cell antibodies, by contacting a sample taken from, the patient with a labeled agent for detecting endothelial cell antibodies in the sample.

BRIEF DESCRIPTION OF THE DRAWINGS

FIG. 14A shows time lapse video-micrographs of images taken from quiescent endothelial cells exposed to similar concentration of protein from protein-A eluates of normal plasma (a-c 1.5 hrs duration) and a representative, diabetic patient 2, protein-A eluate (d-f 3 hrs duration), as described in Example 1, infra. Arrows indicate cells that have rounded up and are dying. FIG. 14B is a photograph showing immunostaining of endothelial cells exposed to 2 diabetic inhibitory protein-A eluates using a F-actin specific phalloidin-rhodamine antibody, as described in Example 1, infra.

DETAILED DESCRIPTION OF THE INVENTION

Definitions

Figure 1:
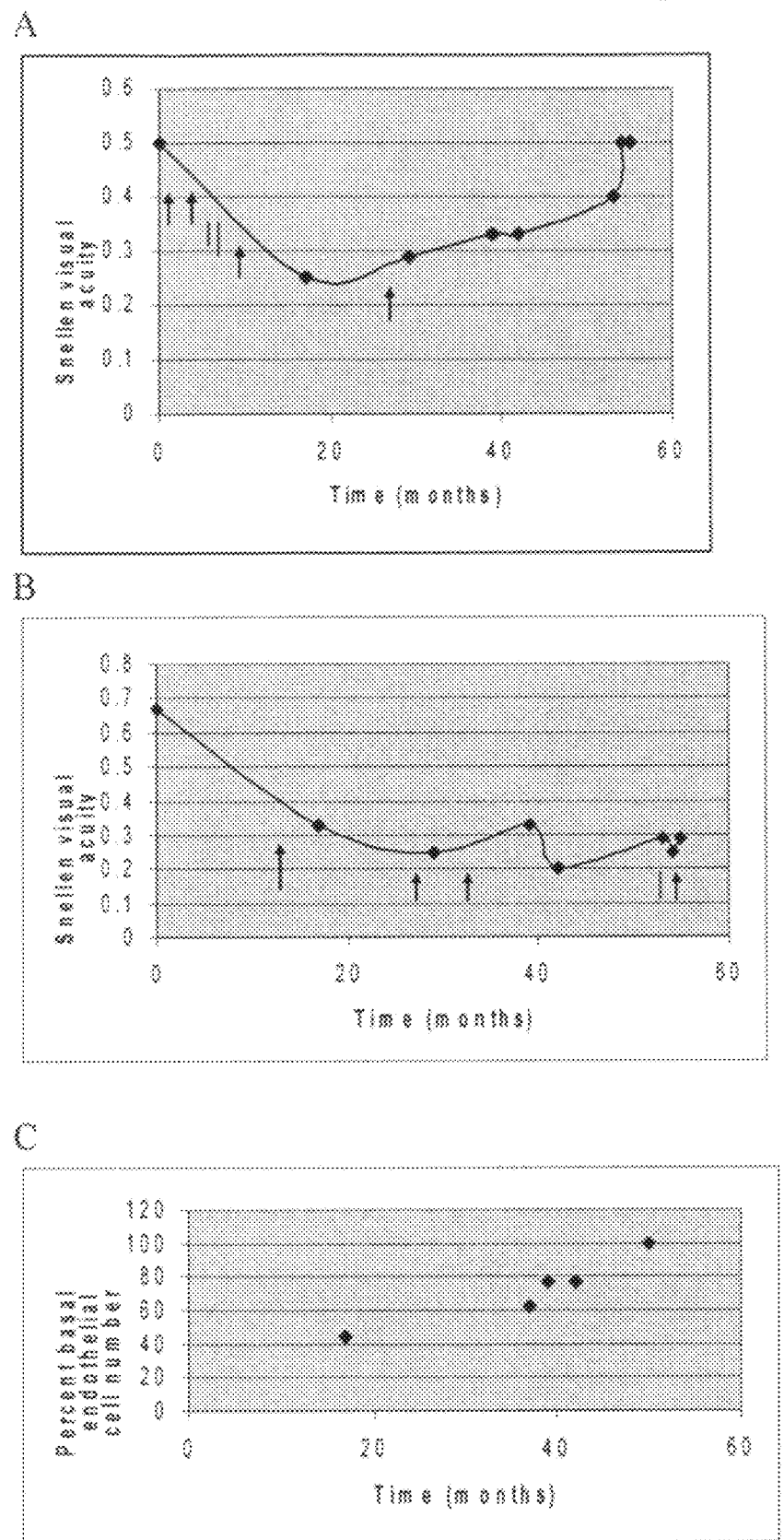
FIG. 1 shows three charts illustrating visual acuity changes in: A) left eye; B) right eye in patient 1: relation to occurrence of focal (arrows) or pan-retinal photocoagulation (vertical lines); and C) plasma inhibitory autoantibodies to endothelial cells, as described in Example 5, infra.

All scientific and technical terms used in this application have meanings commonly used in the art unless otherwise specified. As used in this application, the following words or phrases have the meanings specified.

As used herein, "endothelial cell antibodies" refers to anti-endothelial cell antibodies against cell surface receptors on endothelial cells, circulating in the cardiovascular system of a subject. Endothelial cell antibodies can be inhibitory. Endothelial cell antibodies include endothelial cell autoantibodies. In some embodiments, endothelial cell plasma antibodies are referred to as endothelial cell plasma antibodies.

As used herein, an "autoantibody" refers to an antibody generated by a living subject that reacts against a protein, cell, tissue or other component originating in the subject in whom it is formed.

As used herein, an "agent" refers to a compound capable of forming a complex with the endothelial cell antibodies (e.g., autoantibodies) in a sample. For example, the agent can be another antibody or protein A, and can be labeled for detection.

As used herein, an "impairment" means any pathology wherein antibodies (e.g. autoantibodies) against cell surface receptors on endothelial cells are elevated. Such impairment can result in the development of visual pathologies such as retinopathy (e.g., diabetic macular edema), cataracts and/or other complications of diabetes such as neuropathy.

As used herein, a "subject" or a "patient" (also referred to as "pt") is used interchangeably and refers to any mammal. For example a subject can be, but is not limited to, a human, mouse, rat, pig, monkey and ape, cow, sheep and horse.

As used herein, a "sample" refers to a biological sample from a subject. For example, the sample can be a fluid (e.g., urine, whole blood, serum or plasma, seminal, saliva, tears or other fluid), a cell or tissue from a subject.

As used herein, a "label" refers to an indicator that can be attached to an agent and detected. Examples of labels include, but are not limited to radiolabels, enzymes, chromophores and fluorescent compounds.

As used herein, "maculopathy" refers to any pathologic condition or disease of the macula, the small spot in the retina where vision is keenest. Also called macular retinopathy. This includes dry age-related macular degeneration (AMD) such as non-diabetic dry age-related macular degeneration, diabetic macular edema, and wet AMD, both symptomatic or asymptomatic.

In order that the invention herein described may be more fully understood, the following description is set forth.

Methods of the Invention

The present invention provides methods for measuring, in a sample from a subject, the plasma levels of endothelial cell antibodies (e.g., autoantibodies). In particular, the invention relates to methods for diagnosing or monitoring pathological complications in a subject, by measuring the levels (e.g., plasma levels) of endothelial cell antibodies in the subject. In one embodiment, the presence of a significant amount of endothelial cell antibodies is indicative of the presence of an increased risk of pathological complication in the subject (e.g., a diabetic patient).

As used herein, a significant amount of antibodies (e.g. autoantibodies) means an amount or number of antibodies that are present in a patient sample that causes at least about a 10% (or greater than 10%) decrease in endothelial cell number (or maintains less than about 90% of the endothelial cell number) in an endothelial cell assay (also referred to herein as endothelial cell proliferation assay) (Zimering, M B and Thakker-Varia, S. Increased fibroblast growth factor-like autoantibodies in serum from a subset of patients with cancer-associated hypercalcemia. Life Sciences. 71 (2002) 2939-2959). See for example Tables 1-4 of Example 11. Greater than 10% decrease in endothelial cell number includes 10-20% decrease, 20-30% decrease or 30-40% decrease in endothelial cell number or more. In some of the Examples, maintains less than about 90% of the endothelial cell number is expressed as inhibitory activity in the plasma fraction containing IgG, where inhibitory is defined as <=90%.

In an embodiment, the invention provides a method for diagnosing an increased risk of pathological complications in diabetic patients having endothelial cell antibodies (e.g., inhibitory endothelial cell antibodies) by contacting a sample (e.g., a biological fluid sample such as urine, blood serum or plasma) from the patient and detecting such antibodies present in the sample. The presence of a significant amount of endothelial cell antibodies in the sample may be indicative of the presence of an increased risk of pathological complication in diabetic patients.

The method for diagnosing an increased risk of pathological complications in diabetic patients may include the steps of: a) contacting the sample with an agent capable of forming a complex with the antibodies (e.g., inhibitory endothelial cell antibodies) in the sample; and b) determining whether any complex is formed by detecting the agent bound to antibodies.

The agent can be labeled so as to produce a detectable signal with a compound such as a radiolabel, an enzyme, a chromophore and a fluorescer.

In accordance with the practice of the invention, the agents include but are not limited to an antibody or portion thereof that binds to the Fc portion of an immunoglobulin (e.g., any of IgA, IgD, IgE, IgG, and/or IgM); *Staphylococcus Aureus* Protein A; *Staphylococcus Aureus* Protein G; *Staphylococcus Aureus* Protein L; *Staphylococcus Aureus* Protein G/L; and Fc receptor. The Fc receptor may be a soluble or recombinant Fc receptor. Examples of soluble or recombinant Fc receptor include but are not limited to a human Fc receptor Fc gamma RIIA molecule and human Fc receptor Fc gamma RIIb molecule.

Examples of suitable antibodies or portions thereof that bind to the Fc portion of an immunoglobulin include but are not limited to anti-IgE antibody (omalizaumab); anti-IgG1 antibody; anti-IgG2 antibody; anti-IgG3 antibody; and anti-IgG4 antibody.

The invention further provides a method for monitoring the course of a pathological complication, associated with diabetes, by quantitatively determining, in a first sample from the subject (for example, in a diabetic subject), the presence of antibodies (e.g., inhibitory endothelial cell autoantibodies), and then comparing the amount of antibodies so determined, with the amount present in a second, later sample from the subject, such samples being taken at different points in time, and a difference in the amounts of antibodies determined, being indicative of the course of the complication. For example, an increase in the amount of endothelial cell antibodies over time indicating progression of the pathological complication, and a decrease in the amount of endothelial cell antibodies over time indicating regression of the complication.

The method for monitoring the course of pathological complications associated with diabetes in a diabetic subject can have the following steps: a) detecting the presence of antibodies (e.g., inhibitory endothelial cell autoantibodies) in a sample, by contacting the sample with an agent that recognizes and binds such antibodies and detecting the binding of the agent to antibodies in the sample, thereby forming a complex, the complex being indicative of such antibodies in the sample, b) quantitatively determining the concentration of such antibodies so detected, and c) comparing the amount so determined with the amount present in a second sample from the subject, such samples being taken at different points in time, a difference in the amounts determined being indicative of the course of the pathological complication. For example, an increase in the amount of antibodies (e.g., inhibitory endothelial cell autoantibodies) in the sample at different points in time is indicative of progression of the pathological complication, a relatively poor prognosis.

The pathological conditions or complications diagnosed and/or monitored by the methods of the invention include, but are not limited to, a maculopathy, retinopathy, and diabetic neuropathy. The maculopathy may be a dry age-related macular degeneration, wet age-related macular degeneration, and/or macular edema (e.g., diabetic macular edema).

Advantages of the invention include the usefulness of the diagnostic or monitoring tests to alert the clinician to antibody-mediated causation in cases of pathological complications, which are otherwise difficult to diagnose and treat. This can lead to the early application of diagnostic and therapeutic options, which would not otherwise be employed, since the various impairments associated with the antibodies (e.g., autoantibodies) have previously been believed not to involve antibody mechanisms. For example, diabetic patients in whom elevated levels of antibodies (e.g., endothelial autoantibodies) are detected by the methods of the invention can be treated to remove an amount of such antibodies sufficient to reduce the complication's effects.

The following examples demonstrate the 1) key mechanisms activated in endothelial cells upon exposure to antibodies (e.g., autoantibodies), 2) the biochemical and physiochemical properties of the antibodies, 3) the likely cellular receptor that the antibodies target on cells, 4) the broad spectrum of antibody actions in several different kinds of cell types, 5) the correlation between antibody onset, potency, disappearance and their relation to the clinical severity of specific kinds of diabetic complications, including progressive visual impairment.

The examples also demonstrate that such antibodies (e.g., inhibitory endothelial cell autoantibodies) may contribute to the well known association between renal disease or diabetes and cataract development.

The invention herein shows that the methods of the invention for detecting the presence of inhibitory endothelial cell antibodies enable the determination of a risk of macular edema in a subset of adults with type 2 diabetes, and the need for urgent opthalmologic intervention.

In addition, a positive test for such antibodies (e.g., inhibitory endothelial cell autoantibodies) can indicate an increased risk for age-related macular degeneration and the need for opthalmologic evaluation in non-diabetic patients. Moreover, in some embodiment of the invention, the presence of such antibodies is a novel predictor of the risk for laser treatment in type 2 diabetes.

A positive test for inhibitory endothelial cell antibodies in an adult patient with diabetes, and persistent painful neuropathy associated with muscle weakness, may indicate the usefulness of immune-based therapy aimed at removing the circulating antibodies in treatment of a condition such as a neuropathy or other condition associated with diabetes.

The examples described below demonstrate the presence of potent inhibitory endothelial cell antibodies with increased affinity for heparin, in plasma from a subset of advanced diabetic subjects who suffer recurrent macular edema, and proteinuria. Around 30% of patients with diabetes for 11 yrs had evidence of such antibodies.

Type 2 diabetes is not an autoimmune disease. Thus the finding of potent inhibitory endothelial cell antibodies (which have pleiotrophic effects in cardiac and neuronal cells) is quite unexpected.

The invention provides methods for preventing or alleviating diabetic complications such as macular edema, retinopathy and cataracts in a subject. The method comprises determining whether the subject is at risk of pathological complications in diabetes by detecting inhibitory plasma antibodies (e.g., a significant amount of antibodies) directed against heparan sulfate proteoglycan components of endothelial cells in a sample from the subject; and then administering insulin and/or fibrate drugs to the subject at risk so as to thereby prevent or alleviate diabetic complications in the subject. In one embodiment, the method further comprises detecting low levels of plasma bFGF in the sample.

The invention further provides methods for inhibiting apoptosis in a subject. This is effected by preventing or alleviating diabetic complications by detecting inhibitory plasma antibodies (e.g., a significant amount of antibodies) directed against heparan sulfate proteoglycan components of endothelial cells in a sample from the subject; and then administering insulin and/or fibrate drugs to the subject at risk so as to thereby prevent or alleviate diabetic complications in the subject. In one embodiment, the method further comprises detecting low levels of plasma bFGF in the sample.

Examples of suitable fibrate drugs include but are not limited to clofibrate (also known as ethyl 2-(4-chlorophenoxy)-2-methylpropanoate), bezafibrate (also known as 2-[4-(2-{[(4-chlorophenyl)carbonyl]amino}ethyl)phenoxy]-2-methylpropanoic acid), aluminium clofibrate, gemfibrozil (also known as 5-(2,5-dimethylphenoxy)-2,2-dimethylpentanoic acid), fenofibrate (also known as 1-methylethyl2-[4-(4-chlorobenzoyl) phenoxy]-2-methyl-propanoate), simfibrate (also known as 3-[2-(4-chlorophenoxy)-2-methylpropanoyl]oxypropyl 2-(4-chlorophenoxy)-2-methylpropanoate), ronifibrate (also known as 3-[2-(4-chlorophenoxy)-2-methylpropanoyl]oxypropyl pyridine-3-carboxylate), ciprofibrate (also known as 2-[4-(2,2-dichlorocyclopropyl)phenoxy]-2-methylpropanoic acid), etofibrate (also known as 2-{[2-(4-chlorophenoxy)-2-methylpropanoyl]oxy}ethyl nicotinate), clofibride (also known as 4-(dimethylamino)-4-oxobutyl 2-(4-chlorophenoxy)-2-methylpropanoate), and clinofibrate (also known as 2-[4-[1-[4-(1-Hydroxy-2-methyl-1 oxobutan-2-yl)oxyphenyl]cyclohexyl]phenoxy]-2-methylbutanoic acid).

The invention also provides methods for diagnosing an increased risk of non-diabetes related AMD in a non-diabetic subject. The method comprises detecting inhibitory endothelial cell antibodies directed against heparan sulfate proteoglycan components of endothelial cells (e.g., a significant amount of antibodies) in a sample from the subject. In one embodiment, detecting the antibodies comprises contacting the sample from the subject with an agent capable of forming a detectable complex with the inhibitory endothelial cell antibodies in the sample; and then detecting whether any complex is formed.

Additionally, the invention provides methods for preventing or alleviating non-diabetes related AMD in a subject comprising determining whether a subject is at risk of pathological complications by detecting inhibitory endothelial cell antibodies directed against heparan sulfate proteoglycan components of endothelial cells (e.g., a significant amount of antibodies) in a sample from the subject; and administering an agent that recognizes and binds human vascular endothelial growth factor (VEGF) to the subject at risk and thereby preventing or alleviating non-diabetes related AMD in the subject. In one embodiment, the agent is an anti-VEGF antibody. The non-diabetes related AMD may be wet non-diabetes related AMD.

Further, the invention provides methods for diagnosing an increased risk of wet AMD in patients suffering from dry AMD. The method comprises detecting inhibitory plasma antibodies directed against heparan sulfate proteoglycan components of endothelial cells (e.g., a significant amount of antibodies) in a sample from the patient; and also detecting VEGF in the sample from the patient. The presence of VEGF and the antibodies (e.g., a significant amount of antibodies) being an indicator for an increased risk of wet AMD in the patients. In one embodiment, the step of detecting inhibitory plasma antibodies (e.g., a significant amount of antibodies) comprises contacting the sample from the patient with an agent capable of forming a detectable complex with the inhibitory endothelial cell antibodies in the sample; and detecting whether any complex is so formed; and the step of detecting VEGF comprises contacting the sample from the patient with an agent capable of forming a detectable complex with VEGF (e.g., an anti-VEGF antibody) in the sample; and detecting whether any complex is so formed.

The invention further provides methods of diagnostically evaluating a diabetic subject having inhibitory endothelial cell antibodies for an increased risk of pathological complications such as visual impairment, neuropathy, and maculopathy. The method comprises obtaining a sample from the subject; assaying the sample so obtained by determining the concentration of inhibitory plasma antibodies directed against heparan sulfate proteoglycan components of endothelial cells present; and comparing the results obtained from the assay with results obtained from an assay of one or more control samples. A higher concentration of inhibitory plasma antibodies in the sample than the concentration in said control sample or samples being indicative an increased risk of pathological complications such as visual impairment, neuropathy, and maculopathy. The control sample may be biological fluid from a nondiabetic patient.

The following examples are presented to illustrate the present invention and to assist one of ordinary skill in making and using the same. The examples are not intended in any way to otherwise limit the scope of the invention.

EXAMPLE 1

Plasma Endothelial Cell Inhibitory Autoantibodies Correlates to a Future Need for Opthalmologic Intervention The experiments herein determines whether autoantibodies may be present in biological fluid (e.g., plasma or serum) from advanced type 2 diabetes and whether such presence correlates with opthalmologic complications.

Protein-A Affinity Chromatography

To separate the IgG fraction from serum, 1-mL aliquots of serum were adjusted to pH 8.0 by adding 1 mL 100 mmol/L Tris (pH 8). The serum was clarified by centrifugation at 20,000×g for 30 min, and then 1 mL was applied to a 1-mL column of packed protein-A beads equilibrated in 100 mmol/L Tris, pH 8.0. The column was washed with 15 mL 100 mmol/L Tris, pH 8.0 (flow-through fraction), and then eluted stepwise with 5×1.0 mL 0.1 mol/L citric acid, pH 3.0. The pH of the eluate fractions was adjusted to 7.5-8.0 by adding 1 mol/L Tris (pH 8.0). The second and third eluate fractions contained nearly all of the protein A-eluted protein and were pooled and assayed for growth-promoting activity. The flow-through fraction was concentrated 3-fold before assay for growth-promoting activity. Eluate, flow-through and starting serum fractions were stored at ~4 degree C. Recovery of human IgG averaged 92% (data from Pierce Chemical Co., Rockford, Ill.) when 5 mg/mL human IgG was applied to a 1-mL protein-A column (n=10 experiments). Activity in protein-A eluate fractions was unchanged by overnight dialysis (Spectrapor; mol wt cut-off, 14 K) in 10 mmol/L Na phosphate, pH 7.4, compared to undialyzed samples. All fractions were sterile filtered (Millipore Corp., Bedford, Mass.; 0.22 um) before assay for growth-promoting activity (Zimering, M B and Thakker-Varia, S. Increased fibroblast growth factor-like autoantibodies in serum from a subset of patients with cancer-associated hypercalcemia. Life Sciences. 71 (2002) 2939-2959).

Conditioning on Anti-bFGF Antibody-protein A Affinity Column

To further purify the IgG fraction from serum, 0.5-mL aliquots of protein-A-eluted fractions from serum were adjusted to pH 7.5 by adding 1.5 mL of 10 mM Tris pH 7.5. The resulting 2-mL samples (approximately 1.25 mg/mL protein) were then applied to a column of protein A to which rabbit anti-bovine bFGF-(1-146) antibodies had been covalently attached via the $F_c$ region (Protein A IgG Orientation Kit, Pierce Chemical Co., Inc.). The column contained a substantial quantity of protein A not conjugated to antibovine bFGF antibodies since only 2-3 mg antibovine bFGF antibodies was available to react with 2 mL of protein A gel (capacity 11 mg IgG/mL protein A gel) in the presence of the imidate cross-linker, dimethylpimelimidate. The 2.0 mL column was washed with 10 mL mM Tris, pH-7.5, and eluted with 5×2.0 mL aliquots of IgG Elution Buffer pH 2.8 (Pierce Chemical Co., Inc). Ninety percent of the applied protein-A-eluted material bound and was eluted at low pH (2.8) from the columns. The pH of the eluate fractions was adjusted to 7.5-8.0 by adding 1 mol/L Tris (pH 8.0). The second and third eluate fractions contained nearly all of the eluted protein and were pooled and assayed for growth-promoting activity (as described in Methods, Protein A affinity chromatography). The column was regenerated between used by washing with 2-3 column volumes of IgG Elution Buffer pH 2.8 In one active breast cancer serum, use of the protein-A, antibFGF antibody-immunoaffinity column resulted in an approximately 3-fold increase in specific activity compared to specific activity in starting, protein-A-eluates.

Hydroxyapatite Chromatography

Hydroxylapatite (HA) is a form of calcium phosphate useful in purifying complex substances including antibodies. The mineral component in bone is made up of hydroxyapatite crystals. To further purify the IgG from serum, 0.5 mL aliquots of protein-A, antibovine bFGF antibody immunoaffinity eluate fractions were adjusted to pH 6.8 by adding 0.5 mL of 0.01 M sodium phosphate, pH 6.8 (binding buffer). The 1-mL samples (0.25-0.5 mg protein) were applied to 1-mL columns of hydroxyapatite (Bio-Gel HT, BioRad Labs, Hercules, Calif.) equilibrated in binding buffer. The columns were washed with 5 mL of binding buffer, and eluted stepwise with 1.5 mL fractions of 0.05, 0.1, 0.25 M sodium phosphate, pH 6.8 followed by a single 3.0 mL fraction of 0.4 M sodium phosphate, pH 6.8. Columns were regenerated between uses by washing with 2-3 column volumes of 0.4 M sodium phosphate. To avoid cross-contamination, several different columns were employed; and columns were discarded after several uses. Recovery of protein was >90%; less than 20% of starting protein generally appeared in the flow-through fractions. Eluate and flow-through fractions were sterile filtered before assay for growth-promoting activity.

Rabbit Polyclonal and Monoclonal Antibodies

Antiserum to synthetic bFGF-(1-24) was supplied by Dr. Andrew Baird (Whittier Institute, La Jolla, Calif.). The antiserum showed less than 1% cross-reactivity with up to 1 ug/mL each of platelet-derived growth factor, insulin-like growth factor-1, epidermal growth factor, or acidic FGF in a liquid phase RIA. The IgG fraction obtained after 3-fold concentration of the antiserum by ammonium sulfate precipitation and protein-A-affinity chromatography, anti-bFGF-(1-24), was stored at −70 C and used in the experiments described here. Anti-bFGF-(1-24) antibodies completely neutralized the growth-promoting activity of 10 ng/mL bFGF in bovine pulmonary endothelial cells.

Antiserum to recombinant bovine bFGF-(1-146) was developed in the laboratory of Dr. Henry G. Friesen, M. D. (Univ of Manitoba School of Medicine, Winnipeg, Manitoba, CANADA). The rabbit antiserum bound 20% of iodinated bovine bFGF at a final 1:2500 dilution. The antiserum showed less than 1% cross-reactivity with bovine acidic FGF or human interleukin-1, and the $ED_{50}$ values for displacement of radioligand were 8 and 440 ng/mL for bovine and human recombinant bFGF, respectively, in a liquid phase RIA. The IgG fraction obtained after protein-A affinity chromatography, anti-bFGF-(1-146), was stored at −70 C and used in the experiments described here.

Control purified human IgG (obtained from Pierce Chemical Co., Inc., Rockford, Ill.) was used as a standard in SDS-PAGE, in protein determinations, and to test for neutralization of bioactivity in highly purified bioactive fractions from serum. Goat or rabbit antihuman VEGF, and antihuman HGF antibodies (another control for bioactivity in purified protein-A-elute fractions from serum) were obtained from R&D Systems, Minneapolis, Minn. Mouse monoclonal antihuman FGF receptor antibodies were obtained from Upstate Biotechnology, Lake Placid, N.Y.

Chemicals

Recombinant human bFGF was from Austral Biologicals, Inc (San Ramona, Calif.). All other chemicals and reagents were analytical grade.

Protein Determinations

Protein concentrations were determined by a bicinchoninic acid protein Assay kit (Pierce Chemical Co., Rockford, Ill.).

Data Analysis

All data are the mean±1 SD. Comparisons were made by paired and unpaired Student's t tests.

Using plasma samples collected from patients enrolled in the Veterans Affairs Diabetes Trial (VADT) (Abraira C, Duckworth W, McCarren M, Emanuele N, Arca D, Reda D, Henderson W (2003). Design of the cooperative study of glycemic control and complications in diabetes mellitus type 2. *J Diab & Compl.* 17, 314-322) a test was performed of the correlation between plasma endothelial cell inhibitory autoantibodies and the occurrence of laser therapy for diabetic retinopathy (mostly macular edema). Plasma endothelial cell inhibitory autoantibodies were measured and the results were compared to clinical data on laser treatments which are stored in the computer at the Hines VA Cooperative Studies Coordinating Center. When the results were compared in 145 adult subjects with type 2 diabetes, mean age 61 yrs old, mean diabetes duration 11 yrs, a striking correlation was found between the presence of inhibitory autoantibodies and the future (up to 3 yr) risk for laser treatment: 24% of patient with antibodies required laser treatment during the follow up period, compared to 8% of patients without antibodies who required laser treatment, p=0.007 for the difference (Zimering M B, Anderson R J, Ge L, Moritz T, Pardun J and the VADT Substudy Group. 2008. Association between endothelial cell inhibitory autoantibodies and laser treatment for retinopathy in a baseline subset from the Veterans Affairs Diabetes Trial., Endocrine Society OR50-4, 163; and Zimering, M B and Thakker-Varia, S. Increased fibroblast growth factor-like autoantibodies in serum from a subset of patients with cancer-associated hypercalcemia. Life Sciences, 71 (2002) 2939-2959); incorporated by reference herein).

A significant inverse relationship between laser events for diabetic type 2 macular edema and plasma levels of the angiogenic growth factor basic fibroblast growth factor (bFGF) was found in diabetic patients (Zimering, M B, Luo, P, Moritz, T, Anderson, R. *Inverse correlation between plasma basic fibroblast growth factor and laser photocoagulation for retinopathy in a baseline subset of type 2 diabetes from the Veterans Affairs Diabetes Trial*, poster presented Jun. 5, 2007 at the 89th Annual Meeting of the Endocrine Society, Toronto, Canada).

Additional data indicated a similar unexpected inverse relationship between progression of retinopathy and plasma levels of VEGF in a different cohort of diabetic patients (Weiss A G, Chacko D M, Lane P H, Margalit E, Thompson A F, Mack-Shipman L R, Julie Stoner J A, Lane J T, Vascular endothelial growth factor, soluble vascular endothelial growth factor receptor-1, and progression of diabetic retinopathy in pregnant patients with type 1 diabetes. [P3-160] Endocrine Society, 2007). While not being bound by any theory, it is possible that autoantibodies which may in part bind to and interfere with the detection of either plasma bFGF or plasma VEGF (both are heparin-binding growth factors), may explain the unexpected inverse correlation between plasma levels of these two angiogenic factors and different forms of retinopathy.

EXAMPLE 2

Plasma bFGF Inversely Correlates to Baseline or Post-Baseline Laser Treatment

A relationship between increased plasma bFGF and laser treatment was screened for in 172 patients in an ongoing clinical study from the Veterans Affairs Diabetes Trial (VADT).

Baseline Characteristics

Baseline clinical characteristics are summarized in Table A (see below). Plasma bFGF-IR was determined at the baseline study visit. All subjects were >40 yrs old; 95% were men.

TABLE A

Baseline characteristics in 172 study subjects

|  | Mean ± SD |
|---|---|
| n | 172 |
| bFGF (pg/mL) | 6.6 ± 6.9 |
| Age (yrs) | 59.2 ± 8.4 |
| BMI (kg/m$^2$) | 31.4 ± 4.7 |
| Waist circumference (cm) | 110.1 ± 12.2 |
| Hip circumference (cm) | 110.2 ± 9.3 |
| Systolic BP (mmHg) | 130.2 ± 17.9 |
| Diastolic BP (mmHg) | 74.2 ± 10.8 |
| Diabetes Duration (yrs) | 11.4 ± 8.1 |
| Urine albumin/creatinine ratio (mg/g) | 151 ± 491 |
| HbA$_1$c (%) | 9.5 ± 1.4 |
| Triglyceride (mg/dL) | 205 ± 226 |
| Total cholesterol (mg/dL) | 181 ± 45 |
| LDL cholesterol (mg/dL) | 104 ± 32 |
| HDL cholesterol (mg/dL) | 37 ± 10 |

BP—blood pressure;
LDL—low density lipoprotein,
HDL—high density lipoprotein

Plasma Samples

Archived, coded EDTA plasma samples were kept frozen (−40 C) for 0-3 years prior to assay for bFGF-IR. Plasma bFGF-IR and bFGF-like bioactivity were previously shown to be stable for 5 yrs or longer at −20 C, and for up to 3 freeze-thaw cycles (Zimering M B, Eng J. (1996). Increased basic fibroblast growth factor-like substance in plasma from a subset of middle-aged or elderly male diabetic patients with microalbuminuria or proteinuria. J Clin Endo Metab. 81, 4446-4452).

Basic Fibroblast Growth Factor Assays

Basic FGF immunoreactivity (bFGF-IR) in plasma was determined using a sensitive specific two-site enzyme-linked immunoassay (R&D Systems, Inc. Minneapolis, Minn.).

The mean minimal detectable dose of FGF-2 was 0.5 pg/mL (n=9 assays). The method was linear between 0.5-64 pg/mL. The average correlation coefficient for the runs was 0.99. The intra-assay coefficients of variation for low and high dose calibration standards or human diabetic plasma samples were ≦8%; the inter-assay coefficient of variation(s) for patient samples or calibration standards ranged from 10-14%. Recovery of bFGF-IR in diluted (1:2) samples of normal human plasma ranged from 108-123%. The dilution curves of patient plasma samples were parallel to the standard curve. aFGF, FGF-4 (hst), FGF-5, FGF-6 did not cross-react in the assay. In prior studies that employed the same bFGF-IR assay method, mean serum bFGF-IR in 15 normal subjects (men and women, ranging from 39-74 yrs old) was 0.9 pg/mL (range 0-4 pg/mL) (Zimering, M B and Thakker-Varia, S. Increased fibroblast growth factor-like autoantibodies in serum from a subset of patients with cancer-associated hypercalcemia. Life Sciences, 71 (2002) 2939-2959).

Protein A Affinity Chromatography

To separate the IgG fraction from plasma, 0.4-mL aliquots of serum were adjusted to pH 8.0 by adding 0.6 mL 100 mmol/L Tris (pH 8). The plasma was clarified by sterile filtration (Millipore Corp., Bedford, Mass.; 0.22 um) then 1 mL was applied to a 1-mL column of packed protein-A beads (Pierce and Co., Inc) equilibrated in 100 mmol/L Tris, pH 8.0. The column was washed with 15 mL 100 mmol/L Tris, pH 8.0 (flow-through fraction), and then eluted stepwise with 5×1.0 mL 0.1 mol/L citric acid, pH 3.0. The pH of the eluate fractions was adjusted to 7.5-8.0 by adding 1 mol/L Tris (pH 8.0). The second and third eluate fractions contained nearly all of the protein A-eluted protein and were pooled and assayed for growth-promoting activity. Eluate, flow-through and starting serum fractions were stored at 4 C. Recovery of human IgG averaged 92% (data from Pierce Chemical Co., Rockford, Ill.) when 5 mg/mL human IgG was applied to a 1-mL protein-A column (n=10 experiments). Activity in protein-A eluate fractions was unchanged by overnight dialysis (Spectrapor; mol wt cut-off, 14 K) in 10 mmol/L Na phosphate, pH 7.4, compared to undialyzed samples. All fractions were sterile filtered (Millipore Corp., Bedford, Mass.; 0.22 um) before assay for growth-promoting activity.

Inhibitory activity in endothelial cells in the protein A eluate fractions was stable after storage at 0-4 deg C. for 3-6 months.

Chemicals

Recombinant human bFGF was from Austral Biologicals, Inc (San Ramona, Calif.). All other chemicals and reagents were analytical grade.

Protein Determinations

Protein concentrations were determined by a bicinchoninic acid protein Assay kit (Pierce Chemical Co., Rockford, Ill.).

Data Analysis

All data are the mean±1 SD. Comparisons were made by paired and unpaired Student's t tests, Chi-square, or difference of proportion methods.

Results

Basic FGF (bFGF) is a potent endothelial cell growth factor. An unexpected significant (overall) inverse association was found between plasma bFGF-Immunoreactivity (bFGF-IR) and baseline or post-baseline laser treatment in 172 diabetic subjects enrolled in VADT who had plasma bFGF-IR determined at the baseline visit (Table B).

TABLE B

Baseline or post-baseline laser surgery by dichotomized low vs high plasma bFGF (around the median value of 4 pg/mL)

| | Dichotomized bFGF | | | | |
| --- | --- | --- | --- | --- | --- |
| | Low 0 <= bFGF <= 4 | | High bFGF > 4 | | |
| Event | N | % | N | % | p-value |
| Baseline laser surgery | | | | | |
| No | 73 | 81 | 76 | 93 | 0.01 |
| Yes | 17 | 19 | 5 | 6 | |
| Missing data | 0 | 0 | 1 | 1 | |
| Post-baseline laser surgery | | | | | |
| No | 68 | 76 | 70 | 85 | 0.03 |
| Yes | 19 | 21 | 7 | 9 | |
| Missing data | 3 | 3 | 5 | 6 | |

TABLE B-continued

Baseline or post-baseline laser surgery by dichotomized low vs high plasma bFGF (around the median value of 4 pg/mL)

| | Dichotomized bFGF | | | | |
| --- | --- | --- | --- | --- | --- |
| | Low 0 <= bFGF <= 4 | | High bFGF > 4 | | |
| Event | N | % | N | % | p-value |
| Multiple post-baseline laser surgery | | | | | |
| No | 75 | 83 | 72 | 88 | 0.13 |
| Yes | 12 | 13 | 5 | 6 | |

N-number; % subjects experiencing first or repeat laser photocoagulation for retinopathy In multivariate logistic regression, after adjusting for known risk factors for diabetic retinopathy, low plasma bFGF (p=0.01) and diabetes duration (p=0.03) were significant risk predictors for laser treatment during a 3 yr follow up period. The accompanying table (Table C) illustrated the comparison to baseline laser treatment.

TABLE C

Relative risk for baseline or post-baseline laser occurrence

| | Baseline laser | | |
| --- | --- | --- | --- |
| | OR | 95% CI | p-value |
| Plasma bFGF-IR (low vs high) | 0.24 | 0.07-0.69 | 0.01 |
| Diabetes duration | 1.08 | 1.02-1.15 | 0.007 |
| HbA$_1$c | 0.81 | 0.53-1.18 | 0.31 |
| LDL cholesterol | 1.00 | 0.98-1.02 | 0.94 | n = 172 subjects; Multivariate logistic regression was performed.
OR—odds ratio,
CI—confidence intervals Endothelial cell autoantibodies were detected in plasma from 45 of the 145 diabetic subjects who had bFGF determined at their baseline study visit.

TABLE 1

Correlation of inhibitory endothelial cell autoantibodies with risk for post-baseline laser treatment (up to 3 yrs after study enrollment)

| Post-baseline Laser (% affected Subjects) | antibody <= 90% | | antibody > 90% | | |
| --- | --- | --- | --- | --- | --- |
| | N | % | N | % | p-value |
| No | 32 | 71 | 87 | 87 | 0.0067 |
| Yes | 11 | 24 | 8 | 8 | |
| Missing | 2 | 4 | 5 | 5 | |

N = number of patients

There was a striking overall inverse correlation between low bFGF (<4.5 pg/mL, the observed upper limit in normal adult men) and detectable inhibitory autoantibodies (90% or lower) in 145 samples from 145 subjects. 76% of patient with inhibitory autoantibodies had low bFGF compared to 24% of patients with inhibitory autoantibodies who had high bFGF (p<0.0001 for the difference; not shown).

The presence of inhibitory autoantibodies, defined as endothelial cell number <=90% of control after 2 days' incubation in the presence of test eluates, correlated significantly with the 3 yr risk for laser treatment: 24% vs 8%, p=0.007 for the difference (Table 1). The overall prevalence of inhibitory antibodies (<=90% activity) in the group of 145 subjects was 45/145=31% (Table 1).

TABLE 2

Lack of correlation between inhibitory endothelial cell autoantibodies and traditional risk factors for diabetic retinopathy: baseline HbA1c or diabetes duration

|  | antibody <= 90% | | antibody > 90% | | |
|---|---|---|---|---|---|
|  | N | % | N | % | p-value |
| HbA1c |  |  |  |  |  |
| 7.5-8.4% | 9 | 20 | 25 | 25 | 0.93 |
| 8.5-9.4% | 17 | 38 | 35 | 35 |  |
| 9.5-10.4% | 10 | 22 | 20 | 20 |  |
| >=10.5% | 9 | 20 | 20 | 20 |  |
| Duration |  |  |  |  |  |
| 0-<5 yrs | 8 | 18 | 17 | 17 | 0.67 |
| 5-<10 yrs | 16 | 36 | 27 | 27 |  |
| 10-<15 yrs | 11 | 24 | 22 | 22 |  |
| 15-<20 yrs | 5 | 11 | 19 | 19 |  |
| >=20 yrs | 5 | 11 | 15 | 15 |  |

The occurrence of inhibitory endothelial cell antibodies did not correlate with baseline glycemic control (hemoglobin A1c), diabetes duration (Table 2), or albumin/creatinine ratio. The latter are all known risk factors for diabetic retinopathy. The significance of the latter observation, is that endothelial cell inhibitory autoantibodies in adults with advanced type 2 diabetes appear to be an independent risk factor for macular edema requiring laser therapy.

EXAMPLE 3

The Occurrence of Complications in a Subgroup of Diabetic Patients Correlates with the Presence of Endothelial Cell Autoantibodies The occurrence and severity of specific complications was compared in diabetic patients with the presence of autoantibodies in a subgroup of 5 subjects whose clinical history is shown in below.

Subjects

Case 1: Patient with type 1 dm×10-15 yr. Family history significant for breast cancer in a sister. Diabetic and related complications include: hypertension, hyperlipidemia, gastroparesis, seizures or pseudoseizures, intolerance to thiazide diuretics (profound weakness), calcium channel antagonists (profound weakness) or statin medications (severe GI pain). Had recurrent episodes of TIA and subsequently developed three strokes (IgG, IgM anti-cardiolipin and anti-neutrophil cytoplasmic antibodies were all negative).

Case 2: Patient with type 2 dm×10-15 yrs. Family history significant for mother with diabetes and end stage renal disease. Diabetic and related complications include: hypertension and painful peripheral neuropathy.

Case 3: Patient with type 2 dm×20 yrs. Family history significant for Alzheimer's dementia in father. Diabetic and related complications include: depression, bilateral thigh weakness consistent with diabetic amyotrophy, multi-focal neurological signs consistent with mononeuritis multiplex, clinically significant macular edema requiring focal laser ×2, and non-ischemic cardiomyopathy with refractory paroxysmal atrial fibrillation requiring implantation of an automated implantable defibrillator, as well as prior and subsequent frequent episodes of unexplained dizziness.

Case 4: Patient with type 2 dm×7 yrs. Family history significant for mother with breast cancer and father with colon cancer. Diabetic and related complications include: depression, painful radiculopathy, dry age-related macular degeneration, cataracts, mild nonproliferative diabetic retinopathy. Hospitalized 4-5 times over a ten month period and treated for recurrent congestive heart failure, pulmonary hypertension. Significant findings included: concentric left ventricular hypertrophy, large pericardial effusion, moderately severe aortic insufficiency, aneurysmal dilatations of left ant descending, left circumflex and right coronary arteries, bradyarrythmias with hypotension requiring placement of a permanent pacemaker, and hematochezia from unknown source requiring multiple blood transfusions. ANA and ESR were both within normal limits. All symptoms and signs subsequently resolved.

Case 5. Patient with type 2 dm×15 yrs and rheumatoid arthritis treated with methotrexate and gold. Family history significant for mother with lung cancer. Renal function was normal at baseline and throughout the 5 yr follow up period. Diabetic related complications included painful peripheral neuropathy.

Control 1. 57 yr old male with type 2 dm×7 yrs. Family history significant for sister with diabetic blindness. No diabetic retinopathy or neuropathy.

Samples were collected and autoantibodies were screened, as described above, in Example 1.

The key questions addressed by illustrations as shown in FIGS. 1-5 and Table 3 were: a) whether the autoantibody level and potency correlates with severity of diabetic complications in the subject; b) how long the autoantibodies persist in the circulation in various patients; c) whether long persistence of autoantibodies correlates with increased risk for visual impairment; and d) whether the appearance of autoantibodies precedes the development of any other unexpected or unusual medical complications to diabetes, e.g. non-ischemic cardiomyopathy, TIA, stroke.

TABLE 3

Indices of glycemia, renal function and atypical neurological or cardiovascular occurrences during 5 yr follow up period in four patients.

| Pt no. | Age/sex race | Parameter, mean | Follow-up year | | | | |
|---|---|---|---|---|---|---|---|
|  |  |  | 1 | 2 | 3 | 4 | 5 |
| 1. | 52/M/ Cauc | HbA1c (%) | 9.9 | 8.3 | 8.7 | 10.2 | 12.2 |
|  |  | Sr creat (mg/dL) | 1.1 | 1.3 | 1.4 | 1.4 [2.0] | 1.6 |
|  |  | Neurol events |  | tia | tia^ | tia | 3 strokes |
| 2. | 58/M/Afr-Am | HbA1c (%) | 10.6 | 10.6 | 12.5 | 9.8 | 10.1 |
|  |  | Sr creat (mg/dL) | 1.1 | 1.1 | 1.4 | 1.9 [2.5] | 3.1 |
|  |  | Neurol events |  |  |  |  | tia^^ |
| 3. | 55/M/ Caucasian | HbA1c (%) | 9.5 | 8.8 | 8.5 | 9.6 | 9.0 |
|  |  | Sr creat (mg/dL) | 1.3 | 1.4 | 1.5 | 1.8 [3.2] | 2.0 |
|  |  | Neuro and cardiac complications* | depr, diab syncope, amyotr refractory PAF, AICD | | | | |
| 4. | 67/M/ Caucasian | HbA1c (%) | 9.2 | 7.2 | 6.8 | 5.9 | 6.3 |
|  |  | Sr creat (mg/dL) | 1.1 [1.2] | 1.2 | 1.3 | 1.3 | 1.5 |
|  |  | Neuro and cardiac Complications** | chf, bradyarrythmia, AI, pacemaker | | | | |

[ ] - 24 hr urine protein, mg
^negative work-up including MRI, EEG, carotid ultrasound
^^negative CT scan of the head
*normal coronaries, normal carotids, "non-ischemic cardiomyopathy"
**aneurysmal dilatation of left anterior descending, left circumflex and right coronary arteries, concentric left ventricular hypertrophy, moderate pericardial effusion

EXAMPLE 4

Plasma bFGF does not Correlate to Plasma Autoantibody Levels

In experiments illustrated by FIGS. 6-10, and Tables 4-6 using autoantibodies from the same subgroup described above (Example 3) and additional patients, the following experiments determined: 1) whether the in vitro effects and mechanism of action of the autoantibodies in endothelial cells, neurons, and adult rat atrial cardiomyocytes (HL-1) are consistent with their possible in vivo role in contributing to specific diabetic complications; 2) the evidence that the active component in protein-A eluted fractions is autoantibodies, and 3) the likely cellular targets of the autoantibodies.

Samples were collected and autoantibodies were screened as described above in Example 1.

Since both potency and titer of autoantibodies might be involved in mediation of tissue effects, these characteristics were compared in three groups of diabetic patients differentiated by their level of plasma bFGF-IR, i.e. high bFGF-IR, low bFGF-IR, or undetectable bFGF-IR. The results are illustrated in FIG. 17.

Figure 17:
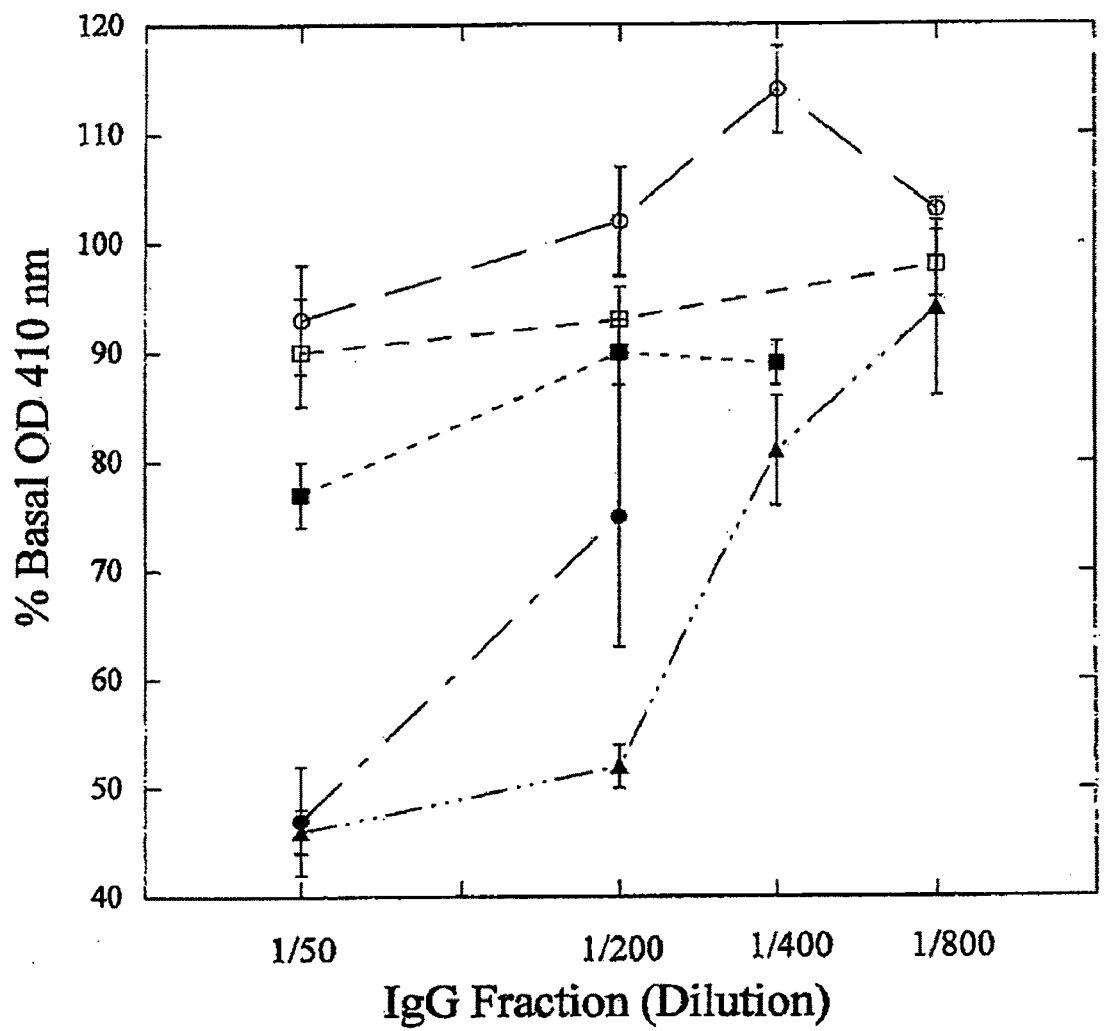
FIG. 17 shows a graph illustrating an antibody dose-dilution curve in protein-A-eluate fractions from a diabetic plasma with high bFGF (open circles), or patient 14 from Table 4 (open squares), patients 2, 3 and 4 from Table 3, (solid squares, solid triangles and solid circles, respectively), as described in Example 4, infra.

The potency and titer of inhibitory bioactivity in protein-A eluates of plasma, from representative diabetic subjects with undetectable bFGF-IR (pts 2, 3, 4, Table 3) exceeded that of representative diabetic plasmas with either low, or high detectable plasma bFGF-IR levels (FIG. 17). The IgG fraction of plasma from one patient, pt 4 (solid triangles, FIG. 17), caused significant inhibition of endothelial cell number (~80% of control cell number after 2 days in culture) at a concentration of 1 ug/mL. Despite an overall correlation between inhibitory auto antibodies and low bFGF levels in 145 subjects tested, low bFGF-IR level was not a true or reliable indicator of the presence of significant titers of autoantibodies in all plasmas. It only provided an initial clue to their occurrence. Testing of additional plasmas found some with high bFGF levels and significant autoantibodies, and others with low or undetectable bFGF levels and no auto antibody.

EXAMPLE 5

Clinical Characteristics of a Subgroup of Diabetic Subjects with Low or Undetectable Plasma bFGF-IR Levels Samples were obtained three years later from three diabetic patients previously tested to determine whether inhibitory activity was still present in protein-A eluates.

Samples were collected and autoantibodies were screened as described above in Example 1.

TABLE 4

Clinical characteristics in a subgroup of diabetic subjects with low or undetectable plasma bFGF-IR levels: relation to albuminuria, and/or retinopathy

| Patient no. age/sex | bFGF (pg/mL) | T (yrs) | Growth activity (%)[a] | DM (yrs) | HbA$_1$c (%) | ACR (mg/g) | Retinopathy/ treatment | S cr (mg/dL) |
|---|---|---|---|---|---|---|---|---|
| Retinopathy | | | | | | | | |
| 1. 59/M | 0 | 3 | 78 | 15 | 9.6 | 121 | CSME, focal laser × 4 | 1.0 1.9 |
| 2. 58/M | 0 | 3 | 46 | 15 | 9.6 | 906 | CSME, s/p laser laser × 2 | 1.3 2.2 |
| 3. 67/M | 0 | | 79 | 10 | 10.8 | 234 | CSME laser × 3 | 0.9 1.7 |
| 4. 70/M | 0 | 3 | 41 | 7 | 9.5 | 830 | mild non-prolif AMD | 1.1 1.3 |
| 5. 60/M | 0 | | 90 | 10 | 9.5 | 135 | mod non-prolif CSME, laser ou | 0.7 0.5 |
| 6. 67/M | 0 | | 88 | 15 | 8.1 | 14 | s/p laser, focal laser | 1.1 |
| 7. 70/M | 0 | | 82 | 20 | 9.2 | 16 | macular drusen | 0.9 |
| Minimal, or no retinopathy | | | | | | | | |
| 8. 66/M | 0 | | 106 | 3 | 11.8 | 24 | none | 1.0 |
| 9. 57/M | 0 | | 108 | 17 | 10.8 | 10 | minimal | 0.8 |
| 10. 79/M | 0 | 3 | 109 | 10 | 9.0 | 151 | none | 1.5 1.4 |
| 11. 59/M | 3.3 | | 94 | 5 | 11.4 | 14 | none | 1.1 |
| 12. 46/M | 0 | | 105 | 2 | 8.6 | 28 | none | 1.0 |
| 13. 58/M | 0 | | 94 | 16 | 7.5 | 41 | none | 0.8 |
| 14. 49/M | 2.0 | | 89 | 5 | 11.8 | 45 | none | 1.0 |

DM—diabetes mellitus duration,
ACR—baseline albumin creatinine ratio,
S cr—serum creatinine,
T—time interval between growth activity determinations,
CSME—clinically significant macular edema, mod-moderate, non-prolif-(erative),
ou—both eyes.
AMD—age-related macular degeneration.
[a]One-fiftieth dilution of the protein-A eluated fractions of plasma were added to endothelial cells. Growth activity was assessed as % change in OD$_{410\,nm}$ as described in Materials and Methods.

Figure 18:
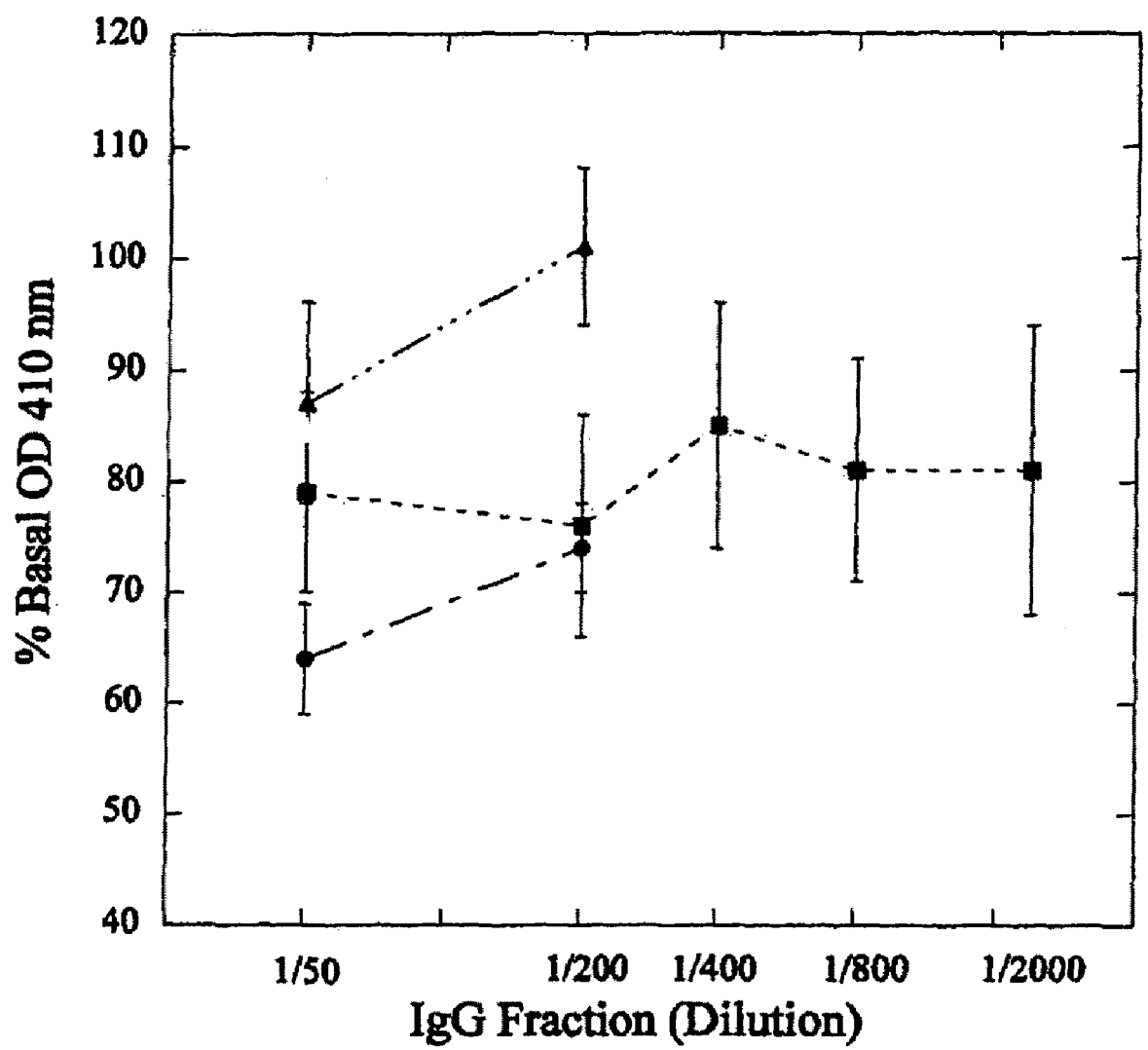
FIG. 18 shows a graph illustrating an antibody dose-dilution curve in protein-A-eluate fractions from three diabetic plasmas after 3 years of study treatment: patients 2, 3 and 4 from Table 3 (square, triangle and circle, respectively), as described in Example 5, infra.

In three of the same patients tested three years later during ongoing study treatment, potent inhibitory activity was still evident in protein-A eluates from two diabetic plasmas (FIG. 18, patients 2, 4, from Table 3), but was markedly diminished in a third diabetic plasma (FIG. 18, solid triangles, patient 3, Table 4) (FIG. 18). The lowest concentration tested of plasma autoantibodies which caused significant inhibition of endothelial cell number (80%) was ~1 ug/mL from patient 2, Table 3, (squares at 1:2000 dilution FIG. 18).

In a type 1 diabetic patient who consented to participation in a different approved study, the relationship between antibody titer/potency and visual changes was analyzed. The patient's clinical history is summarized in Subjects, supra. He had type 1 diabetes ×10-15 yrs and recurrent macular edema in both eyes, Patient 1, Table 3, antibody potency (determined at a $1/50^{th}$ dilution, ~20 ug/mL) was compared to the frequency of laser episodes to treat either proliferative retinopathy, i.e. new blood vessel growth, or macular edema, leakage of plasma protein causing visual impairment. It is evident from FIG. 1, that around the time that persistent potent inhibitory antibody activity (ranging from 45-79%) could be demonstrated in the patient's plasma samples, the patient experienced reversible visual impairment in the left eye, and as yet irreversible visual impairment in the right eye which together required a total of 11 episodes of laser photocoagulation, 3 panretinal for proliferative changes, and 8 focal for macular edema during 58 months followup. From Table 3, it is notable that despite periods of relative improvement in his glycemic control (HbA1c) during years 2, 3, significant antibody and the need for ongoing focal laser treatment for recurrent macular edema persisted during the same time period. It is also worth noting that in both eyes, and especially in the right eye, FIG. 1, panel B, multiple focal laser episodes for macular edema preceded the development in the same eye of proliferative retinopathy—indicative that diabetic macular edema generally occurs at an earlier stage than proliferative retinopathy.

Also noteworthy in this patient is the potency of his inhibitory endothelial cell autoantibodies i.e. with a 45% cell number (FIG. 1C) contact with this patients' autoantibodies resulted in death in 55% of cells after 2 days culture. This process is time-dependent over 1-3 days, 46%, 55% and 67% cell death occurred, with maximal cell death notable after 3 days in culture. Significant cell loss was already evident after <=24 hrs.

Figure 2:
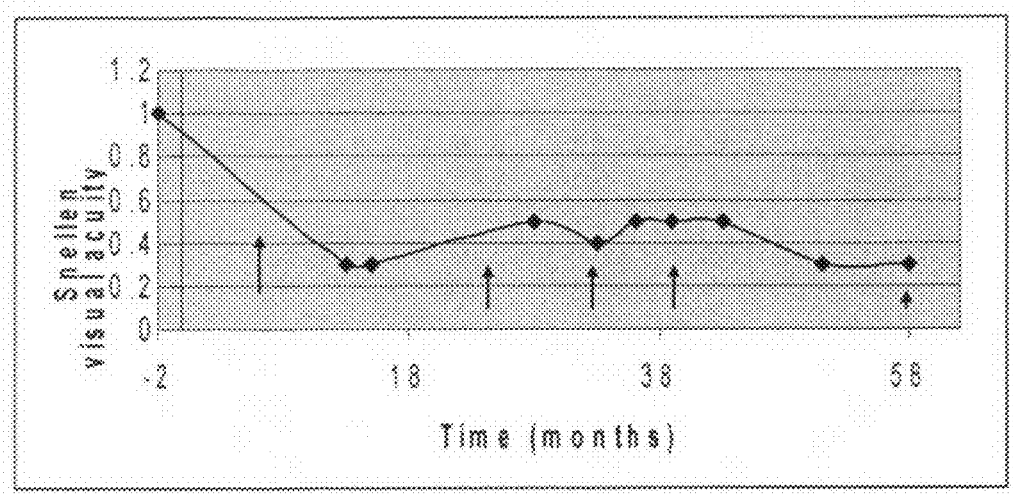
FIG. 2 shows three charts illustrating visual acuity changes in: A) right eye in patient 2: relation to focal laser occurrences; B) endothelial cell autoantibodies; and C) glycemic control, as described in Example 5, infra.
Figure 2:
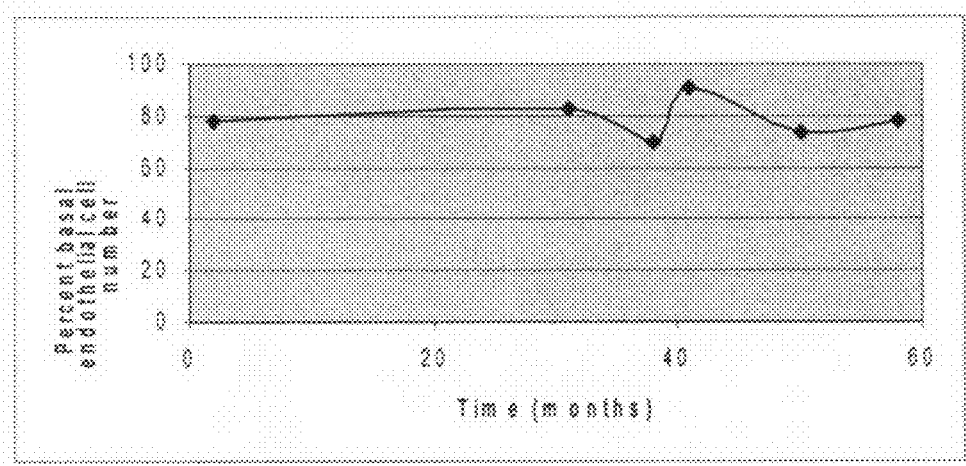
Figure 2:
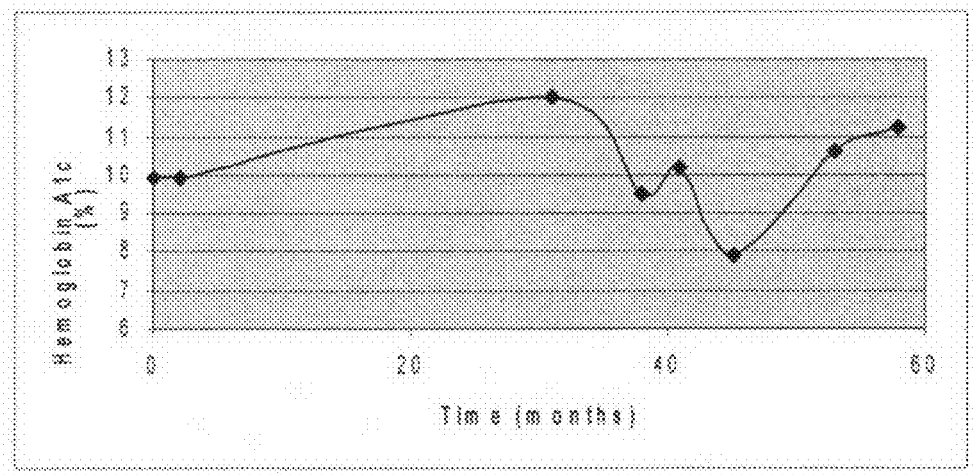

Attention was next focused on a subgroup of VADT patients who manifested recurrent macular edema requiring multiple laser photocoagulation interventions. In patient 2, Table 3, the patient experienced 5 focal laser treatments to the right eye for recurrent macular edema, and suffered significant visual impairment during the same time period (FIG. 2). Potent inhibitory endothelial autoantibodies were present throughout the same—58 month follow-up period, and were relatively unaffected by a 6-month period of significant improvement in the patients glycemic level, i.e. Hba1c (FIG. 2). Renal insufficiency progressed during the follow up period (Table 3), and the patient suffered a TIA during follow up year 5.

Figure 5:
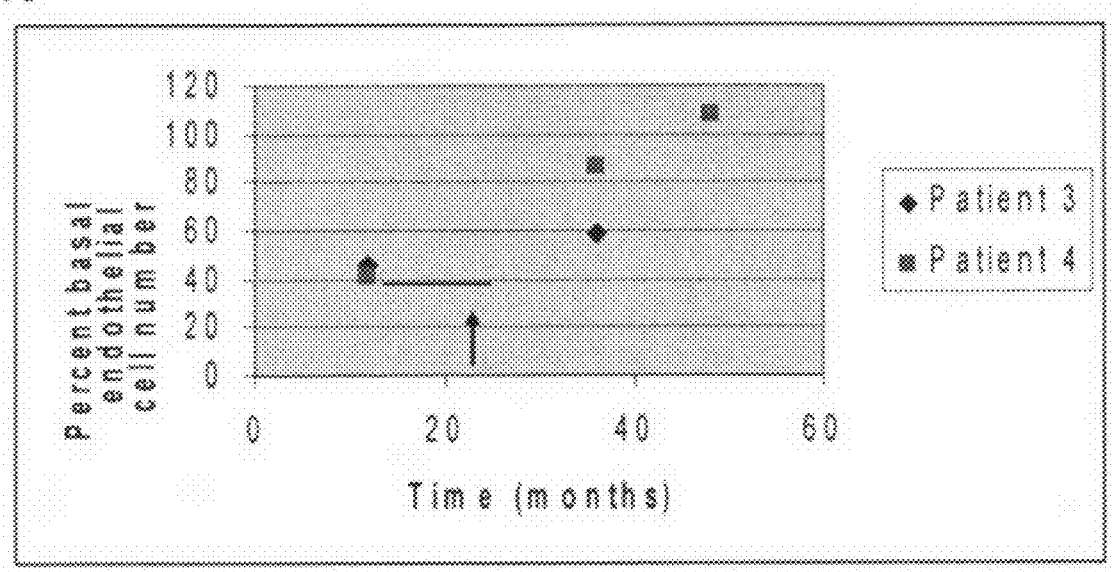
FIG. 5 shows a chart illustrating plasma inhibitory endothelial cell autoantibodies preceded the development of non-ischemic cardiovascular complications in two patients with type 2 diabetes. Arrow indicates time of occurrence of refractory paroxysmal atrial fibrillation in patient 3; horizontal line indicates time of occurrence of multiple cardiovascular events in patient 4, as described in Example 5, infra.

Two additional type 2 diabetic patients had very potent endothelial cell autoantibodies (each type of antibody sample caused 50% or greater cell death after contact with cells for 2 days in culture) (patients 3, 4, Table 3). Both patients suffered unusual cardiac arrhythmias requiring implantation of defibrillator or pacemaker during years 2, 3 of follow up (Table 3) and after the appearance of potent circulating autoantibodies (FIG. 5). Autoantibodies persisted in the circulation of both patients for at least 2 yrs after initially noted (FIG. 5), and in one patient autoantibodies were evident, despite markedly improving glycemic levels 9.2% to 6.8% (pt 4, Table 3). The disappearance of autoantibodies from plasma in patient 4 (FIG. 5) coincided with near normalization of glycemia during follow up year 4 (Table 3) and resolution of his atypical cardiovascular manifestations.

It is worth noting however that patient 4 from Table 3 had no evidence for an auto-immune disease, by the usual laboratory or clinical measures (see case 4, above), despite his highly unusual syndrome, which consisted of development of multiple coronary artery aneurysms, left ventricular hypertrophy, aortic regurgitation, pericardial effusion, and reversible congestive heart failure. Takayasu's arteritis, "pulseless syndrome" is a rare autoimmune vasculitis involving large vessels in which antibodies specific for aortic endothelial cells are present in a very high percentage of cases. Takayasu's is a chronic disease characterized by coronary aneurysms, high arterial afterload and aortic regurgitation resulting in heart failure and occasionally pericardial effusion. The patient we describe had features similar to Takayasu's arteritis, but most of the serious cardiac manifestations resolved at the same time his autoantibody levels disappeared (FIG. 5, patient 4).

The clinical characteristics were compared for two groups of age-matched, diabetic subjects, mean diabetes duration 11 yrs, with low or undetectable plasma bFGF-IR levels, who differed according to the presence or absence of significant retinopathy, i.e. maculopathy (Table 4). The subjects did not differ significantly in other baseline characteristics including mean: albumin/creatinine ratio, baseline HbA1c, baseline diabetes duration, or baseline serum creatinine (Table 4). One fiftieth dilution of protein-A eluates from plasma of diabetic subjects with retinopathy (n=7) displayed significantly (p=0.004) inhibitory mean bioactivity in endothelial cells (72±19%) compared to mean bioactivity from plasma of diabetic subjects without retinopathy (101±8%) (Table 4). This suggested that inhibitory endothelial autoantibodies in type 2 diabetes are predictive of an increased risk for laser treatment correlated with diabetic macular edema, or less commonly, other kinds of maculopathy, e.g. age-related-macular degeneration or macular drusen (Table 4). Moderate baseline retinopathy changes appeared to be a necessary pre-condition for the expression of diabetic macular edema among seven patients positive for inhibitory autoantibodies. For example, two patients with mild baseline retinopathy (pts 4, 7, Table 4) had a less pronounced form of maculopathy not requiring laser therapy. These data suggest that occurrence of potent endothelial autoantibodies alone is not sufficient to cause diabetic macular edema, but that duration of diabetes, prior glycemic control, micro-albuminuria, and patient age may set the stage by sensitizing retinal capillaries to the damage-inducing effects of inhibitory autoantibodies.

EXAMPLE 6

Figure 10:
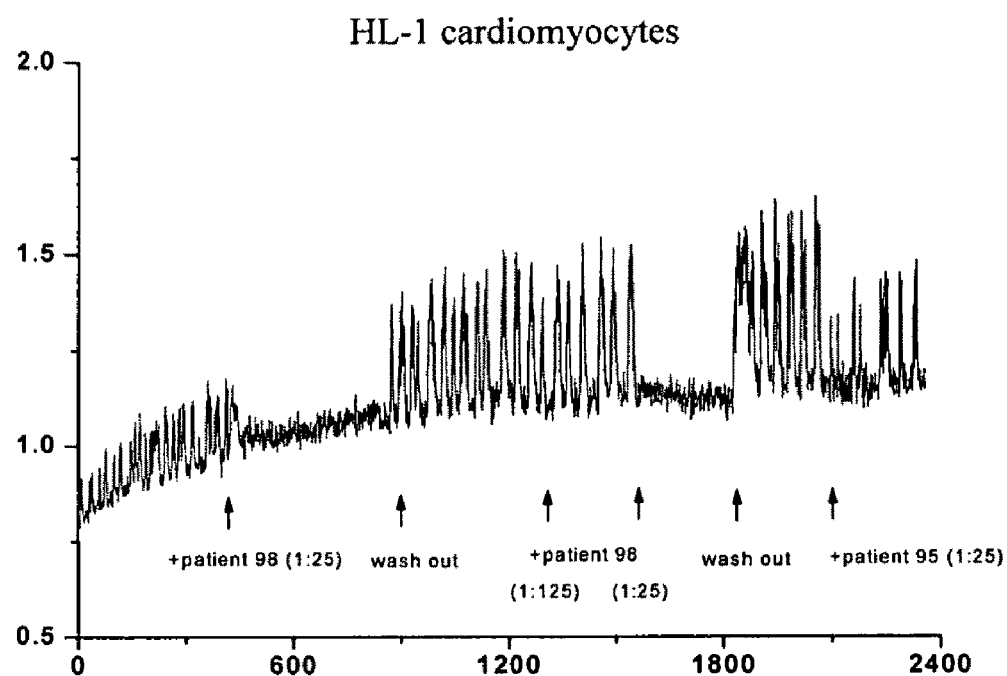
FIG. 10 shows two graphs illustrating the effects of diabetic patient autoantibodies on spontaneous bursts of intracellular calcium in HL-1 cardiomyocytes. Key: Patient 98=patient 2 as described in Subjects in Example 3; patient 95=patient 5 as described in Subjects in Example 3; patient 44115 is a control patient with stimulatory activity in endothelial cells in the protein A-eluate fraction. In graph B (to the left), the addition of an inhibitory protein-A eluate fraction (pt 98) in the continued presence of a stimulatory protein-A eluate (pt 44115) still resulted in a complete blockade of the spontaneous rhythmic calcium oscillation. This implies that in plasma from a patient in whom both stimulatory and inhibitory components of IgG may be present simultaneously, the inhibitory effects in cardiomyocytes are the dominant effect, as described in Examples 4, 6 and 7, infra.
Figure 10:
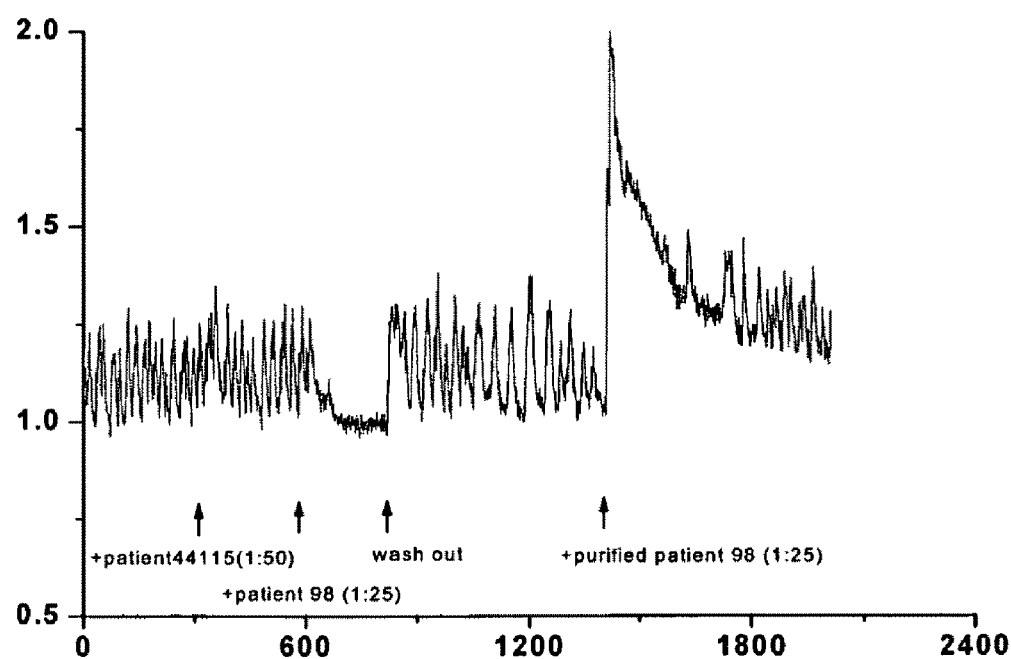

Demonstration of the Ability of Autoantibodies from Diabetic Patients to Block Neurite Outgrowth Induced by bFGF In the present study plasma was tested from a group of 14 diabetic study patients with low or undetectable plasma bFGF for autoantibodies which could inhibit endothelial cell proliferation and survival. Protein-A eluate fractions of plasma containing active endothelial cell inhibitory autoantibodies (and control fractions) were tested for their effects on bFGF-induced neurite outgrowth in rat pheochromocytoma (PC12)

cells and on spontaneous intracellular calcium oscillations in adult rat atrial cardiomyocytes (HL-1) (FIG. 10).

Samples were collected, autoantibodies were screened and bFGF was assayed as described above in Example 2.

PC12 Cells—Neurite Outgrowth Assays

Undifferentiated rat PC12 cells were obtained from American Type Culture Collection (Rockville, Md.) and plated at low density in 60 mm dishes. Three groups of 25-50 cells/dish were counted at baseline and at 3 days and 8 days after the addition of test patient protein-A eluate fractions (1:50 or 1:100 dilutions corresponding to 1-30 ug/mL protein). Neurite outgrowth represents the percentage of PC12 cells expressing more than one neurite. A neurite is defined as a cell process that is at least 2 cell diameters in length. Results represent the mean±SD of triplicate determinations in each test fraction.

Chemicals

Recombinant human bFGF was from Austral Biologicals, Inc (San Ramona, Calif.). All other chemicals and reagents were analytical grade.

Figure 3:
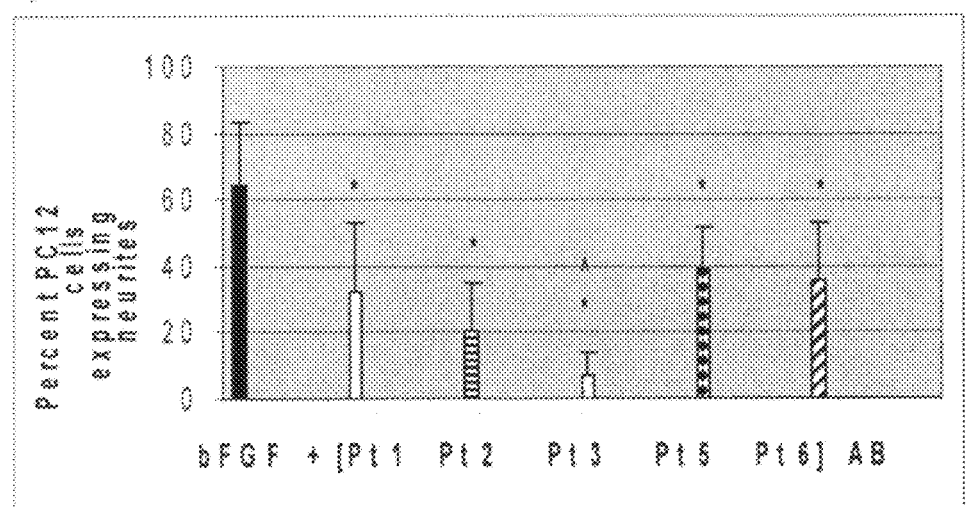
FIG. 3 shows three charts illustrating: A) Inhibition of bFGF-induced neurite expression in PC-12 cells by individual diabetic patient autoantibodies (*p<0.001 compared to bFGF; ^p<0.001 compared to pt 5, 6 AB); B) mean inhibition of bFGF-induced PC12 neurite expressions in protein-A eluate fractions from groups of patients with retinopathy and neuropathy (n=6 subjects) or without either complication (n=4 subjects); and C) neutralization of inhibition of bFGF-induced neurite expression from a representative diabetic patient autoantibodies (pt 3 AB) by the selective Rho-kinase inhibitor, Y27632, as described in Example 6, infra.
Figure 3:
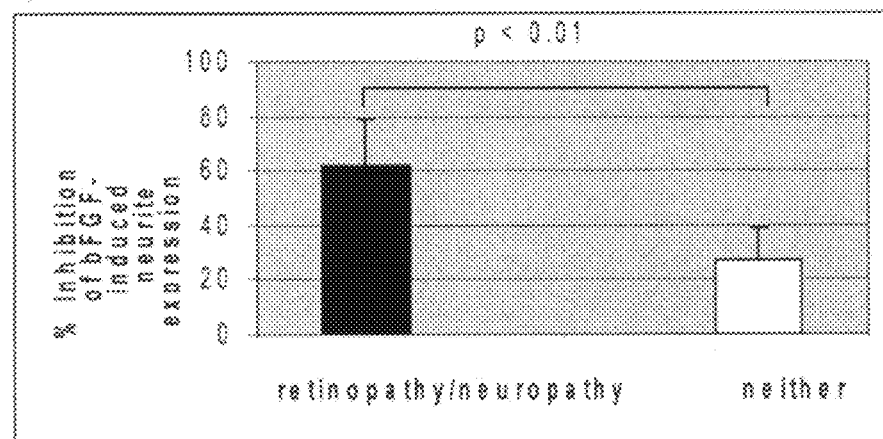
Figure 3:
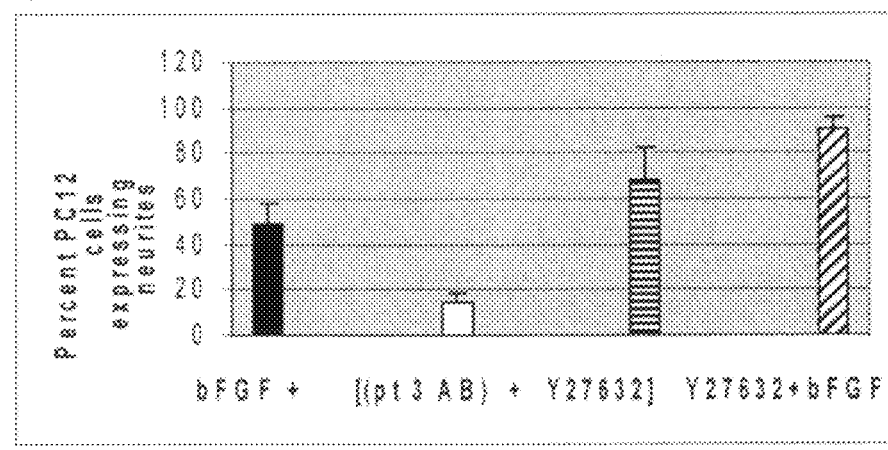
Figure 4:
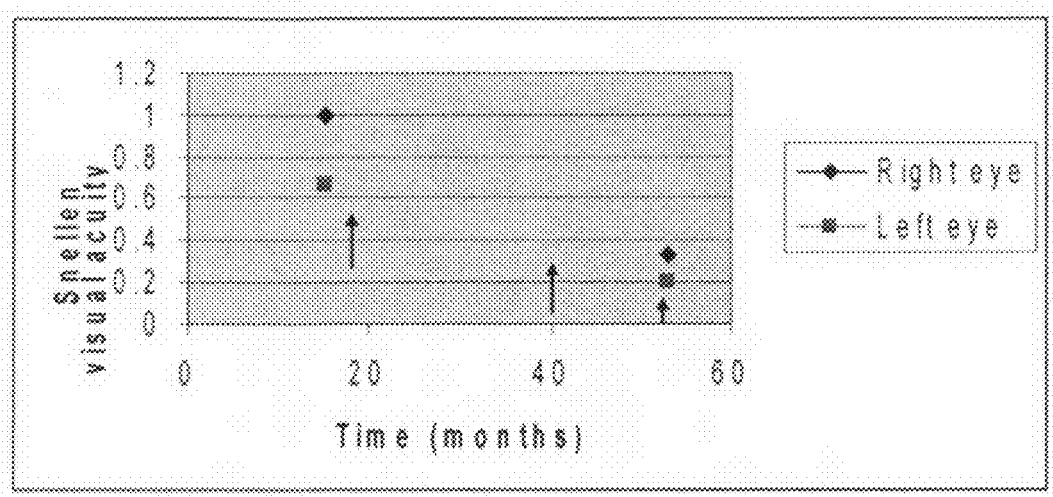
FIG. 4 shows three charts illustrating progression of visually-significant macular edema in patient #5 coincident with increasing potency of inhibitory plasma endothelial cell autoantibodies despite improved glycemia. Arrows indicate focal laser photocoagulation occurrences in both eyes, as described in Example 1, infra.
Figure 4:
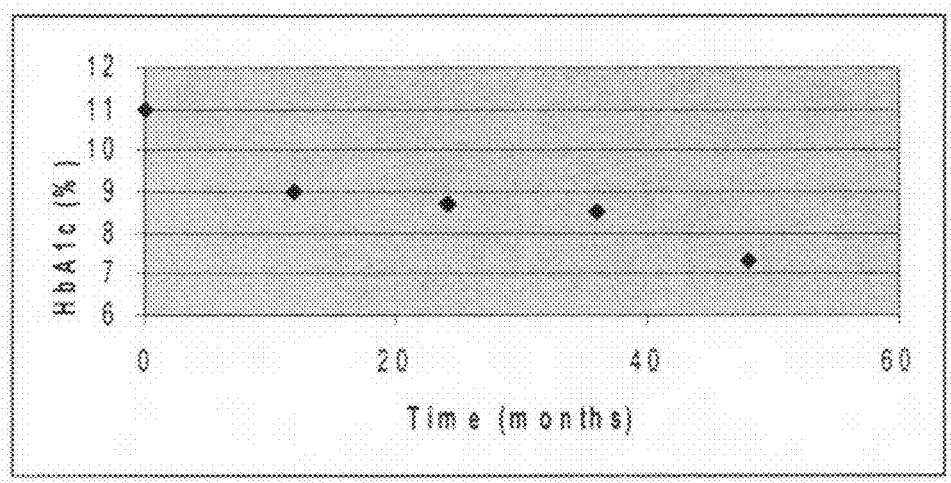
Figure 4:
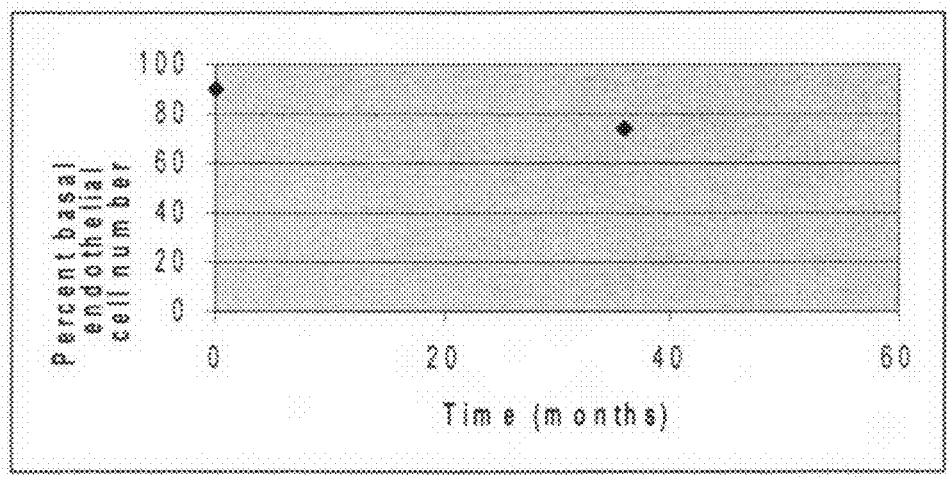

Diabetic patient autoantibodies caused a dose-dependent inhibition of bFGF-induced neurite outgrowth (1-20 ug/mL, n=8, e.g. FIG. 3). Control diabetic plasma eluate fractions that had no effect on endothelial cells did not block bFGF-induced neurite outgrowth. One notable feature of the patients with diabetic maculopathy who had inhibitory autoantibodies is that many of them also suffered with persistent painful peripheral neuropathy or atypical neuropathies such as diabetic amyotrophy, Pt 3, Table 3. Neurite outgrowth which was potently inhibited by autoantibodies from patient 3, was completely restored upon co-incubation with Y-27632 a specific Rho kinase inhibitor (FIG. 3C). These and similar data using inhibitory autoantibodies from two other diabetic subjects suggest that inhibitory autoantibodies, affect neurite outgrowth through a pathway involving activation of Rho kinase. This is potentially of broader significance in light of the known involvement of Rho kinase in sensitizing vascular smooth muscle to the effects of calcium and the consequences for altered smooth muscle contractility in hypertensive states.

TABLE 5

Recombinant basic fibroblast growth factor did not prevent or rescue endothelial cells from inhibitory effects of diabetic plasma protein-A eluates

| Pt # | Protein-A Eluate (ug/mL) | Percent Basal Cell Number | | | Percent inhibition of bFGF activity |
| --- | --- | --- | --- | --- | --- |
| | | Eluate+ | bFGF^ | eluate + bFGF | |
| 1. | 1 | 79 | 137 | 128 | 24 |
| 2. | 40 | 90 | 151 | 113 | 75 |
| 4. | 4 | 64 | 131 | 64 | 100 |

+1/50$^{th}$ dilution was added to cells, cell number determined after 48 hrs.
^dose of bFGF was 100 pg/mL except in pt 4 (200 pg/mL)
69-100%, mean 94% inhibition of proliferation from 100 pg/mL bFGF was observed in protein-A-eluates from plasma of 5 of 5 additional diabetic subjects (3 with retinopathy, 2 without retinopathy). No inhibition of proliferation from 100 pg/mL bFGF was observed in protein-A-eluates from plasma of 3 of 3 control diabetic patients without retinopathy.

The ability of diabetic patient autoantibodies to block neurite outgrowth was next studied in a larger cohort.

Study Subjects

Subjects were 14 male adults with type 2 diabetes from the Veterans Affairs Diabetes Trial.

Endothelial Cell Assays

Endothelial cell proliferation was determined after 48 hrs incubation in the presence of protein-A eluate fractions from diabetic plasmas (Zimering, M B and Thakker-Varia, S. Increased fibroblast growth factor-like autoantibodies in serum from a subset of patients with cancer-associated hypercalcemia. Life Sciences. 71 (2002) 2939-2959). Results represent quadruplicate determinations for each test fraction.

Neurite Expression in Rat PC12 Cells

Undifferentiated rat PC12 cells obtained from the ATCC were plated at low density. Groups of 25-50 cells/dish were counted at baseline and at 3 and 8 days after exposure to 10 ng/mL basic fibroblast growth factor in the presence or absence of test diabetic plasma IgG fractions and Y27632. Results represent triplicate determinations for each test fraction.

Intracellular Calcium Determination

Change in intracellular calcium was monitored with Fura-2.

Statistics

Comparisons were made using paired Student's T-test.

The mechanism of diabetic plasma protein-A-eluted fractions effects on neurites in PC12 cells, on endothelial cells and cardiomyocytes was analyzed. Subjects were 14 adults with type 2 diabetes, mean duration 11 yrs, from the Veterans Affairs Diabetes Trial (Table 6).

Figure 19:
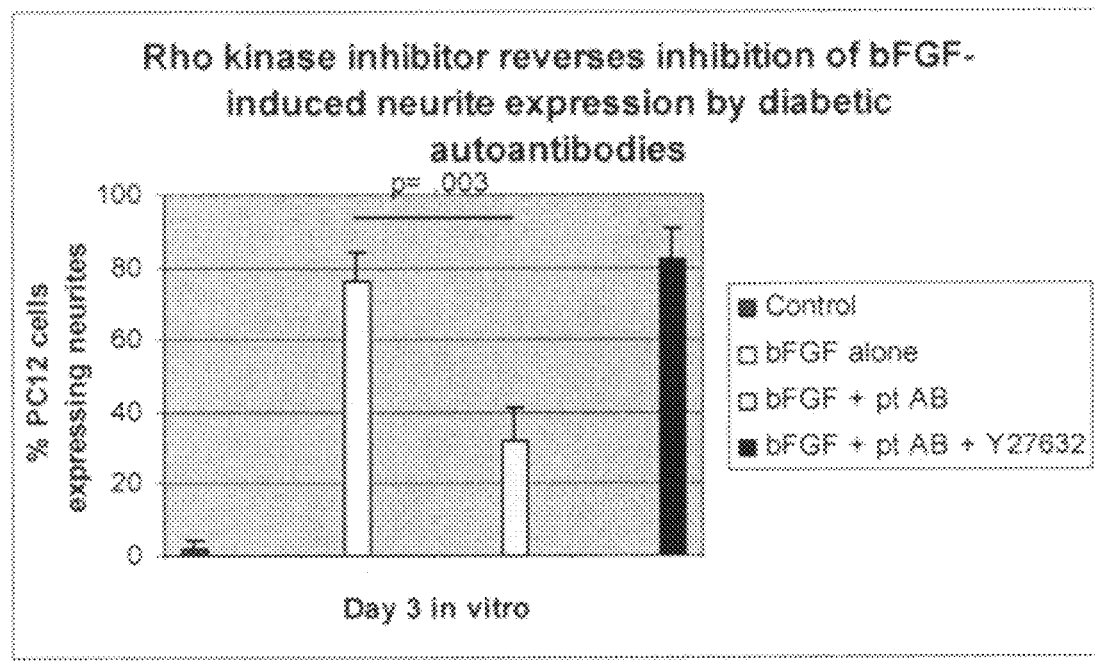
FIG. 19 shows a chart illustrating inhibition of bFGF-induced neurite outgrowth in PC12 cells by IgG fractions from retinopathy/neuropathic plasmas: reversal by Rho kinase inhibitor Y27632. This suggests that the IgG activate the Rho kinase pathway in inhibiting neurite extension as described in Example 6, infra.
Figure 19:
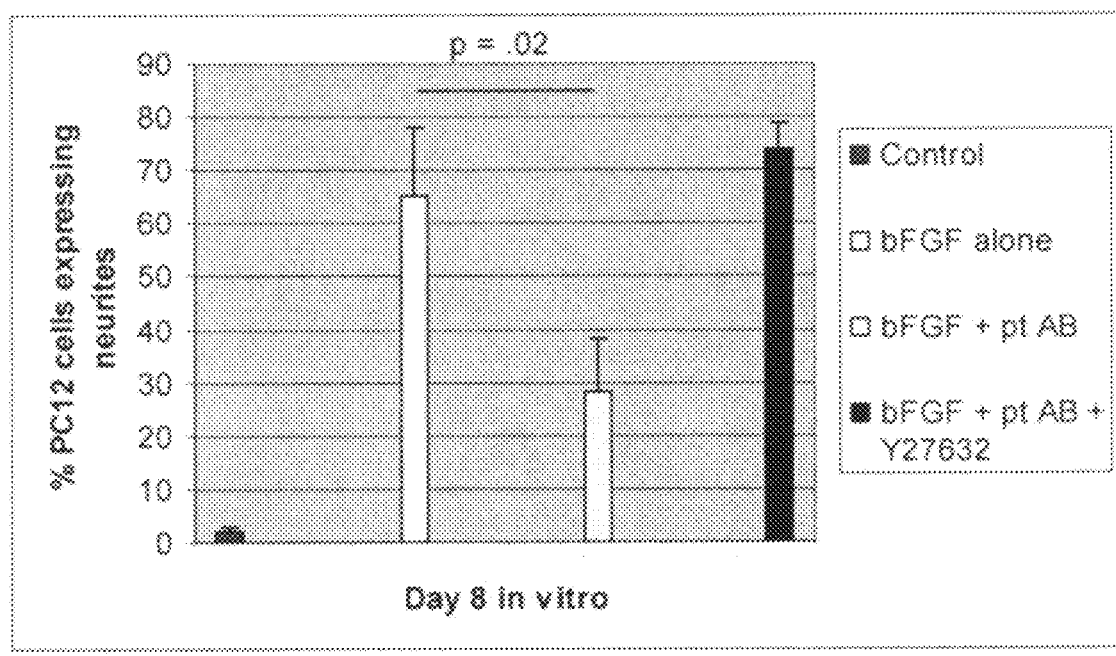

Autoantibodies from type 2 diabetes blocked neurite outgrowth in bFGF-stimulated PC12 cells. The process is Rho kinase dependent, as evidenced by the finding that a specific Rho kinase inhibitor, Y27632 (1 uM) completely restored neurite outgrowth by bFGF (10 ng/mL) in the presence of 'blocking' autoantibodies from three different diabetic patients (FIG. 19). Inhibition of bFGF-induced neurite outgrowth was dose-dependent (1-20 ug/mL, n=8) and was not exhibited in autoantibodies (n=3) lacking significant inhibitory activity on endothelial cells. The autoantibodies from diabetic retinopathy subjects (maculopathy) caused significant inhibition of endothelial cell growth (72±20%, n=7) compared to autoantibodies from diabetic subjects without retinopathy (101±8%, n=7, p=0.004 for the difference). Inhibitory autoantibodies caused endothelial cell retraction from attachment points in extracellular matrix, strong expression of F-actin immunoreactive stress fibers, and dose-dependent increases in intracellular calcium. Effects were substantially reduced upon denaturation by boiling antibodies. Purified inhibitory endothelial autoantibodies (2 ug/mL) interrupted spontaneous calcium oscillation and caused large increases in cytosolic intracellular calcium in HL-1 cardiomyocytes. Control diabetic autoantibodies had much less if any effect on intracellular calcium. These results suggest that potent inhibitory endothelial autoantibodies in plasma from type 2 diabetes with macular edema and/or painful neuropathy may have inhibitory effects in cardiac and neuronal cells.

TABLE 6

Baseline characteristics in study subjects

| Variable | Retinopathy (n = 7) Mean SD | No retinopathy (n = 7) Mean, SD | P value |
| --- | --- | --- | --- |
| Age (yrs) | 64 ± 5 | 59 ± 11 | 0.27 |
| Diab (yrs) | 13 ± 4 | 8 ± 6 | 0.11 |
| HbA1c (%) | 8.3 ± 1.4 | 9.7 ± 1.2 | 0.08 |
| bFGF (pg/mL) | 0 ± 0 | 0.7 ± 1.3 | 0.16 |
| Endothelial act (%)* | 72 ± 20 | 101 ± 8 | 0.004 |

*activity represents percent basal endothelial cell number after 2 days incubation with plasma protein-A eluate fractions Conclusion Protein-A eluate fractions of plasma from a subgroup of diabetic patients with low plasma bFGF and clinically significant retinopathy and/or neuropathy caused inhibition of cell proliferation in endothelial cells, and inhibition of bFGF-induced neurite outgrowth in PC12 cells. The active protein-A eluate fractions induced strong expression of F-actin stress fibers in endothelial cells, and dose-dependent increases in intracellular calcium. Neurite outgrowth blocking activity in protein-A eluate fractions from the same patients was abolished by co-incubation with the specific Rho kinase inhibitor Y27632.

These data suggest that spontaneously-occurring autoantibodies in type 2 diabetic plasma may be capable of affecting a wide range of cellular targets.

EXAMPLE 7

Figure 7:
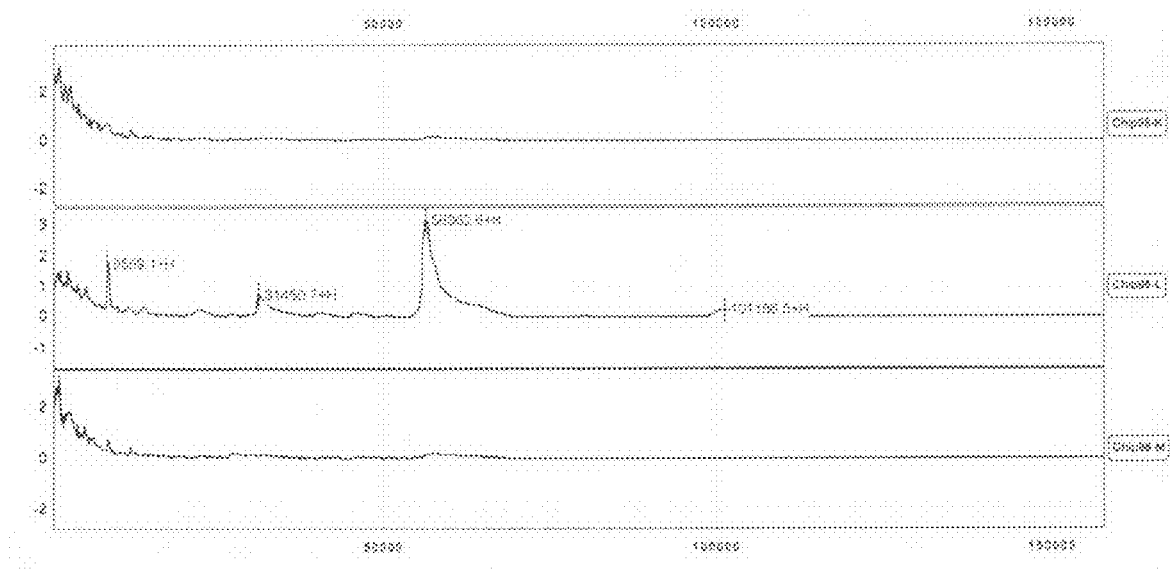
FIG. 7 shows a graph illustrating SELDI-TOF mass spectrometry of the inhibitory protein-A-eluate fraction from plasma of a representative diabetic patient (patient 2) with recurrent macular edema, as described in Examples 4, 7 and 9, infra.

Apparent MW, Stability and Effects of Diabetic Plasma Autoantibodies on Intracellular Calcium One ug/mL of a hydroxyapatite (HA)-purified peak inhibitory protein-A-elute fraction from pt #2, Table 3 plasma caused significant inhibition of basal (79%) or bFGF-induced bioactivity in endothelial cells (Table 5). Analysis of the same purified fraction by SELDI-TOF mass spectrometry revealed IgG components with apparent MWs corresponding to heavy chains (56 kD), heavy chain dimers (101 kD) or heavy chain fragments (31 kD) with the largest peak corresponding to heavy chains (FIG. 7).

The same purified fraction was tested for its effects on intracellular calcium in spontaneously active rat HL-1 cardiomyocytes (FIG. 10). The purified component of patient 2 diabetic plasma autoantibodies (2 ug/mL) that was maximally active in inhibiting endothelial cell number caused a large increase in intracellular calcium that interrupted spontaneous calcium oscillation in HL-1 cardiomyocytes (FIG. 10). The unpurified patient 2 protein A eluted fraction that had similar inhibitory activity in endothelial cells caused reproducible inhibition of spontaneous calcium oscillations in HL-1 cardiomyocytes, at 20 ug/mL (1:25 dilution) but no effect at a five-fold lower concentration (FIG. 10). Protein-A eluted fractions from two other diabetic subjects (patient 95 corresponding to case 5, described supra) and patient 44115—an unusual eluate with growth stimulatory effects on endothelial cells had less or different effects on calcium oscillations (FIG. 10). Addition of patient 2 antibodies to HL-1 cells in the continued presence of endothelial cell stimulatory antibodies (44115) did not interfere with the inhibitory effect of the patient 2 inhibitory antibodies.

Figure 8:
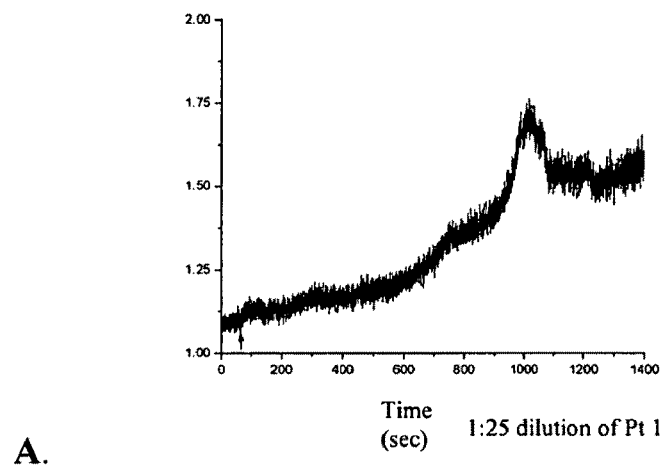
FIG. 8 shows three graphs illustrating dose-dependent changes in intracellular calcium induced by patient 1 (patient 1) autoantibodies. Graphs A, B and C reflect 1:25, 1:100 and 1:200 dilutions of patient 1 autoantibodies, respectively, as described in Examples 4 and 7, infra.
Figure 8:
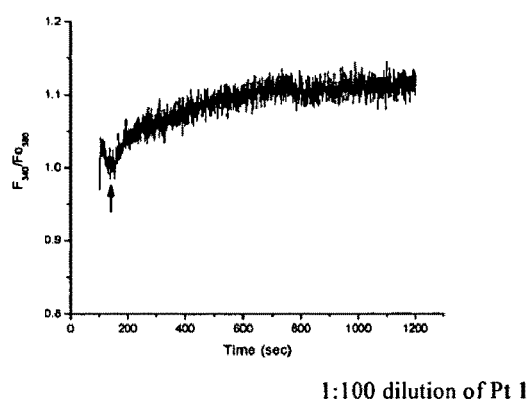
Figure 8:
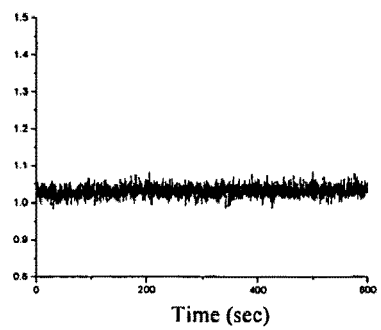
Figure 9:
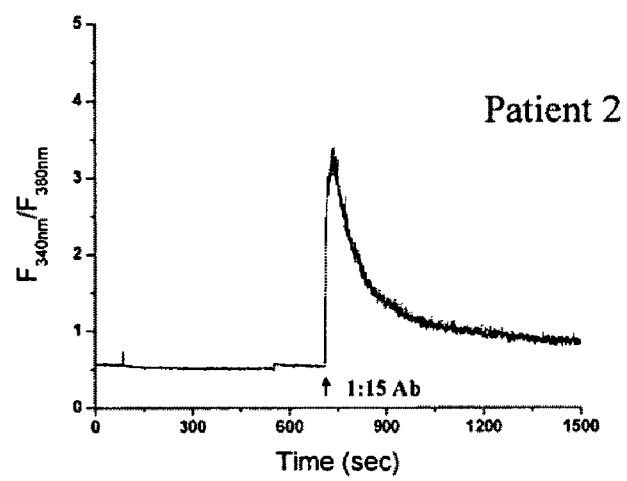
FIG. 9 shows two graphs illustrating dose-dependent increases in intracellular calcium in endothelial cells by patient 2 autoantibodies. Graphs A and B reflect 1:15 and 1:50 dilutions of patient 2 autoantibodies, respectively, as described in Examples 4 and 7, infra.
Figure 9:
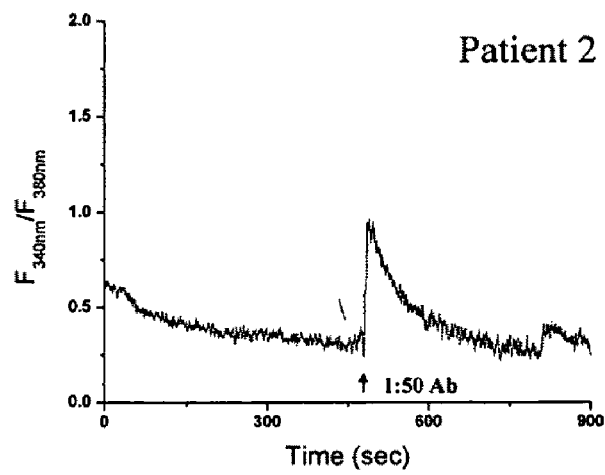

Protein-A-eluted fractions from patient 2 caused similar large dose-dependent increase in intracellular calcium in endothelial cells (FIG. 9). Autoantibodies from patient 1, Table 3, caused dose-dependent increases in intracellular calcium in endothelial cells, the minimal effective concentration of unpurified antibodies was 15 ug/mL (FIG. 8).

Nearly all of the inhibitory activity in endothelial cells from 5 of 5 diabetic plasma autoantibodies was retained after dialysis of the antibodies on membranes with a MW cutoff of 30 kD. Most of the activity (65%) was lost after heating eluate fractions from 3 of 3 diabetic plasmas to 95 deg C. for 5 mins. Most (78%) of the activity in eluates from 4 of 4 diabetic plasmas survived treatment with reducing agents, 6 mM dithiothreitol for 2 hrs at room temp. These results are consistent with the possibility that heavy chains of IgG can contribute to significant inhibitory activity in endothelial or other cells. This implies that the inhibitory effects from circulating autoantibodies may be quite long-lasting not requiring persistence of intact IgG and that there may be greater corresponding tissue penetration and diffusion from such smaller, active IgG fragments. Therefore, treatment should be instituted early, at the stage when clinical signs are present together with intact IgG, since after the intact IgG starts to dissociate into fragments, the fragments are more highly tissue penetrant and therefore harder to remove from the circulation, and capable of causing more tissue damage.

EXAMPLE 8

Validation of a Positive Test for Inhibitory Endothelial Cell Autoantibodies to Detect Pathological Complications of Diabetes This example demonstrates that endothelial cell antibodies are present in patients with type 2 diabetes and proliferative retinopathy (Table 7). These results confirm the association between inhibitory endothelial cell antibodies and known cases of breast cancer, or autoimmune disease, e.g. rheumatoid arthritis and treated colon cancer (Table 7).

These examples demonstrates the association between inhibitory endothelial cell autoantibodies and the following conditions: 1) macular edema in type 2 diabetes, 2) visually significant cataract, 3) other forms of non-diabetic maculopathy, e.g. age-related macular degeneration in a patient with treated breast cancer, 4) bladder cancer or small cell lung cancer incidence in which potent endothelial cell autoantibodies were present in otherwise normal healthy control subjects up to 7 yrs prior to the diagnosis of fatal aggressive forms of cancer.

Samples were collected and autoantibodies were screened as described above in Example 1.

TABLE 7

Data on endothelial cell inhibitory activity in plasma from 21 other adult patients (>40 yrs old) with longer term observational follow up, ~10 yrs. To test for the ability of inhibitory activity in the plasma fraction containing IgG, where inhibitory is defined as <=90%, to detect the presence of a previously unexpected significant medical condition. Known conditions associated with endothelial cell antibodies or inhibitory activity include: cancer, proliferative diabetic retinopathy, and certain auto-immune diseases.

| True negatives | False Positive | Specificity = TN/(TN + FP) |
|---|---|---|
| 1. 106% | 1. 60% prolif DR | 3/(3 + 5) = 37% |
| 2. 103% | 2. 74%-treated breast cancer | |
| 3. 98% | 3. 40%-advanced breast cancer | |
| | 4. 55% prolif DR | |
| | 5. 80% rheumatoid arthritis | |

| True positives | False negatives | Sensitivity = TP/(TP + FN) |
|---|---|---|
| 1. bladder cancer 76% | None | 13/(13 + 0) = 100% |
| 2. laser (CSME) 65% | | |
| 3. age-related macular degeneration, treated breast cancer 72% | | |
| 4. laser (CSME) 77% | | |
| 5. laser (CSME) 83% | | |
| 6. transitional cell carcinoma (TCC) renal pelvis 46% | | |
| 7. laser (CSME) 70% | | |
| 8. small cell lung carcinoma 85% | | |
| 9. visually significant cataract 85% | | |
| 10. visually significant cataract 65% | | |
| 11. visually significant cataract 85% | | |

TABLE 7-continued

Data on endothelial cell inhibitory activity in plasma from 21 other adult patients (>40 yrs old) with longer term observational follow up, ~10 yrs. To test for the ability of inhibitory activity in the plasma fraction containing IgG, where inhibitory is defined as <=90%, to detect the presence of a previously unexpected significant medical condition. Known conditions associated with endothelial cell antibodies or inhibitory activity include: cancer, proliferative diabetic retinopathy, and certain auto-immune diseases.

12. visually significant cataract 80%
13. visually significant cataract 85%

CSME—clinically significant macular edema
PPN—negative predictive value = 3/(3 + 0) = 100%
PPV—positive predictive value = 13/(13 + 5) = 72%

The presence of plasma endothelial cell inhibitory activity preceded the diagnosis of fatal cancer by an average of 6-7 yrs in two patients with bladder or TCC, and by 1-2 yrs in one patient with fatal small cell lung cancer. Age-related macular degeneration or visually significant cataract requiring surgery are previously unrecognized important opthalmologic conditions associated with plasma inhibitory activity in 6 of 13 patients. The remaining patients, 4 of 13, had laser photocoagulation to treat clinically significant macular edema. More than one condition could coexist in the same patient, e.g. ARMD & treated cancer.

The sensitivity of the methods of the present invention was shown to be 100% for a positive test for inhibitory endothelial cell antibodies, and; the specificity was 37%, where a 'false-positive' test was defined as a positive test in a patient already having a condition known to be associated with endothelial cell autoantibodies (e.g. proliferative diabetic retinopathy in type 1 diabetes, or known breast cancer) (Table 7).

The predictive value of a negative test was 100%, and the predictive value of a positive test (PPV), i.e. its ability to disclose previously unsuspected important medical conditions was 72% (Table 7).

Optimally, information regarding a patient's family history, e.g. a history of pathologies such as cancer, and consideration of risk factors, such as smoking, is obtained to enhance the specificity of the methods of the present invention, to detect the presence of endothelial cell autoantibodies,

EXAMPLE 9

Biochemical, Physical and Chemical Characteristics of Plasma Protein-A Eluate

This example summarizes the biochemical, physical and chemical characteristics of plasma protein-A eluate fractions consistent with the active component being an autoantibody or antibody fragment.

The results demonstrate that 100% of inhibitory activity in plasma protein-A eluates from 5 of 5 diabetic subjects was retained after dialysis using 30 kD MW cutoff membranes. This suggests that the active component in the protein A eluates has a MW>30 kD.

The results further show that 23-58%, mean 44% of activity in 3 of 3 diabetic patient protein-A eluates survived heating at 95 deg C. for 5 mins.

In addition, 3-50%, mean 22%, of activity in 4 of 4 diabetic patient protein-A eluates was lost after exposure to reducing agents, 6 mM dithiothreitol ×2 hrs at room temperature indicating that the structure of the active component is stabilized in part through disulfide bonds.

Figure 15:
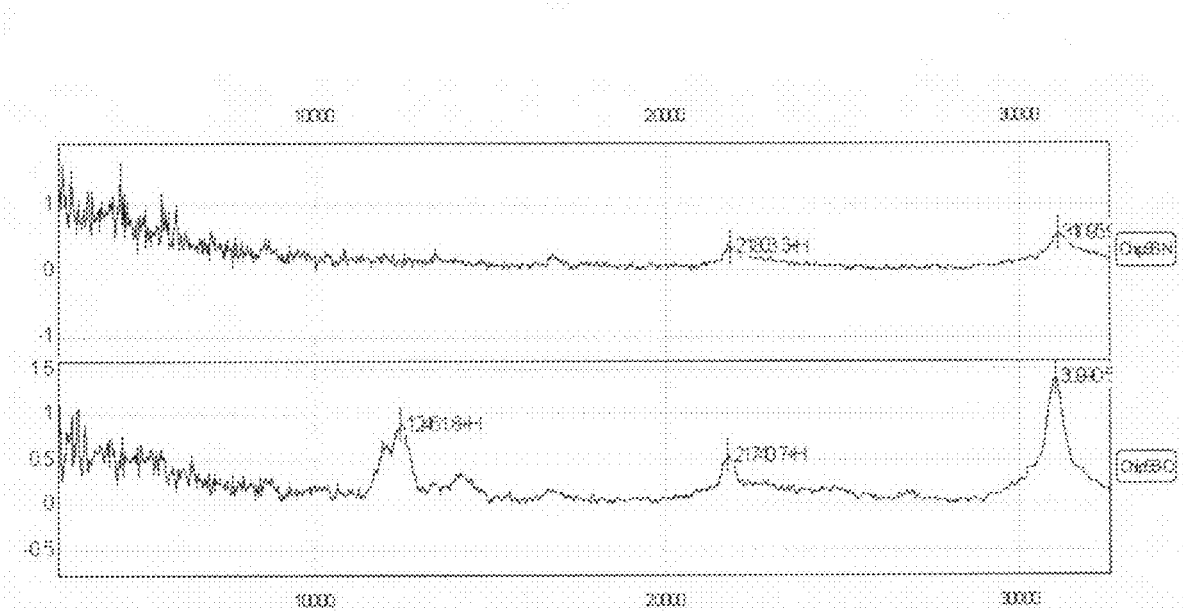
FIG. 15 shows graphs illustrating data generated by mass spectrometry of protein A-eluate fractions from diabetic or prostate cancer plasma that showed potent inhibitory activity in endothelial cells and anti-neurotrophic activity: Graph 1, cancer patient 1; Graph 2, cancer patient 2, as described in Example 9, infra.
Figure 16:
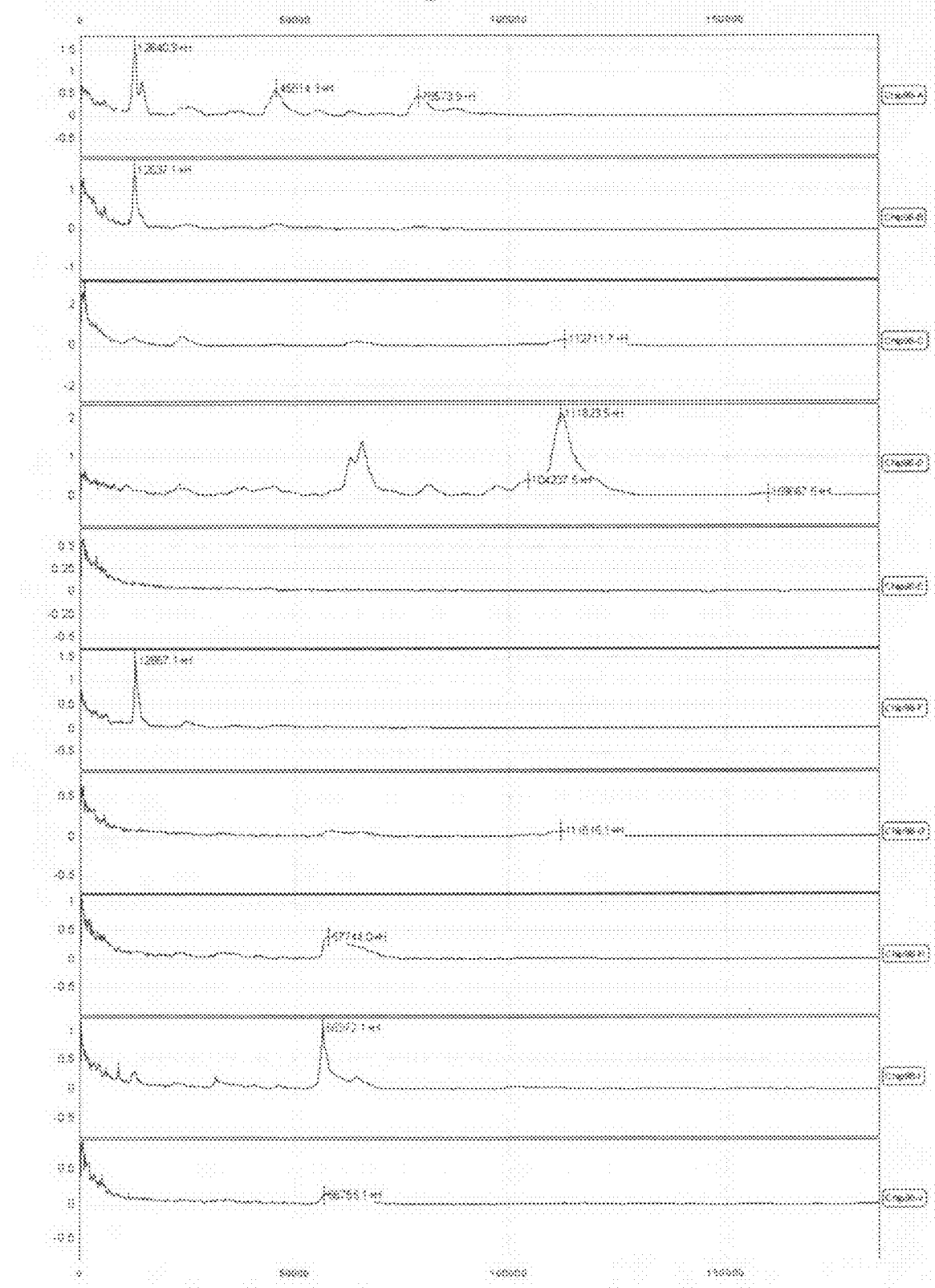
FIG. 16 shows graphs illustrating data generated by mass spectrometry of protein A-eluate fractions from diabetic or prostate cancer plasma that showed potent inhibitory activity in endothelial cells and anti-neurotrophic activity: Graphs 1-9: cancer patient 1, cancer patient 2, diabetic patient 2, albumin and IgG standards, blank, cancer patient 2, diabetic patient 2, cancer patient 2, diabetic patient 2, as described in Example 9, infra. This shows that diabetic plasma and prostate cancer serum produces roughly identical components of IgG, heavy chains, light chains and intact IgG-which may all contain inhibitory activity in endothelial cells.

Mass spectrometry of individual active inhibitory diabetic protein-A eluate fractions demonstrated MWs corresponding to IgG heavy chain dimers (101 kD), heavy chain monomers (56 kD), and possibly a heavy chain monomer fragment (31 kD) (FIGS. 7, 15 and 16). These data are consistent with the unusual stability data indicating that the active component may be stabilized in part through disulfide bonds, i.e. some of it exists as dimers of IgG. Moreover, substantial activity is still retained after either strong heating or treatment with reducing agents, implying that IgG monomers or fragments of IgG monomers contain inhibitory activity in endothelial cells.

Figure 6:
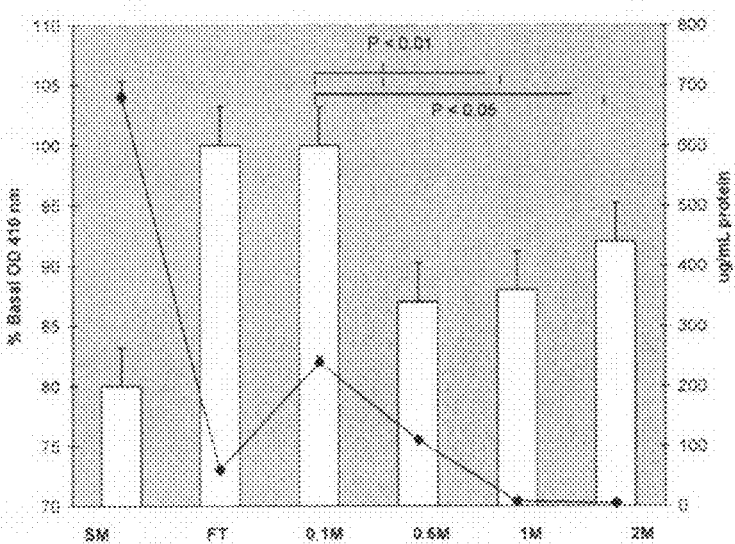
FIG. 6 shows three charts illustrating Heparin Sepharose chromatography of protein-A-eluated fractions from representative diabetic plasma with macular edema (A), proliferative (B) or no retinopathy (C). One fiftieth dilutions of starting material (SM), flow-through (FT), and 0.1, 0.5, 1, and 2M NaCL eluate fractions were assayed as described in Examples 4 and 9, infra.
Figure 6:
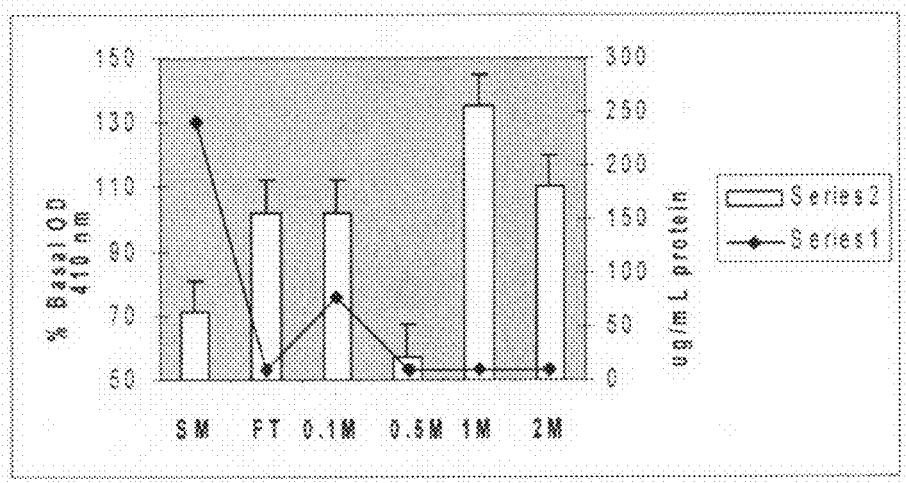
Figure 6:
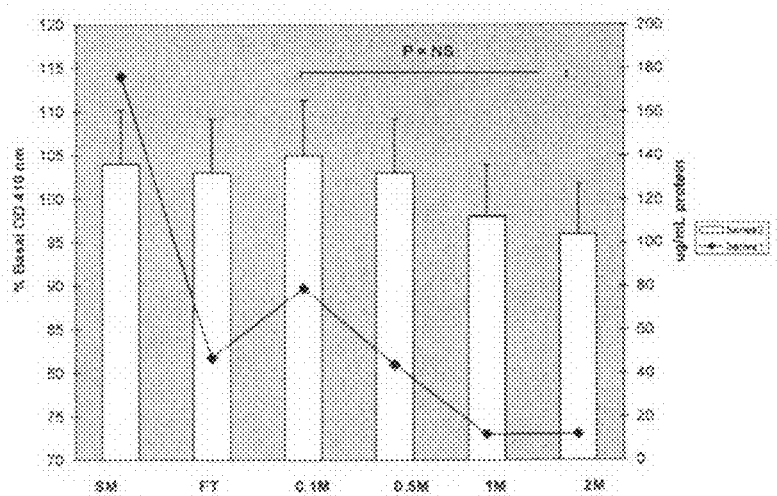
Figure 11:
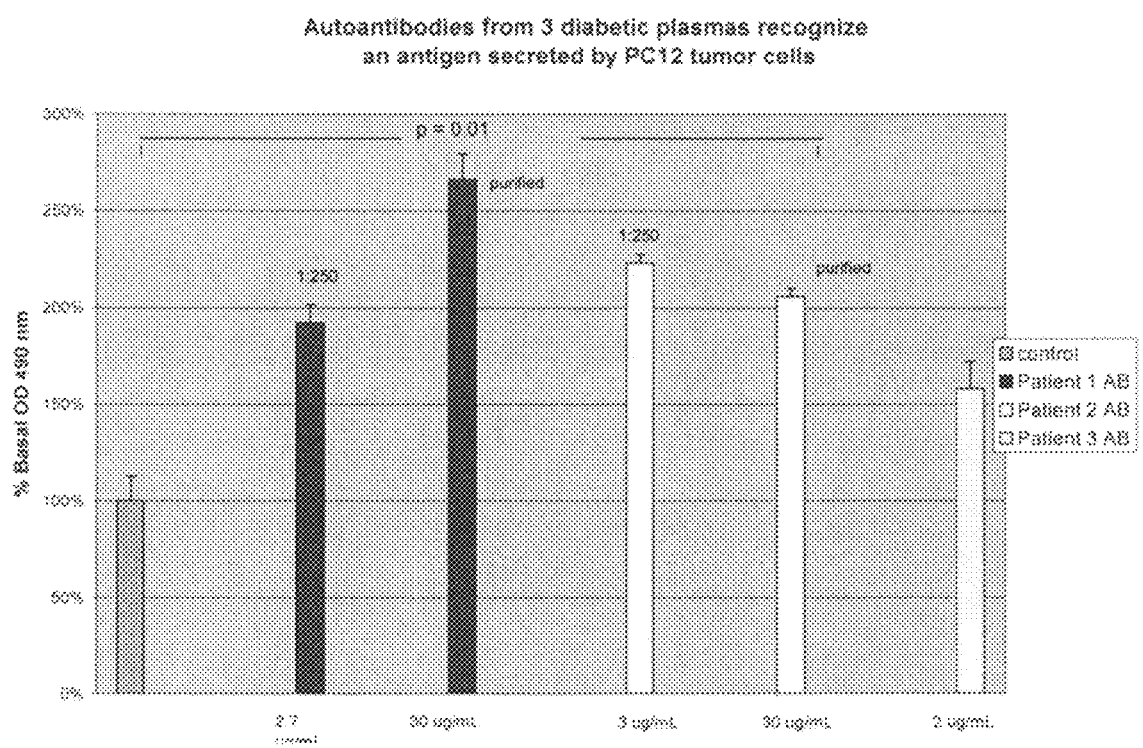
FIG. 11 shows a chart illustrating active inhibitory protein-A eluate fractions and heparin Sepharose purified fractions (purified) from 3 diabetic patients exhibited significant binding above background levels in an ELISA using DEAE-purified secreted material from PC12 cell conditioned medium (i.e. heparan sulfate proteoglycan) as the solid phase antigen, as described in Example 9, infra.
Figure 12:
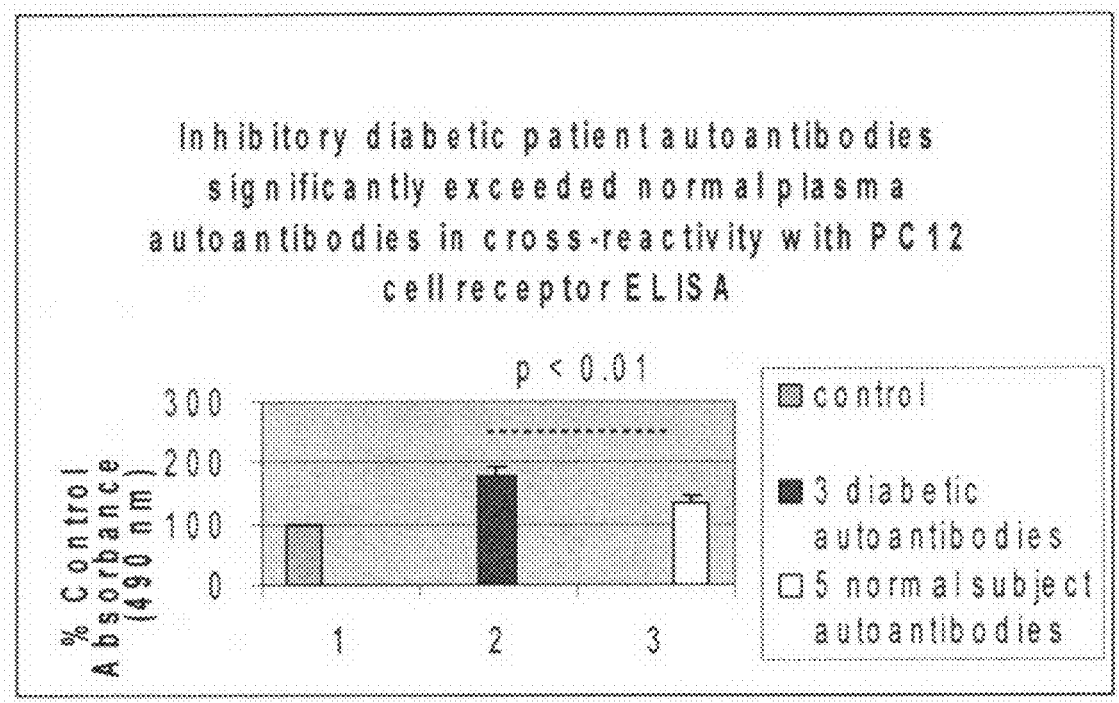
FIG. 12 shows a chart illustrating the comparison of cross-reactivity with heparan sulfate proteoglycan antigen purified from PC12 cell conditioned medium in protein-A eluate fractions from 3 active inhibitory diabetic plasma samples versus 5 normal plasma protein A eluates, as described in Example 6, infra. Control signifies no added protein-A eluate fraction.
Figure 13:
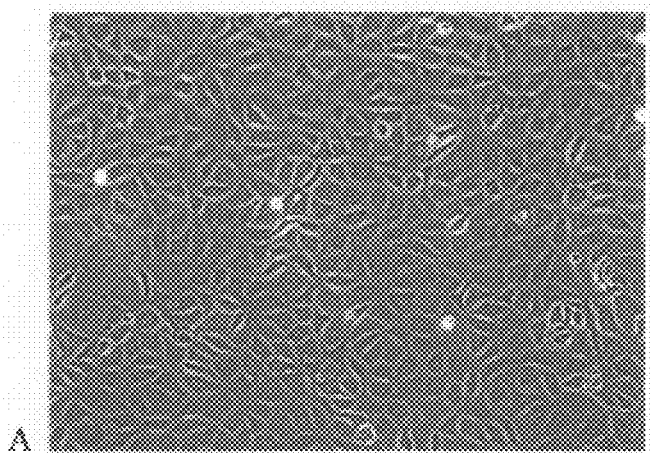
FIG. 13 shows three photographs illustrating endothelial cell apoptosis in cells exposed for 24 hrs to protein A eluate fractions from: A) Diabetic control patient 1; or B) diabetic patient 3; and C) diabetic patient 3. In C) staining with Hoechst 33342 dye confirms nuclear chromatin condensation seen in apoptosis, as described in Example 1, infra.
Figure 13:
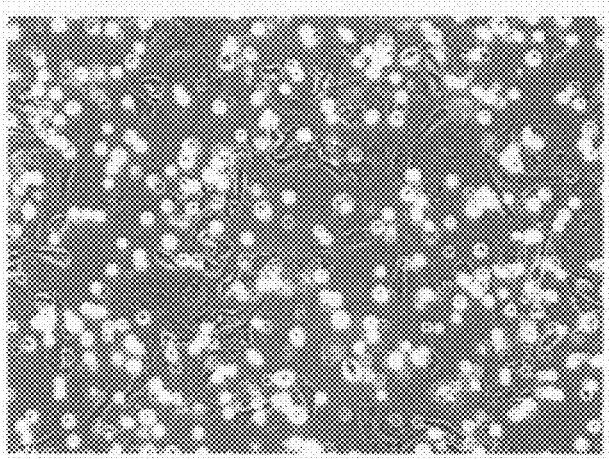
Figure 13:
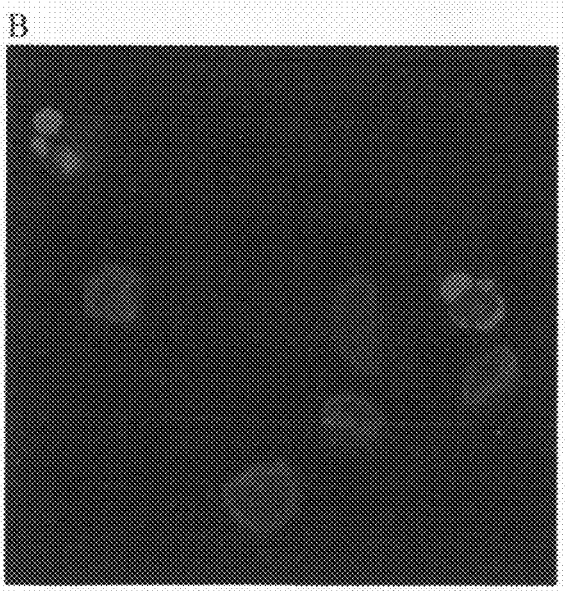

Results further show that the active inhibitory component in protein-A eluates has increased affinity for heparin sepharose columns (see Table 6, and FIG. 6). The active inhibitory diabetic plasma protein A eluate fractions bound in an ELISA assay to highly purified components of endothelial cell or PC12 cell that were subjected to a purification scheme shown to isolate heparan sulfate proteoglycan components of the cell membrane (e.g., Heparan sulfate proteoglycan components of endothelial cells) (FIG. 11).

The significance of the finding that the antibodies had affinity for heparin or heparan sulfate proteoglycan is that they would be likely to interact in vivo with vascular surfaces on the heart, blood vessels and in the microcirculation of organs to cause dysfunction.

Taken together these results establish that the active inhibitory component in the protein-A eluates is an auto antibody or auto antibody fragment.

EXAMPLE 10

The data herein shows that plasma bFGF immunoreactivity (IR) can predict the need for laser treatment for diabetic retinopathy in a baseline subset of advanced type 2 diabetes. These and our prior examples suggest that low plasma bFGF: immunoreactivity may be a marker for the presence of anti-endothelial cell autoantibodies which may contribute to the need for laser photocoagulation treatment in patients with advanced type 2 diabetes.

In the present study we tested for an association between baseline plasma bFGF and post-baseline laser photocoagulation occurrence in adults with long-standing type 2 diabetes from the Veterans Affairs Diabetes Trial.

These results suggest that low plasma bFGF-IR may be a novel risk marker for vision-threatening retinal pathology in older adult male patients with advanced type 2 diabetes.

Methods

This study includes 172 diabetic subjects.

EDTA plasma was drawn in the morning after an overnight fast at each site. Plasma was aliquoted and shipped frozen (dry ice) to a central laboratory (Maveric, Boston Veterans Affairs Medical Center (VAMC), Boston, Mass.) where it was inventoried and stored at −80 C for 1-2 yrs. Archived, coded frozen EDTA plasma from consecutively enrolled patients was shipped to the laboratory of Dr. Zimering (VA New Jersey Health Care System, Lyons, N.J.) where bFGF-IR assays were performed. All other assays were performed in the Central Laboratory of the VADT (Tufts University, Boston, Mass.).

Baseline clinical characteristics are shown in Table 1. All subjects were >40 yrs old. Ninety-seven percent of patients were men.

Medications

All patients were taking anti-diabetic medications at baseline including oral agents and/or insulin. Patients randomized to the standard or intensive glycemic treatment group were treated for at least 5 yrs (and some up to 7 yrs) with the same classes of medications including the TZD rosiglitazone.

Baseline anti-hypertensive medication use included ACE inhibitors in 67% of patients and angiotensin receptor blockers in an additional 7% of patients indicative of a high proportion of patients with a history of persistent micro-albuminuria.

Laser Photocoagulation

Information regarding laser photocoagulation for retinopathy was obtained from questionnaires administered at the baseline and each annual visit. Baseline determination of plasma bFGF-IR (at VANJ) was masked to the information about laser photocoagulation occurrence.

The risk factors associated with time to first laser treatment were modeled in 156 subjects in whom post-baseline data about laser occurrence was available between the $2^{nd}$ and 6th post-baseline annual visits. Laser events occurring during the $1^{st}$ yr of study follow up were censored to minimize the effect of detection bias on time to first laser occurrence.

Baseline Fundus Photographs

Baseline fundus photographs were obtained in all patients. The photographs were evaluated at the Central Fundus Photography Reading Center, University of Wisconsin, Madison, Wis. The frequencies of no retinopathy, microaneurysms, mild non-proliferative, severe non-proliferative and proliferative retinopathy were 29%, 18%, 29%, 17% and 7% respectively. Macular edema was present in 16 of 156 patients (10.3%) in whom it could be assessed from photographs.

Laboratory and Clinical Measures

Urinary microalbumin, plasma $HbA_1c$ and urine creatinine were determined by standard methods as previously described (12). Urinary albumin/creatinine ratio was calculated as albumin concentration/creatinine concentration ×100. Plasma total cholesterol, triglycerides and HDL cholesterol were determined by standardized direct enzymatic assay methods as previously reported (12). LDL cholesterol was calculated using the Friedenwald equation on all samples with plasma triglyceride concentration <400 mg/dL. Blood pressure (BP) was recorded in the seated position after five-minute rest. Three consecutive readings were obtained, and the median value of the three consecutive determinations was used for analysis.

Plasma Samples

Archived, coded EDTA plasma samples were kept frozen (−40 C) for 1-2 years prior to assay for bFGF-IR. Plasma bFGF-IR and bFGF-like bioactivity were previously shown to be stable for 5 yrs or longer at −20 C, and for up to 3 freeze-thaw cycles (11).

Basic Fibroblast Growth Factor Assays

Basic FGF immunoreactivity (bFGF-IR) in plasma was determined using a sensitive specific two-site enzyme-linked immunoassay (R&D Systems, Inc. Minneapolis, Minn.).

The mean minimal detectable dose of FGF-2 was 0.5 pg/mL (n=9 assays). The method was linear between 0.5-64 pg/mL. The average correlation coefficient for the runs was 0.99. The intra-assay coefficients of variation for low and high dose calibration standards or human diabetic plasma samples were $\leq 8\%$; the inter-assay coefficient of variation(s) for patient samples or calibration standards ranged from 10-14%. Recovery of bFGF-IR in diluted (1:2) samples of normal human plasma ranged from 108-123%. The dilution curves of patient plasma samples were parallel to the standard curve. aFGF, FGF-4 (hst), FGF-5, FGF-6 did not cross-react in the assay. In prior studies that employed the same bFGF-IR assay method, mean serum bFGF-IR in 15 normal subjects (men and women, ranging from 39-74 yrs old) was 0.9 pg/mL (range 0-4 pg/mL) (13).

Plasma bFGF-IR in 43 healthy male blood donors, age 21-63 yrs, ranged from 0-4 pg/mL and there was no effect of age on plasma bFGF level (14).

Cut-Point for "Low" vs "High" bFGF-IR

We dichotomized around the value of 4.5 pg/mL, the previously reported upper limit in normal adult men (14).

Statistics

Basic FGF-IR values were not normally distributed. The Wilcoxon rank sum test was used for group comparisons of bFGF-IR (Table 2), and the correlations reported are Spearman correlation coefficients. Cox proportional hazards regression analysis was used to model baseline risk factors associated with time to first post-baseline laser treatment. Modeling was performed with a set of clinical risk variables (age, diabetes duration, low vs high bFGF, history of hypertension, LDL cholesterol concentration, baseline $HbA_1c$) which was based upon published literature (15, 16) and are known or likely to be associated with retinopathy or laser treatment. Backward elimination was used to obtain the best fit model using an alpha level of $\leq 0.05$ as the cutoff for variable inclusion in the final model. Excluded variables with p values >0.20 included: age, history of hypertension, baseline $HbA_1c$, insulin use, ACE inhibitor use, ARB use. Other excluded variables (LDL cholesterol concentration, glycemic treatment arm (standard or intensive), and duration of diabetes) had p values=0.06.

Protein-A Affinity Chromatography

Protein-A affinity chromatography was carried out as previously described (17). Four-tenths mL aliquots of plasma were adjusted to pH 8.0 by adding 0.8 mL 100 mmol/L Tris (pH 8). After syringe filtration to clarify samples, 1 mL was applied to a 1-mL column of packed protein-A beads (Pierce Chemical Co., Rockford, Ill.) equilibrated in 100 mmol/L Tris, pH 8.0. The column was washed and eluted as previously described (17). The eluate fractions containing nearly all the recovered protein were pH neutralized and stored at 0-4 C. Inhibitory activity in protein-A eluate fractions was unchanged, appearing in the retentate fraction after dialysis (10 mmol/L phosphate, pH 7.4) and ultrafiltration on a 10 kD cutoff membrane (Centricon-10; Millipore Corp., Bedford, Mass.). All fractions were sterile filtered (Millipore Corp. Bedford, Mass.; 0.2 um) before assay for growth-promoting activity.

Cell Culture and Growth Assays

Bovine pulmonary artery (BPA) endothelial cells (Clonetics, Inc. San Diego, Calif.) were maintained at 37 C in 5% $CO_2$/95% air in endothelial cell growth medium (EGM, Clonetics, Inc., San Diego, Calif.) plus 10% fetal bovine serum. BPA cells were passaged continuously and used between passages 4-10.

Colorimetric Estimation of Endothelial Cell Number

Colorimetric estimation of cell number was carried out as previously reported (17). Confluent cells were trypsinized and plated at $10^3$-$10^4$ cells/well in Medium 199 plus 10% fetal calf serum in 96-well plates. After up to four days incubation for cells to reach 60-80% confluency, test fractions (1:50 dilution of protein A eluates of plasma) were added to wells in quadruplicate. After two days incubation in the presence of test fractions, cells were washed with PBS and processed for the colorimetric estimation of cell number, i.e. cell-associated acid phosphatase activity, as previously described (17). There was a linear relationship between endothelial cell number and optical density at 410 nm as previously described (17). Growth-promoting activity is expressed as a percentage of the control cell number for cells grown in the absence of test protein-A eluate fractions. Each point represents the mean of quadruplicate determinations. The intra- and inter-assay coefficients of variation were 4% and 7% at 1:50 dilution of protein-A-eluted fractions from plasma of three diabetic subjects (n=3 assays in each patient).

Heparin Sepharose Affinity Chromatography

Heparin affinity chromatography was performed on protein-A eluates from diabetic plasma that had been adjusted to pH 7.4 as previously described (18). After applying the protein-A eluate (starting material, SM), the column was washed extensively with starting buffer containing 10 mM phosphate, 0 M NaCL, pH 7.4 and then eluted stepwise with 2 column volumes each of 0.1M, 0.5M, 1M and 2M NaCL. The flow through (FT) and eluate fractions were assayed in quadruplicate for growth promotion in endothelial cells.

Results

The present data suggests a novel association between low baseline plasma bFGF-IR and the need for first laser photocoagulation in patients with long-standing type 2 diabetes. The increased requirement for laser treatment in patients with low baseline plasma bFGF persisted for up to 5 yrs after initiation of study treatment in spite of the known strong influence of duration of diabetes (Table 4). Low plasma bFGF was still significantly associated with the need for laser treatment after adjusting for standard vs intensive glycemic treatment arm and for anti-hypertensive medications (ACE inhibitors, ARBs) shown to lower bFGF (11) and possibly slow the progression of retinopathy (19-21). Our data are consistent with the possibility that low plasma bFGF may signify the presence of an additional risk factor or factors, e.g. autoantibodies inhibitory in endothelial cells, which may contribute to the need for laser treatment.

Relation of bFGF-IR to Baseline Characteristics

There was no association between plasma bFGF-IR and either patient age, BMI, diabetes duration, systolic blood pressure, urine albumin creatinine ratio or serum LDL cholesterol concentration (Table 2). There was a marginal (p=0.07) inverse association between plasma bFGF-IR and baseline glycosylated hemoglobin (HbA$_1$c) (Table 2). There was a significant association between plasma bFGF and waist-hip ratio (p=0.003, Table 2). High plasma bFGF was significantly associated with baseline thiazide diuretic use (p=0.01; Table 3). There was no significant association between low bFGF and any other categorical risk factor shown in Table 3 including various classes of anti-diabetic or anti-hypertensive medication use.

Time to First Laser Occurrence

Over 4 years of study treatment, first laser treatment was significantly more likely to be required in patients with low compared to high baseline bFGF (19% vs 6%, p=0.03 for the difference, Table 4). Extending the possible follow-up time to 5 years, first laser treatment was marginally significantly more likely to be needed in patients with low compared to high baseline bFGF (21% vs 8%, p=0.055, Table 4). The best fit model of risk factors associated with the time to first laser treatment during four years of follow-up included as significant predictors: bFGF (low vs high) (hazard ratio, HR 5.01; p=0.012), duration of diabetes (HR 1.05; p=0.050), and LDL cholesterol concentration (HR 0.98; p=0.027) (Table 5). The same variables, bFGF (low vs high) (HR 3.49; p=0.016), duration of diabetes (HR 1.06; p=0.009), LDL cholesterol concentration (HR 0.98; p=0.023) (Table 5) also were significantly associated with time to first laser after up to 5 years of study treatment. In Cox proportional hazards regression models that adjusted for diabetes treatment group, ACE inhibitor, ARB use, or insulin treatment, bFGF (low vs high) (HR 4.08; p=0.025) was the only variable significantly associated with time to first laser after 4 years of study treatment.

Lack of Association Between Plasma bFGF and Baseline Retinopathy Stage

There was no significant association between low baseline bFGF and baseline retinopathy stage or the baseline presence or absence of macular edema (Table 6). In Cox proportional hazards regression models that adjusted for baseline indicators for laser treatment, proliferative retinopathy (HR 29.11; p=0.0002) and macular edema (HR 8.17; p=0.0036), but not basic FGF (low vs high) (HR 3.44; p=0.10) were significantly associated with time to first laser treatment.

Figure 20:
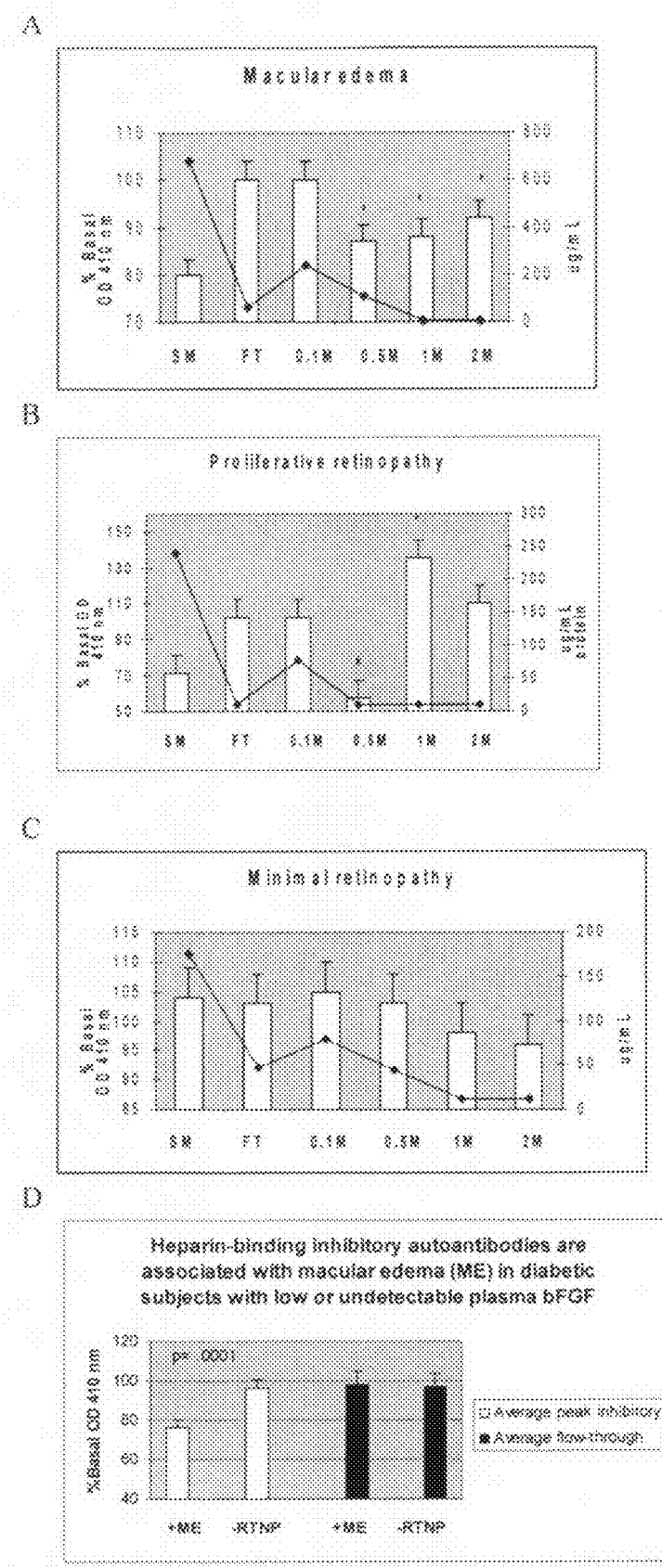
FIG. 20 shows Heparin Sepharose affinity chromatography of protein-A eluate fractions from plasma of representative diabetic subjects with (A) macular edema, (B) proliferative retinopathy, (C) minimal or no retinopathy. D) Average results in twelve patients with low or undetectable plasma bFGF: six with macular edema (ME) A) or six with minimal retinopathy (-RTNP) C). Heparin Sepharose (HS) chromatography was carried out as described in Methods. Growth-promoting activity was assessed as change in cell number as described in Methods. Peak inhibitory activity represents results (percent basal $OD_{410}$) with the fraction eluting from HS showing most inhibitory activity on the growth of endothelial cells (e.g. 0.5M, FIG. 1A). Flow-through activity represents results with the fraction not retained on the HS column (e.g. FT).

Endothelial Cell Inhibitory Auto-antibodies in Plasma from Low or Undetectable bFGF We compared inhibitory bioactivity in endothelial cells in a $\frac{1}{50}^{th}$ dilution of the protein-A eluate fraction from plasma of diabetic subjects with macular edema or those without significant retinopathy who did not differ significantly in their baseline clinical characteristics (Table 7). Average inhibitory growth promoting activity in the protein-A eluates from diabetic maculopathy plasmas (n=7) (72±20%) significantly exceeded average growth promoting activity in the protein-A eluates from plasma of diabetic subjects with no or minimal retinopathy (n=7) (101±8%; p=0.004 for the difference) (Table 7). The protein-A eluates from plasma were subjected to heparin Sepharose (HS) affinity chromatography. In the protein-A eluate of plasma from a representative diabetic patient with macular edema, activity significantly inhibitory in endothelial cells eluted at 0.5M, 1M and/or 2M NaCL from a HS column (e.g. FIG. 20a). Average peak inhibitory endothelial cell activity in the protein-A eluates of plasma from diabetic macular edema (n=6) significantly exceeded average peak inhibitory activity in the protein-A eluates of plasma from diabetics with no or minimal retinopathy (n=6; p=0.0001, FIG. 20d). There was no difference in the average flow-through activity from HS columns in protein-A eluates from diabetic subjects with macular edema or those without retinopathy (FIG. 20d). The protein-A eluate of plasma from a diabetic subject with proliferative retinopathy displayed significant inhibitory activity eluting at 0.5M NaCL, and significant stimulatory activity in endothelial cells eluting at 1M NaCL from a HS column (FIG. 20b).

Discussion

Diabetic macular edema is the leading cause of visual impairment in type 2 diabetes (1). It may go unrecognized for substantial periods in type 2 diabetes (39). Proliferative diabetic retinopathy requires immediate intervention as it is associated with a high risk for visual loss.

In summary, we have provided evidence that low baseline plasma bFGF, although not a specific marker, may yet indicate the presence of heparin-binding, endothelial cell inhibitory autoantibodies in plasma from adults with advanced, poorly-controlled type 2 diabetes.

TABLE 1

Baseline characteristics in study subjects

|  | Mean ± SD |
|---|---|
| Age (yrs) | 59.2 ± 8.4 |
| BMI (kg/m2) | 31.4 ± 4.7 |
| Diab Duration (yrs) | 11.4 ± 8.1 |
| HbA$_1$c (%) | 9.5 ± 1.4 |
| Systolic BP (mmHg) | 130.2 ± 17.9 |
| Diastolic BP (mmHg) | 74.2 ± 10.8 |
| ACR (mg/g) | 151 ± 491 |
| LDL cholesterol (mg/dL) | 104 ± 32 |

BP—blood pressure;
ACR—urine albumin/creatinine ratio;
LDL—low density lipoprotein

TABLE 2

Correlations of baseline risk factors with plasma bFGF-IR

|  | Spearman Correlation Coefficient | p-value |
|---|---|---|
| Age | 0.04 | 0.61 |
| Body mass index | −0.04 | 0.63 |
| Diabetes duration | −0.01 | 0.86 |
| Systolic Blood pressure | −0.01 | 0.87 |
| HbA$_1$c | −0.14 | 0.07 |
| LDL cholesterol | −0.08 | 0.34 |
| Albumin/creatinine ratio | 0.01 | 0.88 |
| Waist-hip ratio | 0.23 | 0.003 |

LDL—low density lipoprotein

TABLE 3

Associations between low vs high bFGF and baseline categorical risk factors

| Variable | bFGF ≦ 14.4 | bFGF ≧ 4.5 | p-value* |
|---|---|---|---|
| Demographics | | | |
| Male | 97.8 | 96.3 | 0.58 |
| Hispanic | 13.3 | 22.0 | 0.14 |
| Non-Hispanic white | 62.2 | 63.4 | 0.87 |
| African-American | 23.3 | 13.4 | 0.10 |
| Current smoker | 15.6 | 19.5 | 0.49 |
| Baseline medications | | | |
| Beta blocker | 13.3 | 8.5 | 0.32 |
| ACE inhibitor | 68.9 | 67.1 | 0.80 |
| Angiotensin receptor blocker | 8.9 | 4.9 | 0.30 |
| Calcium channel antagonist | 22.2 | 18.3 | 0.52 |
| Thiazide diuretic | 10.0 | 25.6 | 0.01 |
| Statin | 66.7 | 61.0 | 0.44 |
| Fibrate | 14.4 | 23.2 | 0.14 |
| Thiazolidinedione | 22.2 | 18.3 | 0.52 |
| Insulin | 46.7 | 46.3 | 0.97 |
| Sulfonylurea | 64.4 | 63.4 | 0.89 |
| Metformin | 76.7 | 75.6 | 0.87 |
| Thyroid hormone | 6.7 | 6.1 | 0.88 |
| History | | | |
| Hypertension | 68.2 | 77.2 | 0.19 |
| Myocardial infarction | 10.23 | 16.5 | 0.23 |
| Coronary revascularization | 23.3 | 13.4 | 0.10 |
| Any macrovascular event (MI, CABG, angina, stroke, PVD) | 40.9 | 34.2 | 0.37 |
| Albuminuria (U alb/creat ratio) | | | |
| Macro ≧300 mg/g | 9.2 | 10.1 | 0.89 |
| Micro 30-299 mg/g | 26.4 | 29.1 | |
| Normo <30 mg/g | 64.4 | 60.8 | |

Results are % of patients
*p-values from Chi-square Test

TABLE 4

Cumulative first laser treatment for low and high bFGF group.

| Maximum yrs of follow-up | Total first laser event low bFGF | Total first laser event high bFGF | p-value^ |
|---|---|---|---|
| 4 | 16 (19) | 4 (6) | 0.03 |
| 5 | 18 (21) | 6 (8) | 0.055 |
| 6 | 18 (21) | 7 (10) | 0.056 |

Results are number, (%) of patients affected
^Log-rank test

TABLE 5

Cox proportional hazard regression models of time to first laser occurrence

| Variable | HR | 95% CI | p-value |
|---|---|---|---|
| 4 yrs post-baseline | | | |
| Plasma bFGF-IR (low vs high) | 5.01 | 1.43-17.46 | 0.012 |
| Diabetes duration | 1.05 | 1.00-2.72 | 0.050 |
| LDL cholesterol | 0.98 | 0.97-1.00 | 0.027 |
| 5 yrs post-baseline | | | |
| Plasma bFGF-IR (low vs high) | 3.49 | 1.26-9.58 | 0.016 |
| Diabetes duration | 1.06 | 1.01-1.10 | 0.009 |
| LDL cholesterol | 0.98 | 0.97-1.00 | 0.023 | n = 156 subjects;
HR—hazard ratio,
CI—confidence intervals

Results nearly identical to those after 5 years of follow-up were obtained after extending the possible follow-up time to 6 years

TABLE 6

Association between bFGF and baseline ophthalmologic results in 172 patients.

| Variable | bFGF ≦ 4.4 | bFGF ≧ 4.5 | p-value* |
|---|---|---|---|
| No or minimal retinopathy | 35 | 38 | 0.78 |
| Mild-moderate retinopathy | 24 | 22 | 0.87 |
| Severe nonproliferative retinopathy | 14 | 12 | 0.94 |
| Macular edema | 11 | 5 | 0.19 |
| Proliferative retinopathy | 7 | 4 | 0.47 |

Result are number of affected subjects
*p-value from T-test

TABLE 7

Baseline characteristics in 14 representative subjects with macular edema or no retinopathy with low or undetectable plasma bFGF

| Subject group | Age (yr) | Duration of diabetes (yr) | HbA1c (%) | ACR (mg/g) | bFGF (pg/mL) | Growth Activity (%)* |
|---|---|---|---|---|---|---|
| Macular edema (n = 7) | 64 ± 5 | 13 ± 4 | 8.3 ± 1.4 | 322 ± 381 | 0 ± 0 | 72 ± 20 |

TABLE 7-continued

Baseline characteristics in 14 representative subjects with macular edema or no retinopathy with low or undetectable plasma bFGF

| Growth Subject group | Age (yr) | Duration of diabetes (yr) | HbA1c (%) | ACR (mg/g) | bFGF (pg/mL) | Activity (%)* |
|---|---|---|---|---|---|---|
| No retinopathy (n = 7) | 59 ± 11 | 8 ± 6 | 9.7 ± 1.2 | 45 ± 49 | 0.7 ± 1.3 | 101 ± 8 |
| p-value | 0.27 | 0.11 | 0.08 | 0.08 | 0.16 | 0.004 |

*represents percent basal endothelial cell number after 48 hrs incubation with a 1/50$^{th}$ dilution (30 ug/mL) of the protein-A eluate fraction from plasma.
ACR-albumin/creatinine ratio
p-value from T-tests.

References in Example 10
1. Girach A, Lund-Andersen H., 2007. Diabetic macular oedema: a clinical overview. *Int J Clin Pract.* 61(1), 88-97.
2. Aroca P R, Salvat M, Fernandez J, Mendez I., 2004, Risk factor for diffuse and focal macular edema, J Diabetes Complications., 18(4), 211-215.
3. Grant M B, Afzal A, Spoerri P, Pan H, Shaw L C, Mames R N., 2004, The role of growth factors in the pathogenesis of diabetic retinopathy. *Expert Opin Investig Drugs.* (10), 1275-1279.
4. Aiello L P, Wong J S., 2000, Role of vascular endothelial growth factor in diabetic vascular complications. *Kidney Int Suppl* 77:S113-119.
5. Nguyen Q D, Tatlipinar S, Shah S M, Haller J A, Quinlan E, Sung J, Zimmer-Galler I, Do D V, Campochiaro P A., 2006, Vascular endothelial growth factor is a critical stimulus for diabetic macular edema. Am J Opthalmol. 142(6), 961-969.
6. Boulton M, Gregor Z, McLeod D, Charteris D, Jarvis-Evans J, Moriarty P, Khaliq A, Foreman D, Allamby D, Bardsley B., 1997, Intravitreal growth factors in proliferative diabetic retinopathy: correlation with neovascular activity and glycaemic management. Br J Opthalmol, 81(3), 228-233.
7. Gospodarowicz D., Ferrara N., Schweigerer L., Neufeld G., 1987. Structural characterization and biological functions of fibroblast growth factor. Endocr Rev. 8, 95-114.
8. Schweigerer L., Neufeld G., Friedman J., Abraham J. A., Fiddes J. C., Gospodarowicz D., 1987. Capillary endothelial cells express basic fibroblast growth factor, a mitogen that promotes their own growth. Nature. 325, 257-259.
9. Folkman J., Klagsbrun M., 1987. Angiogenic factors. Science 235, 442-447.
10. Esch F., Baird A., Ling N., Ueno N., Hill F. Denoroy L. Klepper R., Gospodarowicz D., Bohlen P., Guillemin R., 1985. Primary structure of bovine pituitary basic fibroblast growth factor (FGF) and comparison with the amino-terminal sequence of bovine brain acidic FGF. Proc Nat Acad Sci (USA) 19, 6507-6511.
11. Zimering M. B., Eng J., 1996. Increased basic fibroblast growth factor-like substance in plasma from a subset of middle-aged or elderly male diabetic patients with microalbuminuria or proteinuria. J Clin Endo Metab. 81, 4446-4452.
12. Abraira C., Duckworth W., McCarren M., Emanuele N., Arca D., Reda D., Henderson W., 2003. Design of the cooperative study of glycemic control and complications in diabetes mellitus type 2. J Diab & Compl. 17, 314-322.
13. Zimering M. B., 2002. Effect of intravenous bisphosphonates on release of basic fibroblast growth factor in serum of patients with cancer-associated hypercalcemia. Life Sciences, 70, 1-14.
14. Larsson A., Skoldenberg E., Ericson H., 2002. Serum and plasma levels of FGF-2 and VEGF in healthy blood donors. Angiogenesis 5, 107-110.
15. Higgins G. T., Khan J., Pearce I. A., 2007, Glycaemic control and control of risk factors in diabetes patients in an opthalmology clinic: what lessons have we learned from the UKPDS and DCCT studies? *Acta Opthalmol Scand.* 85(7), 772-776.
16. Miljanovic B., Glynn R. J. Nathan D. M., Manson J. E. Schaumberg D. A. 2004 A prospective study of serum lipids and risk of diabetic macular edema in type 1 diabetes. Diabetes. 53(11), 2883-2892.
17. Zimering, M B, Thakker-Varia, S. 2002. Increased fibroblast growth factor-like autoantibodies in serum from a subset of patients with cancer-associated hypercalcemia. Life Sciences, 71: 2939-2959.
18. Zimering M B, Brandi M L, deGrange D A, Marx S J, Streeten E Katsumata N, Murphy P R, Sato Y, Friesen H G, Aurbach G D. Circulating fibroblast growth factor-like substance in familial multiple endocrine neoplasia type 1. 1990. J Clin Endocrinol Metab. 70(1):149-154.
19. Chaturvedi N, Sjolie A K, Stephenson J M, Abrahamian H, Keipes M, Castellarin A, Rogulja-Pepeonik Z, Fuller J H, 1998, Effect of lisinopril on progression of retinopathy in normotensive people with type 1 diabetes. The EUCLID Study Group. EURODIAB Controlled Trial of Lisinopril in Insulin-Dependent Diabetes Mellitus. *Lancet.* 351(9095), 28-31.
20. Sjølie A K. 2007, Prospects for angiotensin receptor blockers in diabetic retinopathy. *Diabetes Res Clin Pract.* 76 Suppl 1:S31-39.
21. Chaturvedi N, Fuller J H, Pokras F, Rottiers R, Papazoglou N, Aiello L P; *EUCLID Study Group.*, 2001, Circulating plasma vascular endothelial growth factor and microvascular complications of type 1 diabetes mellitus: the influence of ACE inhibition., Diabet Med (4), 288-294.
22. Shimada K, Baba T, Neugebauer S, Onozaki A, Yamada D, Midorikawa S, Sato W, Watanabe T., 2002, Plasma vascular endothelial growth factor in Japanese Type 2 diabetic patients with and without nephropathy. *J Diabetes Complications.* 16(6):386-390.
23. Cottone S, Vadalà A, Mangano M T, Riccobene R, Vella M C, Neri A L, Mulé G, Piazza G, Amato F, Zagarrigo C, Cerasola G. 2000. Endothelium-derived factors in microalbuminuric and nonmicroalbuminuric essential hypertensives. *Am J. Hypertens.* 13(2), 172-176.
24. Teichert-Kuliszewska K, Hamilton B S, Deitel M, Roncari D A. (1992) Augmented production of heparin-binding mitogenic proteins by preadipocytes from massively obese persons. *J Clin Invest.* 90(4):1226-1231
25. Lijnen P, Fagard R, Staessen J, Amery A. (1981). Effect of chronic diuretic treatment on the plasma renin-angiotensin-aldosterone system in essential hypertension. *Br J Clin Pharmacol.* 12(3), 387-392.
26. Keech A C, Mitchell P, Summanen P A, O'Day J. Davis T M, Moffitt M S, Taskinen M R, Simes R J, Tse D, Williamson E, Merrifield A. Laatikainen L T, d'Emden M C, Crimet D C, O'Connell R L, Colman P G; FIELD study investigators. 2007, Effect of fenofibrate on the need for laser treatment for diabetic retinopathy (FIELD study): a randomised controlled trial. Lancet. 370(9600), 1687-1697.
27. Dirix L. Y., Vermeulen P. B., Pawinski A., Prové A., Benoy I., De Pooter C., Martin M., Van Oosterom A. T., 1997. Elevated levels of the angiogenic cytokines basic fibroblast growth factor and vascular endothelial growth factor in sera of cancer patients. Br J. Cancer. 76(2), 238-243.
28. Zimering M B, Anderson R J, Ge L, Moritz T, Pardun J and the VADT Substudy Group. 2008. Association between endothelial cell inhibitory autoantibodies and laser treatment for retinopathy in a baseline subset from the Veterans Affairs Diabetes Trial., Endocrine Society OR50-4, 163.
29. Vlodavsky I, Miao H Q, Medalion B, Danagher P, Ron D., 1996. Involvement of heparan sulfate and related molecules in sequestration and growth promoting activity of fibroblast growth factor. Cancer Metastasis Rev, 15(2), 177-186.
30. Fillit H, Lahita R, 1991, Antibodies to vascular heparan sulfate proteoglycan in patients with systemic lupus erythematosus. *Autoimmunity.* 9(2), 159-164.
31. Fillit H. Mulvihill M., 1993. Association of autoimmunity to vascular heparan sulfate proteoglycan and vascular disease in the aged. *Gerontology.* 39(4), 177-182.
32. Reddi A S, Ramamurthi R, Miller M, Dhuper S, Lasker N. 1991, Enalapril improves albuminuria by preventing glomerular loss of heparan sulfate in diabetic rats. *Biochem Med Metab Biol.* 45(1), 119-131.
33. Jensen T. 1997, Pathogenesis of diabetic vascular disease: evidence for the role of reduced heparan sulfate proteoglycan. *Diabetes.* 46 Suppl 2:S98-100.
34. Deckert T, Feldt-Rasmussen B, Borch-Johnsen K, Jensen T, Kofoed-Enevoldsen A. 1989, Albuminuria reflects widespread vascular damage: the Steno hypothesis. Diabetologia. 32, 219-226.
35. Jones D B, Wallace R, Frier B M. 1992. Vascular endothelial cell antibodies in diabetic patients. Association with diabetic retinopathy. Diabetes Care. 15(4), 552-555.
36. Weiss A G, Chacko D M, Lane P H, Margalit E, Thompson A F, Mack-Shipman L R, Julie Stoner J A, Lane J T, Vascular endothelial growth factor, soluble vascular endothelial growth factor receptor-1, and progression of diabetic retinopathy in pregnant patients with type 1 diabetes. [P3-160] Endocrine Society, 2007.
37. Ferrara N, Henzel W J. 1989, Pituitary follicular cells secrete a novel heparin-binding growth factor specific for vascular endothelial cells. Biochem Biophys Res Commun. 161(2), 851-858.
38. Pepper M S, Ferrara N, Orci L, Montesano R. 1992, Potent synergism between vascular endothelial growth factor and basic fibroblast growth factor in the induction of angiogenesis in vitro. Biochem Biophys Res Commun. 189(2):824-831.
39. Hove M N, Kristensen J K, Lauritzen T, Bek T, 2004, The prevalence of retinopathy in an unselected population of type 2 diabetes patients from Arhus County, Denmark. Acta Opthalmol Scand. 82(4), 443-448.
40. Kempen J H, O'Colmain B J, Leske M C, Haffner S M, Klein R, Moss S E, Taylor H R Hamman R F, *Eye Diseases Prevalence Research Group.* 2004, The prevalence of diabetic retinopathy among adults in the United States. Arch Opthalmol. 122(4), 552-563.
41. Zhang L, Krzentowski G, Albert A, Lefebvre P J. 2001. Risk of developing retinopathy in Diabetes Control and Complications Trial type 1 diabetic patients with good or poor metabolic control. *Diabetes Care.* 24(7), 1275-1279.

EXAMPLE 11

We tested for an association between endothelial cell inhibitory auto-antibodies in plasma and the need for laser treatment. These results suggest that circulating auto-antibodies inhibitory in endothelial cells may contribute to the need for laser treatment in patients with advanced type 2 diabetes.

Methods

The study included 172 diabetic subjects.

Blood drawing was performed at each site in the morning in subjects who had fasted overnight. EDTA plasma was aliquoted and shipped frozen (dry ice) to a central laboratory (Maveric, Boston Veterans Affairs Medical Center (VAMC), Boston, Mass.) where it was inventoried and stored at −80 C for 1-2 yrs. Archived, coded frozen EDTA plasma from consecutively enrolled patients was shipped to the laboratory of Dr. Zimering (VA New Jersey Health Care System, Lyons, N.J.) where basic fibroblast growth factor immunoreactivity (bFGF-IR) and bioassays were performed. All other assays were performed in the Central Laboratory of the VADT (Tufts University, Boston, Mass.).

All subjects were >40 yrs old. Ninety-seven percent of patients were men. Baseline clinical characteristics in the subject group were previously reported (10) and are shown later in Table 4.

Medications

All patients were taking anti-diabetic medications at baseline including oral agents and/or insulin. Patients randomized to the standard or intensive glycemic treatment group were treated for at least 5 yrs (and some up to 7.5 yrs) with the same classes of medications including insulin and the TZD rosiglitazone.

Laser Photocoagulation

Information regarding laser photocoagulation for retinopathy was obtained from questionnaires administered at the baseline and each annual visit. Baseline determination of endothelial cell bioactivity in the protein-A-eluate from plasma, or bFGF-IR (at VANJ) was masked to the information about laser photocoagulation occurrence.

The risk factors associated with time to first laser treatment were modeled in 147 subjects in whom post-baseline data about laser occurrence was available between the $2^{nd}$ and 6th post-baseline annual visits. Laser events occurring during the $1^{st}$ year of study follow up were disregarded to minimize the effect on the time to first laser occurrence of pre-existing retinal lesions.

Baseline Fundus Photographs

Baseline fundus photographs were obtained in all patients. The photographs were evaluated at the Central Fundus Photography Reading Center, University of Wisconsin, Madison, Wis. The frequencies of no retinopathy, microaneurysms, mild non-proliferative, severe non-proliferative and proliferative retinopathy were 29%, 18%, 29%, 17% and 7% respectively. Macular edema was present in 16 of 156 patients (10.3%) in whom it could be assessed from photographs.

Laboratory and Clinical Measures

Standard laboratory and clinical measures were determined as previously described (11). Urinary albumin/creatinine ratio was calculated as albumin concentration/creatinine concentration ×100. LDL cholesterol was calculated using the Friedenwald equation on all samples with plasma triglyceride concentration <400 mg/dL. Blood pressure (BP) was recorded in the seated position after five-minute rest. Three consecutive readings were obtained, and the median value of the three consecutive determinations was used for analysis.

Plasma Samples

Archived, coded EDTA plasma samples were kept frozen (−70 C) for up to 4 years prior to assay of protein-A-eluate fractions for bioactivity in endothelial cells. Bioactivity in protein-A eluate fractions from sera was previously shown to be stable for 5 yrs or longer at −20 C (12). Endothelial cell inhibitory activity in the protein-A eluate fractions from plasma was stable after storage at 0-4 deg C. for 6 months or longer.

Basic Fibroblast Growth Factor Assays: Cut-Point for "Low Vs "High" bFGF-IR

Basic FGF immunoreactivity (bFGF-IR) in plasma was determined using a sensitive specific two-site enzyme-linked immunoassay (R&D Systems, Inc. Minneapolis, Minn.) as previously described (13). We dichotomized this measurement at the value of 4.5 pg/mL, the previously reported upper limit in normal adult men (14).

Cell Culture and Growth Assays

Bovine pulmonary artery (BPA) endothelial cells (Clonetics, Inc. San Diego, Calif.) were maintained at 37 C in 5% $CO_2$/95% air in endothelial cell growth medium (EGM, Clonetics, Inc. San Diego, Calif.) plus 10% fetal calf serum. BPA cells were passaged continuously and used between passages 4-10.

Colorimetric Estimation of Cell Number

Endothelial cell proliferation assays were carried out as previously reported (12). Confluent cells were trypsinized and plated at $10^3$-$10^4$ cells/well in Medium 199 plus 10% fetal calf serum in 96-well plates. After 1 or 2 days incubation for cells to reach 60-80% confluency, test fractions (1:50 dilution of protein A eluates of plasma) were added to wells in quadruplicate. After two days incubation in the presence of test fractions, wells were washed with PBS and processed for the calorimetric estimation of number of cells, i.e. cell-associated acid phosphatase activity, as previously described (12). There was a linear relationship between endothelial cell number and optical density at 410 nm as previously described (12). Growth-promoting activity is expressed as a percentage of the number for cells grown in the absence of test protein-A eluate fractions in a control well. Significant inhibitory activity ($\leq$90%) is defined as that occurring outside the normal range for control, i.e. unexposed cells. Each point represents the mean of quadruplicate determinations. The intra- and inter-assay coefficients of variation were 4% and 7% at 1:50 dilution of protein-A-eluted fractions from plasma of three diabetic subjects (n=3 assays in each patient).

Protein-A Affinity Chromatography

Protein-A affinity chromatography was carried out as previously described (12). Four-tenths mL aliquots of plasma were adjusted to pH 8.0 by adding 0.8 mL 100 mmol/L Tris (pH 8). After syringe filtration to clarify samples, 1 mL was applied to a 1-mL column of packed protein-A beads (Pierce Chemical Co., Rockford, Ill.) equilibrated in 100 mmol/L Tris, pH 8.0. The column was washed and eluted as previously described (12). The eluate fractions containing nearly all the recovered protein were pH neutralized and stored at 0-4 C. Inhibitory activity in protein-A eluate fractions was unchanged, appearing in the retentate fraction after dialysis (10 mmol/L phosphate, pH 7.4) and ultrafiltration on a 10 kD cutoff membrane (Centricon-10; Millipore Corp., Bedford, Mass.). All fractions were sterile filtered (Millipore Corp. Bedford, Mass.; 0.2 um) before assay for growth-promoting activity.

Protein Determinations

Protein concentrations were determined by a bicinchoninic acid protein assay kit (Pierce Chemical Co., Rockford, Ill.).

Statistics

Cox proportional hazards regression analysis was used to model time to first post-baseline laser treatment as a function of possible baseline risk factors. Those possible risk factors were a set of clinical risk variables which based upon published literature (15, 16): (age, diabetes duration, antibody group: </=90% vs >90%, history of hypertension, LDL cholesterol concentration, baseline HbA1c) are known or likely to be associated with retinopathy or laser treatment. Backward elimination was used to determine those variables which contributed significantly (p$\leq$0.05) to the model. With this procedure, we found that the excluded variables (age, history of hypertension, baseline HbA1c, baseline insulin, ACE inhibitor, ARB use, glycemic treatment arm) all had p values >0.20.

Results

Association Between Inhibitory Activity in Endothelial Cells from Protein-A-Eluates and Low Plasma bFGF-IR In the current study, we compared bioactivity in endothelial cells from a 1:50 dilution of the protein-A-eluate fractions of plasma to baseline plasma bFGF-IR in available samples from 162 of the 172 subjects. There was a highly significant association between inhibitory activity in endothelial cells from the protein-A-eluates of plasma and low plasma bFGF-IR (p=0.002; Table 1). Fifty-two of 162 subjects (32%) had inhibitory bioactivity in endothelial cells from the protein-A-eluate fractions of plasma (Table 1).

Protein-A-Eluted Activity in Endothelial Cells and Laser Treatment

Figure 21:
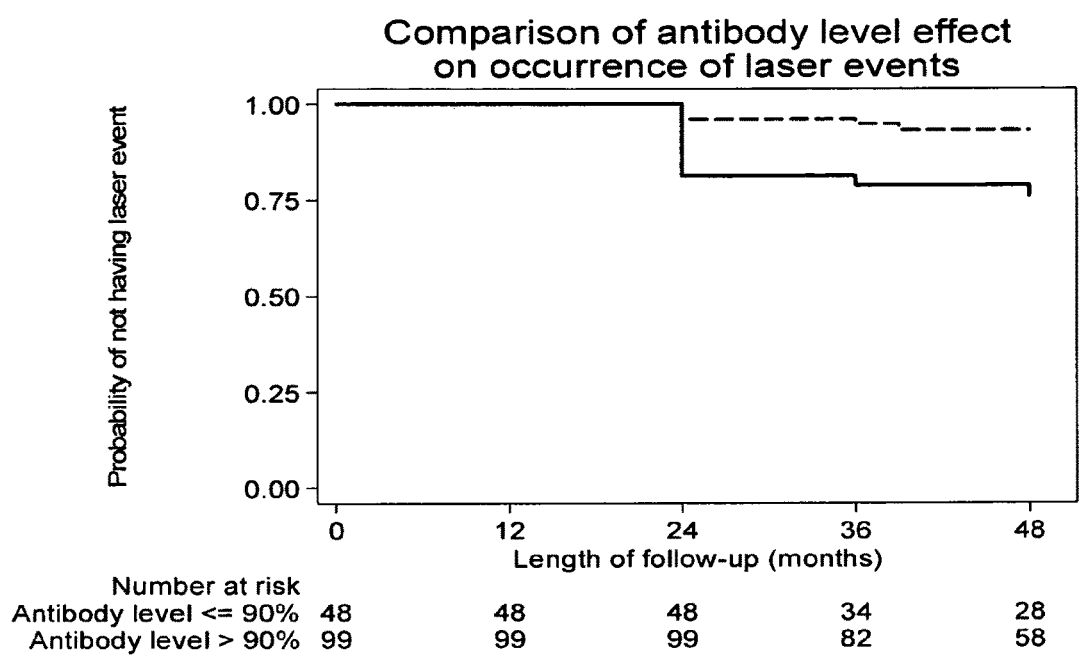
FIG. 21 shows comparison of antibody level effect on occurrence of laser events. The difference in time to occurrence of first laser for antibody groups was statistically significant, p=0.003. Dashed line indicates group with antibody level >90%.

The proportion of subjects unaffected by post-baseline laser differed with respect to the presence or absence of plasma auto-antibodies inhibitory in endothelial cells (FIG. 21). The separation for antibody groups was apparent after 24 months of follow-up and remained relatively constant between 24 and 48 months of treatment in the VADT. For example after 36 months of study treatment, 21% vs 5% of subjects with or without plasma endothelial cell inhibitory auto-antibodies, respectively (p=0.003) had suffered at least one post-baseline laser event. Extending the analysis for up to 5 or to 6 years of study follow-up a significant difference (p=0.02) between the antibody groups regarding time to first laser occurrence was still evident, in the direction of increased laser occurrence for the presence of inhibitory endothelial cell autoantibodies in plasma.

Effect of Clinical Risk Factors on the Need for Laser Treatment

The best fit model of risk factors associated with the time to first laser treatment during four years of follow-up included the following variables as significant predictors: EC auto-antibodies: >/=90% vs <90% (hazard ratio, HR 0.20; p=0.003) and LDL cholesterol concentration (HR 0.98; p=0.02) (Table 2). The results were unchanged after adjusting for diabetes treatment group, or baseline ACE inhibitor, ARB use, or insulin treatment. The same variables, EC auto-antibodies: </=90% vs >90% (HR 0.28; p=0.008), duration of diabetes (HR 1.06; p=0.017) and LDL cholesterol concentration (HR 0.98; p=0.009) (Table 2) also were significantly associated with time to first laser after up to 5 years of study treatment. No first laser events occurred in the year after 5 years of follow-up.

Relation of EC Inhibitory Auto-antibodies to Baseline Risk Factors

When comparing the two plasma EC auto-antibody groups, there was no significant difference in mean values of the variables patient age, BMI, waist-hip ratio, baseline glycosylated hemoglobin, diabetes duration, systolic blood pressure, urine albumin creatinine ratio, or plasma LDL cholesterol concentration (Table 3). There was a significant (p=0.02) inverse association between plasma EC inhibitory auto-antibodies and baseline insulin use and a marginal (p=0.07) inverse association between plasma EC inhibitory auto-antibodies and baseline fibrate use (Table 4). There was no association between plasma EC inhibitory auto-antibodies and any other baseline categorical risk factor including: race/ethnicity, history of hypertension, macro-vascular disease prevalence, baseline use of TZDs, anti-hypertensive medications or current smoking status (Table 4).

Discussion

The present data suggests a novel association between EC inhibitory auto-antibodies and the need for laser treatment in patients with long-standing type 2 diabetes. The increased rate of laser treatment persisted for up to 5 years after initiation of study treatment in spite of the known strong influence of duration of diabetes. An earlier report of a significant association between low baseline plasma bFGF-IR level and the interim (4 years) need for laser treatment in a baseline subset of 172 subjects from the Veterans Affairs Diabetes Trial (10) may be accounted for by a significant association between low baseline bFGF and endothelial cell inhibitory auto-antibodies in plasma.

Endothelial cell binding auto-antibodies were reported in type 1 diabetes in association with proliferative retinopathy (17). Additional studies, however, failed to confirm an association between endothelial cell binding auto-antibodies and either retinopathy or microvascular disease complications (18, 19). Our data are the first to suggest that IgG auto-antibodies in plasma from adults with type 2 diabetes inhibit endothelial cells. This may be consistent with a report that IgG auto-antibodies from a subset of lupus patients with nephropathy induced apoptosis in endothelial cells (20).

Recurrent macular edema requiring repeated laser treatments can contribute to impaired vision in patients with type 2 diabetes. Proliferative diabetic retinopathy may develop later in some patients with type 2 diabetes patients and is thought to be mediated by the effects of another potent, heparin-binding (29) angiogenesis factor, vascular endothelial cell growth factor (VEGF) (30, 31). It is possible that endothelial cell auto-antibodies modulate the bioavailability of more than one kind of potent growth factor, e.g. bFGF, VEGF, capable of acting synergistically (32) to promote angiogenesis. In such cases, neo-vascularization may result through enhanced availability of angiogenic growth factors released after decreases in the affinity of endothelial cell auto-antibodies (33) for circulating HSPG.

TABLE 1

Association between inhibitory bioactivity in endothelial cells from the protein-A eluates of plasma and low baseline bFGF immunoreactivity.

| | bFGF-IR (pg/mL) | | |
|---|---|---|---|
| Antibody[a] | Low (0-4.4) | High (>/=4.5) | p-value |
| </=90% | 36 (69%) | 16 (31%) | 0.002* |
| >90% | 48 (44%) | 62 (56%) | |

[a] A 1/50 dilution of protein-A eluate of plasma was assayed for change in endothelial cell (EC) number as described in Materials and Methods.
Results are number or (%) of subjects
*p-value from Chi-square Test.

TABLE 2

Cox proportional hazard regression: time to first laser treatment

| Variable | HR | 95% CI | p-value |
|---|---|---|---|
| 4 yrs post-baseline | | | |
| Antibody group (≦90% vs >90%) | 0.20 | 0.07-0.58 | 0.003 |
| LDL cholesterol | 0.98 | 0.96-1.0 | 0.02 |
| 5 yrs post-baseline | | | |
| Antibody group (≦90% vs >90%) | 0.28 | 0.17-0.72 | 0.008 |
| Diabetes duration | 1.06 | 1.01-1.11 | 0.017 |
| LDL cholesterol | 0.98 | 0.99-0.96 | 0.009 |

HR—hazard ratio,
CI—confidence interval

TABLE 3

Associations between inhibitory antibody activity (<90%) and continuous baseline risk factors in 162 patients

| Risk factor | Antibody <= 90% | Antibody > 90% | p-value* |
|---|---|---|---|
| Age (yr) | 59.5 ± 7.9 | 59.3 ± 8.6 | 0.85 |
| HbA1c (%) | 9.5 ± 1.4 | 9.4 ± 1.5 | 0.74 |
| Duration of diabetes (yrs) | 10.4 ± 7.8 | 11.8 ± 8.2 | 0.30 |
| Urinary ACR (mg/g) | 177.8 ± 632.5 | 104.9 ± 266.0 | 0.43 |
| LDL cholesterol (mg/dL) | 105.3 ± 29.4 | 102.0 ± 34.2 | 0.56 |
| Systolic BP (mm Hg) | 130.6 ± 16.0 | 130.0 ± 18.3 | 0.84 |
| BMI (kg/m$^2$) | 31.0 ± 3.0 | 31.6 ± 4.6 | 0.39 |
| Waist/hip ratio | 0.997 ± 0.073 | 1.006 ± 0.070 | 0.45 |

Results are mean ± SD;
ACR—albumin/creatinine ratio.
*p-values from T-Test

TABLE 4

Associations between inhibitory antibody activity (<90%) and baseline categorical risk factors in 162 patients

| Variable | Antibody <= 90% | Antibody > 90% | p-value* |
|---|---|---|---|
| Demographics | | | |
| Male | 100 | 96.4 | 0.16 |
| Hispanic | 19.2 | 14.6 | 0.45 |
| Non-Hispanic white | 57.7 | 69.1 | 0.15 |
| African-American | 21.2 | 15.5 | 0.37 |
| Current smoker | 17.3 | 17.3 | 1.00 |
| Baseline medications | | | |
| Beta blocker | 9.6 | 11.8 | 0.68 |
| ACE inhibitor | 71.2 | 67.3 | 0.62 |
| Angiotensin receptor blocker | 9.6 | 3.6 | 0.12 |
| Calcium channel antagonist | 21.2 | 19.1 | 0.76 |
| Thiazide diuretic | 11.5 | 20.0 | 0.18 |
| Statin | 59.6 | 66.4 | 0.40 |
| Fibrate | 11.5 | 23.6 | 0.07 |
| Thiazolidinedione | 21.2 | 18.2 | 0.65 |
| Insulin | 32.7 | 52.7 | 0.02 |
| Sulfonylurea | 71.2 | 61.8 | 0.25 |
| Metformin | 80.8 | 75.5 | 0.45 |
| Thyroid hormone | 3.9 | 7.3 | 0.40 |
| History | | | |
| Hypertension | 67.3 | 75.2 | 0.29 |
| Myocardial infarction | 9.6 | 16.2 | 0.26 |

TABLE 4-continued

Associations between inhibitory antibody activity (<90%) and baseline categorical risk factors in 162 patients

| Variable | Antibody <= 90% | Antibody > 90% | p-value* |
|---|---|---|---|
| Coronary revascularization | 19.2 | 20.0 | 0.91 |
| Any macrovascular event (MI, CABG, angina, stroke, PVD) | 32.7 | 43.8 | 0.18 |
| Albuminuria (U alb/creat ratio) | | | |
| Macro ≧300 mg/g | 9.6 | 8.7 | 0.96 |
| Micro 30-299 mg/g | 26.9 | 28.9 | |
| Normo <30 mg/g | 63.5 | 62.5 | |

Results are % of patients
*p-values from Chi-square Test

References for Example 11

1. *Centers for Disease Control and Prevention* (CDC), 2004, Prevalence of visual impairment and selected eye diseases among persons aged >/=50 years with and without diabetes—United States, 2002. MMWR Morb Mortal Wkly Rep. 53(45), 1069-1071.
2. Krzentowski G, Zhang L, Albert A, Lefèbvre P J. 2004 [Another look at the implications of the DCCT study] Ann Endocrinol (Paris). 65(5), 429-435.
3. Keech A C, Mitchell P, Summanen P A, O'Day J, Davis T M, Moffitt M S, Taskinen M R, Simes R J, Tse D, Williamson E, Merrifield A, Laatikainen L T, d'Emden M C, Crimet D C, O'Connell R L, Colman P G; *FIELD study investigators.* 2007, Effect of fenofibrate on the need for laser treatment for diabetic retinopathy (FIELD study): a randomised controlled trial. Lancet. 370(9600), 1687-1697.
4. Girach A, Lund-Andersen H., 2007. Diabetic macular oedema: a clinical overview. *Int J Clin Pract.* 61(1), 88-97.
5. Aroca P R, Salvat M, Fernandez J, Mendez I., 2004, Risk factor for diffuse and focal macular edema, J Diabetes Complications., 18(4), 211-215.
6. Deckert T, Feldt-Rasmussen B, Borch-Johnsen K, Jensen T, Kofoed-Enevoldsen A. 1989, Albuminuria reflects widespread vascular damage: the Steno hypothesis. Diabetologia. 32, 219-226.
7. Folkman J., Klagsbrun M., 1987. Angiogenic factors. Science 235, 442-447.
8. Esch F., Baird A., Ling N., Ueno N., Hill F., Denoroy L., Klepper R., Gospodarowicz D., Bohlen P., Guillemin R., 1985. Primary structure of bovine pituitary basic fibroblast growth factor (FGF) and comparison with the amino-terminal sequence of bovine brain acidic FGF. Proc Nat Acad Sci (USA) 19, 6507-6511.
9. Zimering M. B., Eng J., 1996. Increased basic fibroblast growth factor-like substance in plasma from a subset of middle-aged or elderly male diabetic patients with microalbuminuria or proteinuria. J Clin Endo Metab. 81, 4446-4452.
10. Zimering, M. B., Anderson, R. J., Luo, P., Pardun, J. and VADT Substudy Group. Inverse association between plasma basic fibroblast growth factor immunoreactivity and laser treatment for retinopathy in a baseline subset of adult type 2 diabetes from the Veterans Affairs Diabetes. Trial. 89$^{th}$ Annual Meeting of the Endocrine Society, P2-249, 2007.
11. Abraira C., Duckworth W., McCarren M., Emanuele N., Arca D., Reda D., Henderson W., 2003. Design of the cooperative study of glycemic control and complications in diabetes mellitus type 2. J Diab & Compl. 17, 314-322.
12. Zimering, M. B., Thakker-Varia, S. Increased fibroblast growth factor-like autoantibodies in serum from a subset of patients with cancer-associated hypercalcemia. Life Sciences 71 (25) 2939-2959, 2002.
13. Zimering M. B., 2002. Effect of intravenous bisphosphonates on release of basic fibroblast growth factor in serum of patients with cancer-associated hypercalcemia. Life Sciences, 70, 1-14.
14. Larsson A., Skoldenberg E., Ericson H., 2002. Serum and plasma levels of FGF-2 and VEGF in healthy blood donors. Angiogenesis 5, 107-110.
15. Higgins G. T., Khan J., Pearce I. A., 2007, Glycaemic control and control of risk factors in diabetes patients in an opthalmology clinic: what lessons have we learned from the UKPDS and DCCT studies? *Acta Opthalmol Scand.* 85(7), 772-776.
16. Miljanovic B., Glynn R. J. Nathan D. M. Manson J. E. Schaumberg D. A. 2004 A prospective study of serum lipids and risk of diabetic macular edema in type 1 diabetes. Diabetes. 53(11), 2883-2892.
17. Jones D B, Wallace R, Frier B M. 1992. Vascular endothelial cell antibodies in diabetic patients. Association with diabetic retinopathy. Diabetes Care. 15(4), 552-555.
18. Petty R G, Pottinger B E, Greenwood R M, Pearson J D, Mahler R F 1991, Diabetes is associated with a high incidence of endothelial-binding antibodies which do not correlate with retinopathy, von Willebrand factor, angiotensin-converting enzyme or C-reactive protein. Diabetes Res. 17(3), 115-123.
19. Wangel A G, Kontiainen S, Scheinin T, Schlenzka A, Wangel D, Mäenpää J. 1992, Anti-endothelial cell antibodies in insulin-dependent diabetes mellitus. Clin Exp Immunol. 88(3), 410-413.
20. van Paassen P, Duijvestijn A, Debrus-Palmans L, Damoiseaux J, Vroomen M, Tervaert J W. 2007, Induction of endothelial cell apoptosis by IgG antibodies from SLE patients with nephropathy: a potential role for anti-endothelial cell antibodies. Ann N Y Acad. Sci. 1108, 147-156.
21. Vlodavsky I Miao H Q, Medalion B, Danagher P. Ron D., 1996. Involvement of heparan sulfate and related molecules in sequestration and growth promoting activity of fibroblast growth factor. Cancer Metastasis Rev, 15(2), 177-186.
22. Fillit H, Lahita R, 1991, Antibodies to vascular heparan sulfate proteoglycan in patients with systemic lupus erythematosus. *Autoimmunity.* 9(2), 159-164.
23. Fillit H, Mulvihill M., 1993. Association of autoimmunity to vascular heparan sulfate proteoglycan and vascular disease in the aged. *Gerontology.* 39(4), 177-182.
24. Eldor A, Bar-Ner M, Yahalom J, Fuks Z, Vlodavsky I. 1987, Role of heparanase in platelet and tumor cell interactions with the subendothelial extracellular matrix. *Semin Thromb Hemost.* 13(4), 475-488.
25. Jensen T. 1997, Pathogenesis of diabetic vascular disease: evidence for the role of reduced heparan sulfate proteoglycan. *Diabetes.* 46 Suppl 2:S98-100.
26. Ishai-Michaeli R, Eldor A, Vlodavsky I. 1990, Heparanase activity expressed by platelets, neutrophils, and lymphoma cells releases active fibroblast growth factor from extracellular matrix. *Cell Regul.* (11), 833-842.
27. Han J, Woytowich A E, Mandal A K, Hiebert L M. 2007, Heparanase upregulation in high glucose-treated endothelial cells is prevented by insulin and heparin. *Exp Biol Med* (Maywood). 232(7), 927-934.
28. Chen G, Wang D, Vikramadithyan R, Yagyu H, Saxena U, Pillarisetti S, Goldberg I J. 2004, Inflammatory cytokines and fatty acids regulate endothelial cell heparanase expression. *Biochemistry.* 43(17), 4971-4977.
29. Ferrara N. Henzel W J. 1989, Pituitary follicular cells secrete a novel heparin-binding growth factor specific for vascular endothelial cells. Biochem Biophys Res Commun. 161(2), 851-858.
30. Aiello L P, Wong J S., 2000, Role of vascular endothelial growth factor in diabetic vascular complications. *Kidney Int Suppl.* 77, S113-119.
31. Nguyen Q D, Tatlipinar S, Shah S M, Haller J A, Quinlan E, Sung J, Zimmer-Galler I, Do D V, Campochiaro P A., 2006, Vascular endothelial growth factor is a critical stimulus for diabetic macular edema. *Am J Opthalmol.* 142(6), 961-969.
32. Pepper M S, Ferrara N, Orci L Montesano R. 1992, Potent synergism between vascular endothelial growth factor and basic fibroblast growth factor in the induction of angiogenesis in vitro. Biochem-Biophys Res Commun. 189(2):824-831.
33. Renaudineau Y, Revelen R. Bordron A, Mottier D, Youinou P, Le Corre R. 1998, Two populations of endothelial cell antibodies cross-react with heparin. *Lupus.* 7(2): 86-94.

EXAMPLE 12

The data here suggest autoantibodies from a subset of advanced type 2 diabetes may contribute to a spectrum of diabetic vascular complications through their ability to activate endothelial cell Rho kinase and induce apoptosis.
Methods
Subjects The baseline clinical characteristics in two groups of diabetic subjects from the VADT (with maculopathy or without significant retinopathy) are shown in Table 1.

Because of the limited volume of plasma available from each test subject (0.5-1.0 mL), potent inhibitory autoantibodies from two additional subjects (Patient 1, 2) were used in some experiments. Patient 2 progressed from micro-albuminuria to overt albuminuria during 4 years of follow up in the VADT. Patient 1 neither required laser treatment nor progressed to macro-albuminuria during the same 4-year VADT interval.
Diagnostic Subgroups
Non-ischemic Cardiomyopathy Patient 3: A 55 yr old male with type 2 dm×20 yrs and clinically significant macular edema requiring two focal laser treatments. Other complications included depression, mononeuritis multiplex, renal insufficiency and progression to albuminuria. Prior to the onset of refractory paroxysmal atrial fibrillation and hard syncope which required the implantation of an automated defibrillator, plasma demonstrated titers of potent inhibitory endothelial cell auto-antibodies which subsequently persisted for at least two years. Serial echocardiography and left cardiac catheterization showed normal coronaries, mild left atrial enlargement, grade I-II diastolic dysfunction, and left ventricular hypertrophy.

Patient 4: A 67 yr old male with type 2 dm×7 yrs with dry age-related macular degeneration (AMD), mild non-proliferative diabetic retinopathy, and cataracts. Diabetic-related complications included: depression, painful radiculopathy, and albuminuria without renal insufficiency. Plasma demonstrated high titers of very potent endothelial cell inhibitory auto-antibodies 1 year prior to the first of five hospitalizations over a ten month period requiring treatment for moderately severe aortic regurgitation, moderate pericardial effusion, pulmonary hypertension, and hypertrophic cardiomyopathy. Other significant findings included: proximal aneurysmal dilatations of the left anterior descending, left circumflex and right coronary arteries, bradyarrythmias with hypotension requiring placement of a permanent pacemaker, and hematochezia from an unknown source requiring multiple blood transfusions. ANA and ESR were both within normal limits. Two years after initial presentation with cardiac symptoms, the patient symptoms resolved in association with complete disappearance of endothelial cell inhibitory auto-antibodies.
Recurrent Macular Edema Patient 5: A 58 yr old male with type 2 dm for 10-15 yrs. Family history significant for mother with diabetes and end stage renal disease. Diabetes-related complications include: hypertension and painful peripheral neuropathy. Over a 58 month follow up period, the patient underwent five focal laser treatments for recurrent macular edema in the right eye. He lost 8 lines of letters on the 20/20 Snellen visual acuity chart and was unable to drive a car at night. He experienced a doubling in serum creatinine concentration compared to normal baseline level, progression to macro-albuminuria, and one episode of a transient ischemic attack. Plasma demonstrated the stable presence of inhibitory endothelial cell autoantibodies over the same time period.
Plasma Samples All plasma samples were obtained after subjects provided their consent for participation in an IRB-approved study. Archived, coded EDTA plasma samples were kept frozen (−70 C) for up to 4 years prior to assay of protein-A-eluate fractions for bioactivity in endothelial cells. Bioactivity in protein-A eluate fractions from sera was previously shown to be stable for 5 yrs or longer at −20° C. (13). Endothelial cell inhibitory activity in the protein-A eluate fractions from plasma was stable after storage at 0-4° C. for 6 months or longer.
Protein-A Affinity Chromatography Protein-A affinity chromatography was carried out as previously described (13). Briefly, aliquots of plasma were adjusted to pH 8.0 by adding 0.8 mL 100 mmol/L Tris (pH 8). After syringe filtration to clarify samples, 1 mL was applied to a 1-mL column of packed protein-A beads (Pierce Chemical Co., Rockford, Ill.) equilibrated in 100 mmol/L Tris, pH 8.0. After washing, the column was eluted. The eluate fractions containing nearly all the recovered protein were pH neutralized and stored at 0-4 C. Inhibitory activity in protein-A eluate fractions was unchanged, appearing in the retentate fraction after dialysis (10 mmol/L phosphate, pH 7.4) and ultrafiltration on a 10 kD cutoff membrane (Centricon-10; Millipore Corp., Bedford, Mass.). All fractions were sterile filtered (Millipore Corp. Bedford, Mass.; 0.2 um) before assay for growth-promoting activity.
Cell Culture and Growth Assays Bovine pulmonary artery endothelial cells (Clonetics, Inc. San Diego, Calif.) were maintained at 37 C in 5% $CO_2$/95% air in endothelial cell growth medium (EGM, Clonetics, Inc., San Diego, Calif.) plus 10% fetal bovine serum. The cells were passaged continuously and used between passages 4-10.
Colorimetric Estimation of Endothelial Cell Number Colorimetric estimation of cell number was carried out as previously reported (13). Confluent cells were trypsinized and plated at $10^3$-$10^4$ cells/well in Medium 199 plus 10% fetal calf serum in 96-well plates. After up to four days incubation for cells to reach 60-80% confluency, test fractions (30 μg/mL were added to wells in quadruplicate. After two days incubation in the presence of test fractions, cells were washed with PBS and processed for the calorimetric estimation of cell number, i.e. cell-associated acid phosphatase activity, as previously described (13). There was a linear relationship between endothelial cell number and optical density at 410 nm. Growth-promoting activity is expressed as a percentage of the control cell number for cells grown in the absence of test protein-A eluate fractions. Each point represents the mean of quadruplicate determinations. The intra- and inter-assay coefficients of variation were 4% and 7% for 30 ug/mL of protein-A-eluted fractions from plasma of three diabetic subjects (n=3 assays in each patient).

Protein Determinations

Protein concentrations were determined by a bicinchoninic acid protein assay kit (Pierce Chemical Co., Rockford, Ill.).

Microscopy Imaging.

For bright field images, the ~90% confluent endothelial cells in 24-well plates with various treatments were visualized under Zeiss Axiovert 200 inverted microscope with phase contrast 20× dry lens (NA 0.4). Alternatively, the cells cultured in glass-bottom dishes were monitored under transmission light mode (DIC images) with Zeiss LSM510 META confocal microscope with 63×, water immersion lens (NA 1.2). The live cell DIC images of the endothelial cells were captured continuously up to 15 minutes at room temperature at the speed of about 1 frame/min. For fluorescence images, the cells were cultured on glass-bottom dishes for two days before the experiments. At indicated time point after addition of autoantibodies, 10 μM Hoechst dye 33342 (Sigma Inc., St Louis, Mo.) was added into the culture medium for 15 min at 37° C. in a dark chamber. As described previously, the chromatin condensation and fragmentation was visualized with the Zeiss confocal laser scanning microscope using a 63× water immersion objective, with the excitation wavelength set at 351 nm and the emission filter set at 385-470 nm. We used Texas Red-labeled phalloidin to visualize actin stress fibers. First, we aseptically inserted glass coverslips (12-mm diameter) into 24-well tissue culture plate. After incubation with autoantibodies in the culture medium for 20 minutes, the cells were fixed in 3.7% paraformaldehyde-phosphate buffered saline (PBS) containing 0.1% Triton X-100 for 10 min at room temperature (pH 7.2). Cells were then washed twice with PBS and subsequently permeabilized with 0.2% Triton X-100 in PBS for 10 min. Texas Red-labeled phalloidin (5 μg/ml) was added in blocking solution (1% BSA-0.1% Triton X-100 in PBS) for 3 hours in a dark chamber at room temperature. After the cells were extensively washed with PBS, the coverslips were mounted on a slide with a mounting medium (Gel/Mount, Biomeda, Inc. Foster City, Calif.). Images were captured using the Zeiss confocal microscope with 543 nm HeNe laser for excitation and 560-615 nm filter for emission.

Apoptosis Assay. Endothelial cells were cultured in 24-well plates to reach ~90% confluence. Purified IgG was added directly to cultured medium. At 0, 6, 12, 18 and 24 hours, culture media was removed and the cells were incubated in a balanced salt solution (BSS) (140 mM NaCl, 2.8 mM KCl, 2 mM CaCl2, 2 mM MgCl2, 10 mM HEPES, pH 7.2) containing propidium iodide (PI, 25 μg/ml) and Hoechst 33342 (10 μM, Sigma) for 15 min. The cells were examined by Zeiss Axiovert 200M microscope using 20× objective (NA 0.4) for phase contrast, fluorescent blue (Hoechst) and red (PI) images. As a membrane permeable dye, Hoechst stains all nuclei with bright blue, while cell impermeable PI only stains the nuclei in the dying cells, which lost their membrane integrity. Early apoptotic cells whose membranes are still intact present only blue nuclei, but the initiation of DNA fragmentation result in patched labeling of the nuclei by Hoechst (14). Cells entering the late apoptotic stage have bright red condensed chromatin or fragmented nuclei that distinguish them from necrotic ones, which have a uniform red color usually with enlarged nuclei. For each experiment, a minimum of total 400 cells for each duplicated sample were counted from at least five randomly chosen fields and the percentage of total apoptotic cells was obtained by adding early and late apoptotic cells. Each experiment was repeated at least three times.

Western Blot. Control and treated cells at 12 hours were harvested and washed twice with ice-cold phosphate-buffered saline, and lysed with modified RIPA buffer (150 mmol/L NaCl, Tris-Cl, pH 8.0, 1 mmol/L EGTA, 1% Triton X-100, 0.1% SDS, 1% sodium deoxycholate) in the presence of protease inhibitors (0.1 mmol/L phenylmethylsulfonyl fluoride, 1.0 mmol/Lpepstatin, 1 mmol/Lbenzamidine, 10 mmol/Lleupeptin, 1 mg/ml aprotinin). The whole cell lysate was mixed with a 2× sample buffer (200 mmol/L Tris-Cl, pH 6.7, 9% SDS, 6% b-mercaptoethanol, 15% glycerol, 0.01% bromphenol blue) and separated on a 15% linear gradient SDS-polyacrylamide-gel after heating the samples at 80° C. for 5 min. The proteins were transferred to a polyvinylidene difluoride membrane and probed with anti-cleaved caspase-3 rabbit monoclonal antibody (Asp 175) (5A1, Cell Signaling Technology, Danvers, Mass.). This antibody specifically detects the large fragment (17/19 kDa) of activated caspase-3 resulting from cleavage adjacent to Asp175 but not full length caspase-3. The protein-antibody complexes were then blotted with a horseradish peroxidase-linked secondary antibody and the signal detected on Kodak films using chemiluminescent kit (Pierce, Rockford, Ill.).

Results

Effects of Protein-A Elutes of Plasma in Endothelial Cells

Increased Growth-inhibitory Activity in Plasma from Subsets of Diabetes

Figure 22:
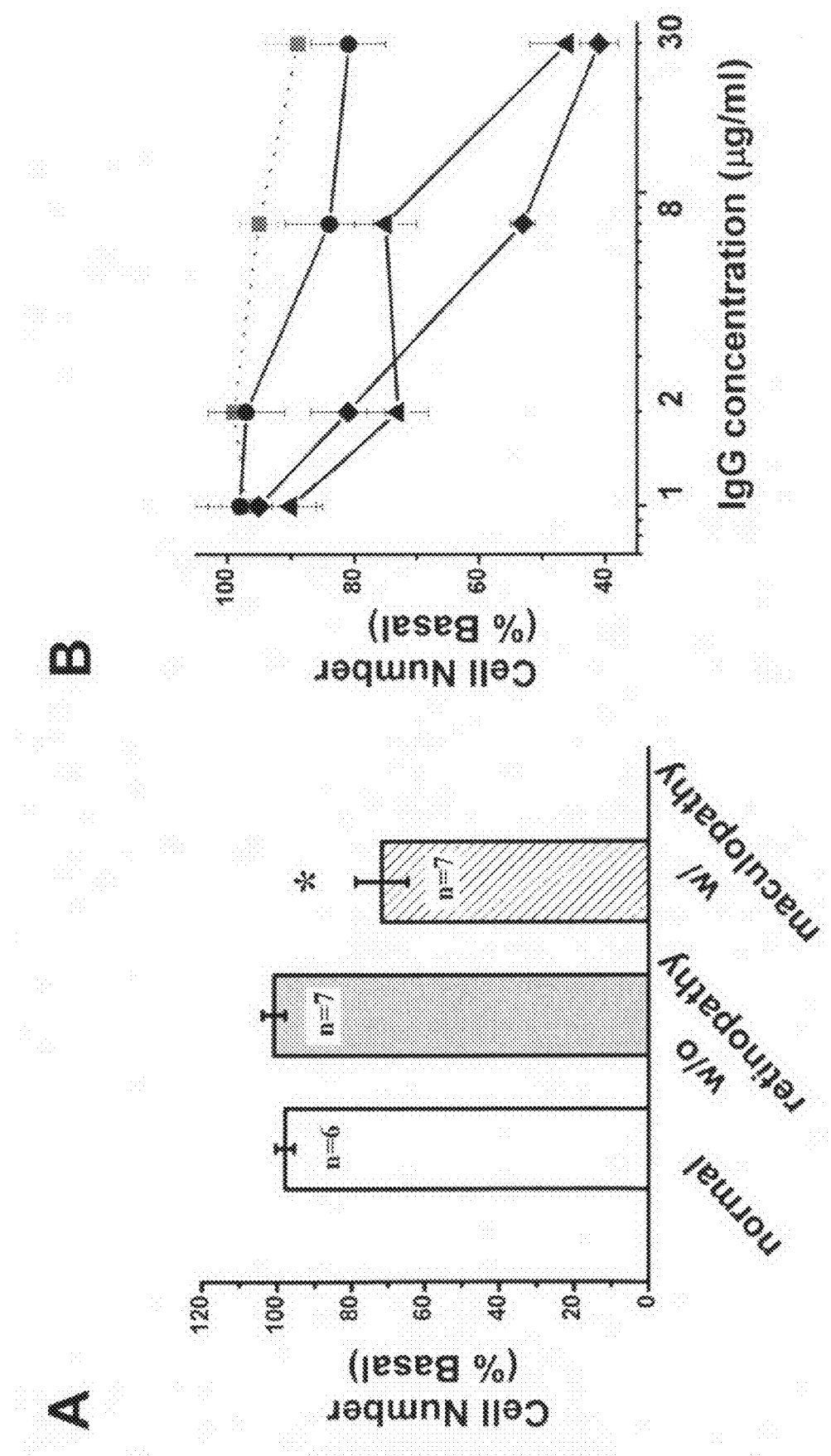
FIG. 22 shows A) Protein-A eluates from diabetes with maculopathy cause significant decrease in endothelial cell number compared to eluates from diabetes with no retinopathy or age-matched normal subjects. A one-fiftieth dilution (30 ug/mL) of the protein-A eluate was incubated with cells for 48 hrs as described in Methods. *p<0.01. B) dose-response curves for diabetic plasma IgG-induced inhibition of endothelial cell proliferation. Square, patient without maculopathy; circle, Patient 5 with recurrent macular edema; triangle, Patient 3 with macular edema and cardiomyopathy; diamond, Patient 4 with AMD and cardiomyopathy.

Mean protein-A eluted activity (72±20%, n=7) in diabetic subjects with maculopathy (five with macular edema required one or more laser treatments, two with early age-related macular degeneration) significantly exceeded (P<0.01) mean activity in normal subjects (98±6%, n=6) and in diabetic subjects with minimal or no retinopathy (101±8%, n=7) (FIG. 22a). To test whether this inhibitory activity comes from auto-antibody, we used a 1/50 dilution (30 ug/mL) of the IgG fraction extracted from plasma using protein-A affinity chromatography.

Titer

Dose-proliferation curves in endothelial cells demonstrated high potency and/or a high titer of inhibitory autoantibodies in plasma from patients with macular edema and other complications. Two diabetic subjects with non-ischemic cardiomyopathy (Patients 3, 4) had highest potency inhibitory autoantibodies (FIG. 22b).

Figure 23:
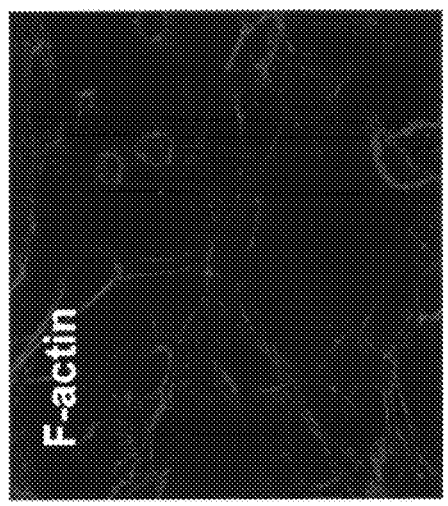
FIG. 23 shows auto-antibodies from type 2 diabetic patients induced apoptosis in endothelial cells. Bovine endothelial cells were cultured with or without purified IgG from normal or diabetic patients. A. bright-field images of endothelial cells after 12 hours treatment with purified IgG from normal or diabetic patients. Without addition of purified human IgG, endothelial cells displayed a rapid growth rate and normal morphology (ctrl). Addition of normal human IgG in the culture medium (NL) slightly inhibited the growth of the cells if any effect at all. However, addition of similar concentrations (20-30 ug/mL) of purified IgG from diabetic patients (Pt 1 and Pt 2) induced significant cell death. B. Hoechst dye 33342 staining images showed the nuclear fragmentation and condensation which is the hallmark for apoptosis in cells treated with purified IgG from diabetic patients, but not in control cells or cells treated with normal human IgG. C. Time course of IgG induced apoptosis. Data are from at least three experiments, mean±s.e., p<0.0001 at 6, 12 and 24 hours. Results similar to those in panel A were observed from IgG fraction of plasma of four other diabetic subjects with maculopathy.
Figure 23:
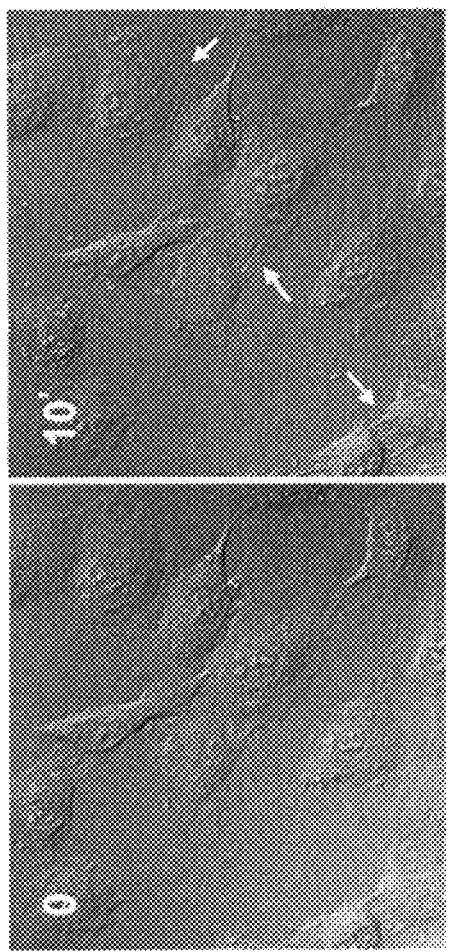
Figure 23:
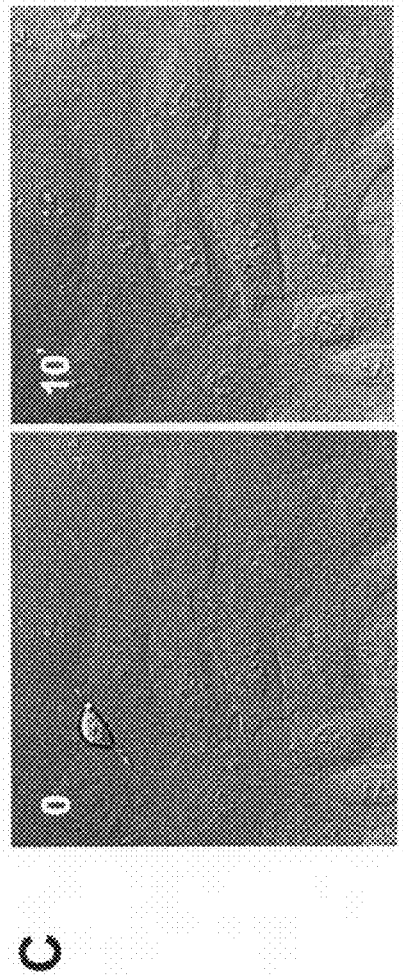
Figure 23:
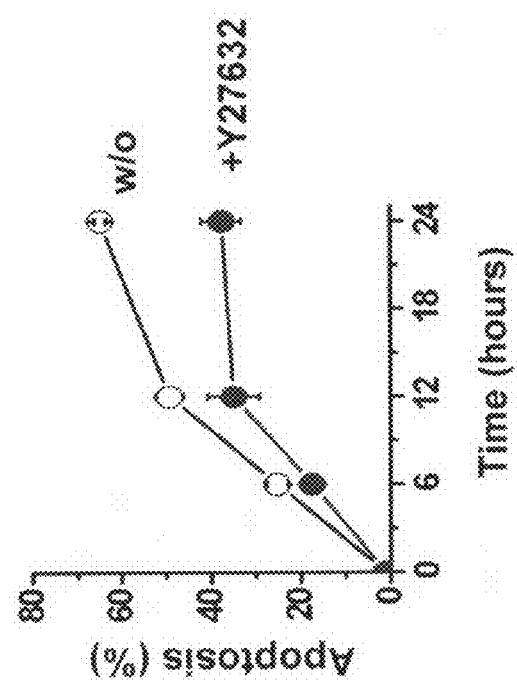

Rho Kinase-mediated Stress Fiber Formation and Cell Contraction in Endothelial Cells Induced by Diabetic Plasma IgG Auto-antibodies When the endothelial cells were exposed to IgG autoantibodies from diabetic plasma but not normal control plasma, we observed the cells started to contract almost immediately. Ten minutes after exposure to potent diabetic plasma IgG auto-antibodies, endothelial cells had retracted from their prior close cell-cell contacts (FIG. 23a). Since the stress fiber could be observed in DIC images (FIG. 23a), we used Texas Red-labeled phalloidin to further label them. As shown FIG. 23b, the cells displayed dramatic filamentous (F)-actin immunoreactive stress fibers. Moreover, the formation of stress fiber could be largely inhibited by co-incubation with a specific rho kinase inhibitor, Y27632 (10 uM) (FIG. 23c).

Figure 24:
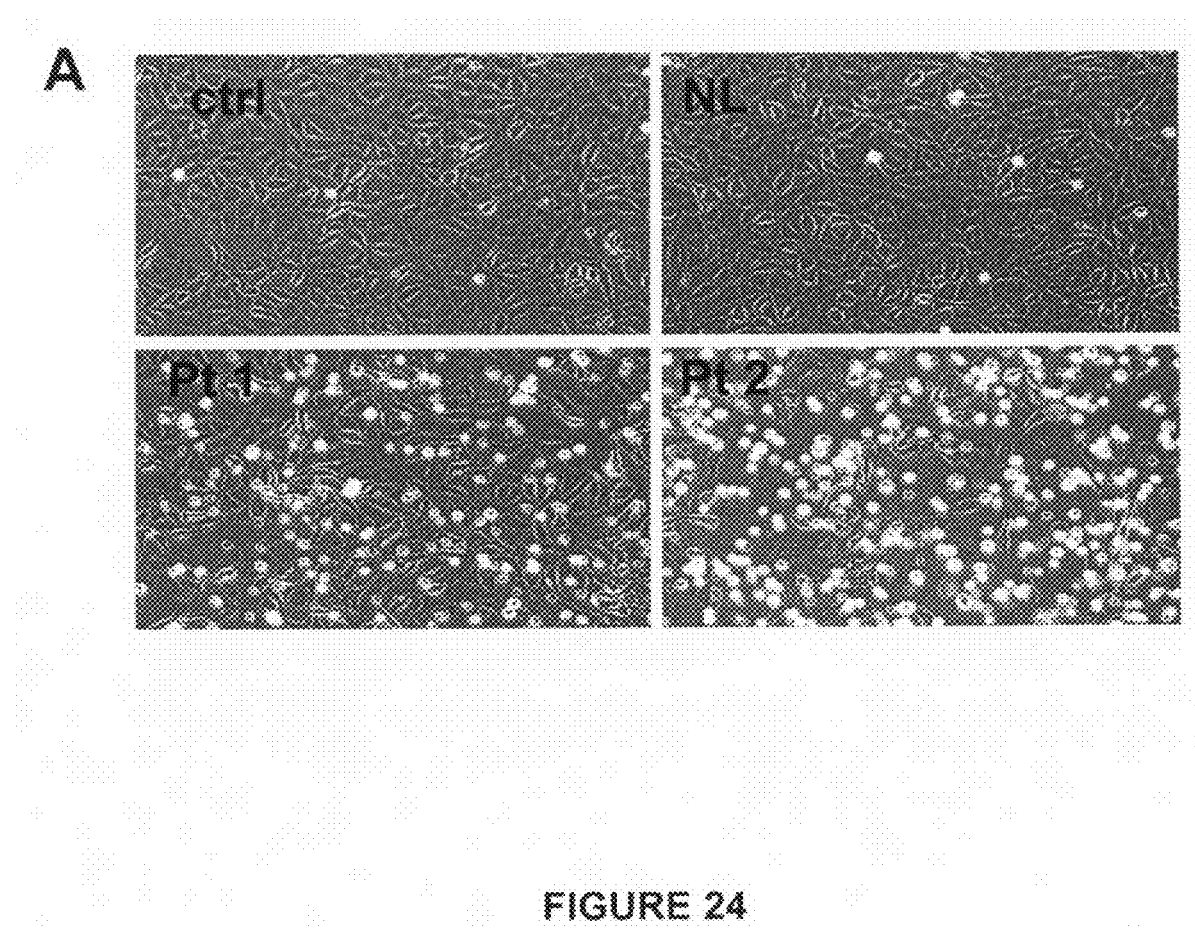
FIG. 24 shows auto-antibodies from type 2 diabetic patients induced apoptosis in endothelial cells. Bovine endothelial cells were cultured with or without purified IgG from normal or diabetic patients. A. bright-field images of endothelial cells after 12 hours treatment with purified IgG from normal or diabetic patients. Without addition of purified human IgG, endothelial cells displayed a rapid growth rate and normal morphology (ctrl). Addition of normal human IgG in the culture medium (NL) slightly inhibited the growth of the cells if any effect at all. However, addition of similar concentrations (20-30 ug/mL) of purified IgG from diabetic patients (Pt 1 and Pt 2) induced significant cell death. B. Hoechst dye 33342 staining images showed the nuclear fragmentation and condensation which is the hallmark for apoptosis in cells treated with purified IgG from diabetic patients, but not in control cells or cells treated with normal human IgG. C. Time course of IgG induced apoptosis. Data are from at least three experiments, mean±s.e., p<0.0001 at 6, 12 and 24 hours.
Figure 24:
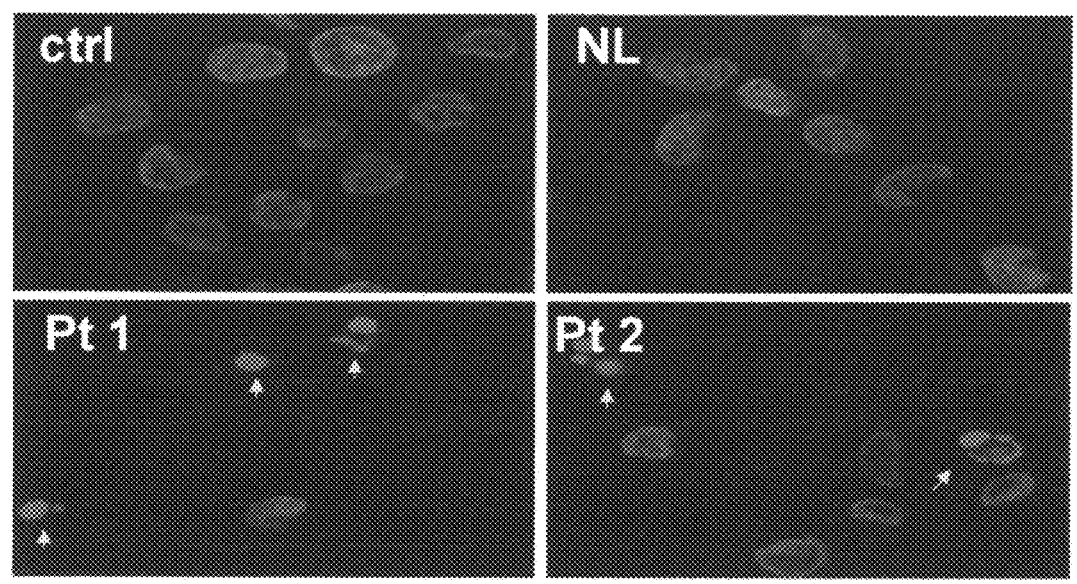
Figure 24:
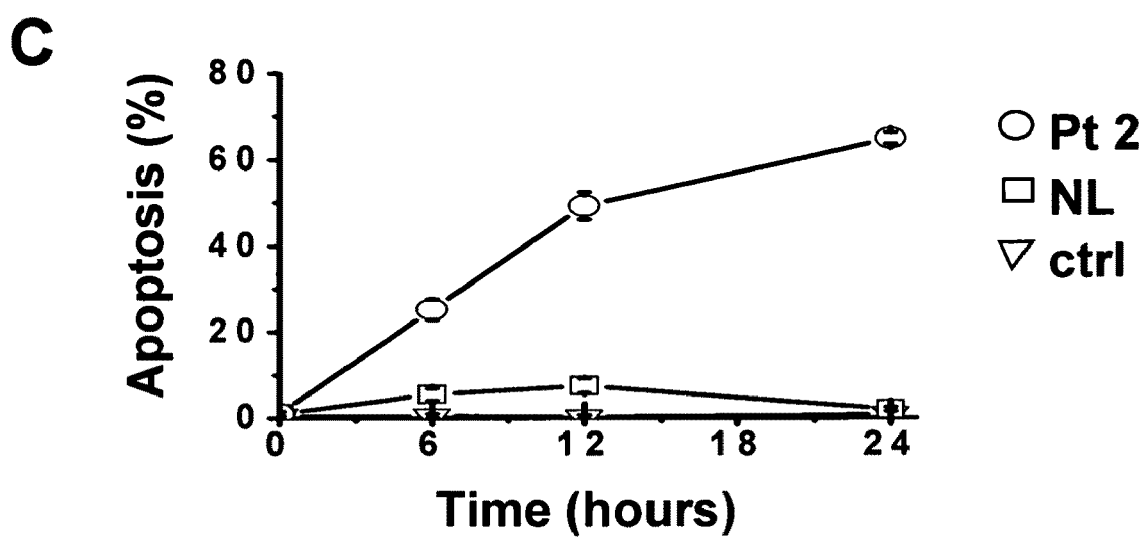
Figure 25:
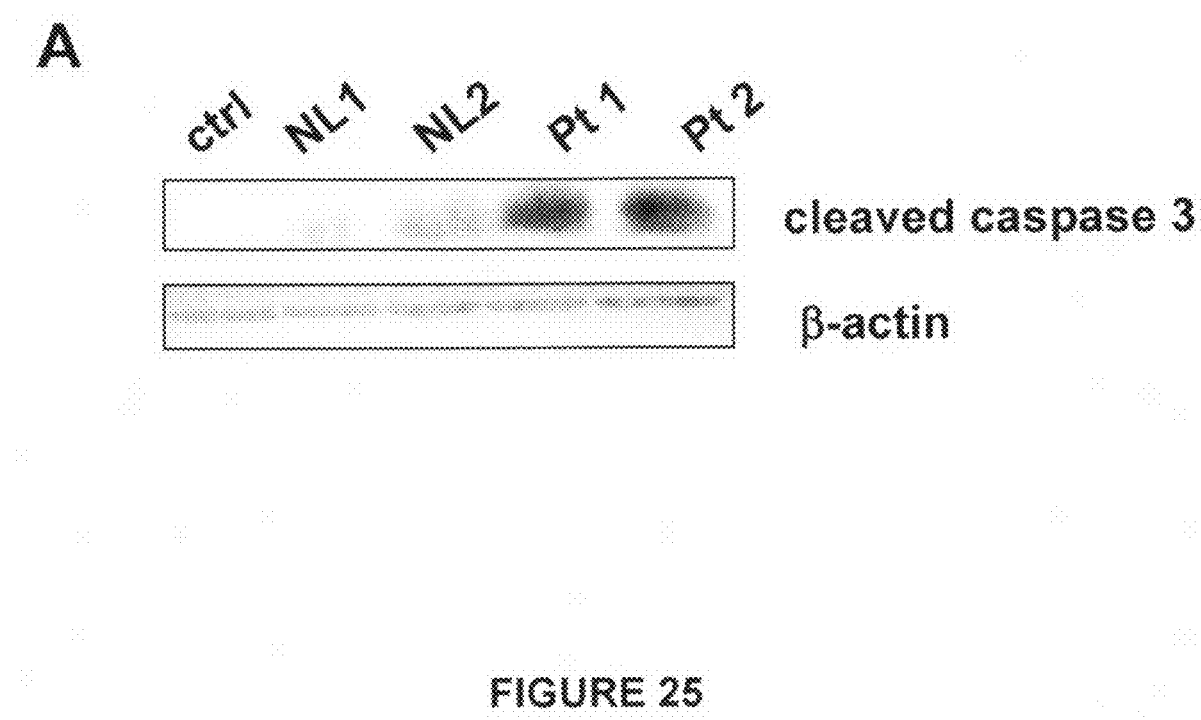
FIG. 25 shows inhibition of caspases could rescue endothelial cells from auto-antibodies-induced apoptosis. A. Western Blot demonstrated that caspase-3 was activated in auto-antibodies-treated endothelial cells. Ctrl: without treatment; NL1, IgG from normal human #1; NL2, IgG from normal human #2; Pt 1, IgG from diabetic patient #1; Pt 2: IgG from diabetic patient #2. Mouse monoclonal antibody specifically against cleaved but not full-length caspase 3 was used here. B. Hoechst dye staining images of endothelial cells after 12 hours treatment with purified IgG from patient #2. 10 μM pan-caspases inhibitor Q-VD-OPH(OPH) in the medium almost completely blocked apoptosis in endothelial cells (lower panel). Compared with cells without OPH, the cells appeared to have normal morphology and nuclei are intact.
Figure 25:
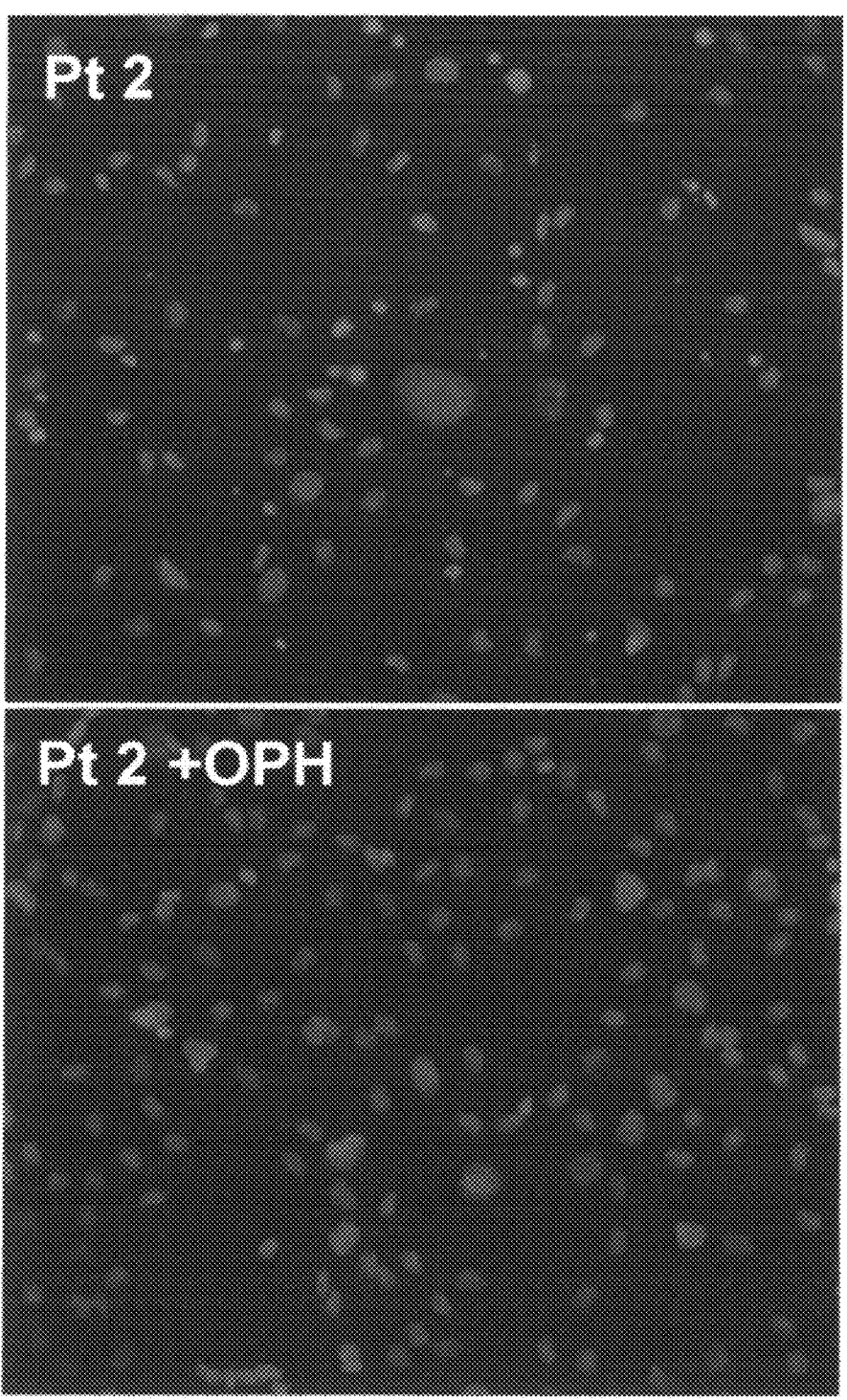

Diabetic Plasma Auto-antibodies Induce Apoptosis in Endothelial Cells Via Caspase 3 Activation Next, we tested whether the widespread cell death induced by diabetic plasma IgG auto-antibodies (FIG. 24a) was through apoptosis pathway. The endothelial cells treated with diabetic plasma IgG displayed condensed nuclear and fragmented DNA, a hallmark of apoptosis. Fifty percent apoptosis occurred in cells exposed (for 12 hours) to IgG fractions of plasma from diabetic maculopathy or progression in albuminuria subjects (FIG. 24c). In contrast, only 7.5% cells underwent apoptosis in cells exposed to normal human IgG fractions. Western blotting with antibodies specific for cleaved caspase 3 indicated the activation of caspase 3 in cells exposed to diabetic IgG auto-antibodies (FIG. 25a). A broad spectrum inhibitor of caspases, Q-VD-OPH(OPH), nearly completely blocked apoptosis in cells exposed to diabetic plasma IgG (FIG. 25b), suggesting the diabetic plasma IgG induced apoptosis through caspases-dependent pathway. The Rho kinase inhibitor Y27632 (10 uM) also partially inhibited endothelial cell apoptosis from one diabetic IgG fraction (n=3 experiments).

Physical and Chemical Properties of the Inhibitory Activity in Protein-A Eluates Nearly all of the inhibitory activity in plasma protein-A eluates from 3 of 4 diabetic subjects was retained after dialysis on a 30 kD MW cutoff membrane. Mass spectrometry of active inhibitory protein-A samples from 3 diabetic maculopathy plasmas demonstrated peaks at 150 kD, 112 kD, 77 kD, 56 kD and 23 kD (not illustrated). Strong heat (95 C×5 minutes) eliminated ~50% of the inhibitory endothelial cell activity in three of three diabetic, protein-A eluates tested. Exposure to a reducing agent, 6 mM dithiothreitol for 2 hours at 25 C, caused a loss of 3-50%, mean 23% of the inhibitory activity in the protein-A eluates from three diabetic maculopathy plasmas.

Discussion

This is the first demonstration that circulating auto-antibodies from type 2 diabetes with macular edema and/or progression from micro-albuminuria to overt nephropathy induce apoptosis in endothelial cells.

Anti-endothelial cell auto-antibodies are common in systemic auto-immune diseases such as lupus (17) or vasculitis (18). Our finding of inhibitory endothelial cell auto-antibodies in adult obese, type 2 diabetes is surprising, however, since type 2 diabetes is not an auto-immune disease. The prevalence of endothelial cell inhibitory auto-antibodies in patients with advanced type 2 diabetes from the Veterans Affairs Diabetes Trial (32%) (11) was similar to that reported in patients with type 1 diabetes of ten or more years average duration (19). This suggests that vascular damage per se may contribute to the development of IgG endothelial cell inhibitory auto-antibodies in advancing type 2 diabetes. Consistent with this possibility, the subset of VADT subjects with maculopathy were on average 5 years older and had a five years longer average duration of diabetes compared to the subjects with minimal retinopathy (Table 1).

The loss of heparan sulfate proteoglycan (HSPG) from (glomerular) endothelial cells has been proposed as an underlying mechanism in the development of diabetic micro-albuminuria (20) and in generalized diabetic vasculopathy (21). HSPG is a low affinity receptor for bFGF which is abundant on endothelial cells (22). HSPG is also a known target for auto-immunity (23). Auto-antibodies which bind to HSPG could account for the association between diabetic plasma inhibitory endothelial cell auto-antibodies and low plasma levels of the heparin-binding, basic fibroblast growth factor in patients with long-standing diabetes and maculopathy (e.g. Table 1) (11).

Basic FGF is an important survival factor in mesenchymal-derived cells (27) and photoreceptors (28). It is therefore surprising that, in our preliminary experiments, co-incubating endothelial cells with 100 pg/mL recombinant human bFGF did not rescue or prevent apoptosis induced by 4-30 ug/mL of the active inhibitory protein-A eluate fraction from 5 of 5 diabetic maculopathy plasmas.

In summary, our data provide evidence that macular edema in adults with advanced type 2 diabetes may be mediated in part by circulating auto-antibodies that potently induce apoptosis in endothelial cells. The baseline presence of auto-antibodies preceded the progression or development of retinal, renal, painful neuropathic or rarely, non-ischemic cardiovascular complications in affected diabetic patients suggesting that the auto-antibodies may have clinical utility as a marker for a broad range of serious or life-threatening complications in type 2 diabetes.

TABLE 1

Baseline characteristics in study subjects

| Variable | Maculopathy (n = 7) Mean SD | Minimal or no retinopathy (n = 7) Mean, SD | P value |
|---|---|---|---|
| Age (yrs) | 64 ± 5 | 59 ± 11 | 0.27 |
| Diab duration (yrs) | 13 ± 4 | 8 ± 6 | 0.11 |
| HbA1c (%) | 8.3 ± 1.4 | 9.7 ± 1.2 | 0.08 |
| ACR (mg/g) | 322 ± 381 | 45 ± 49 | 0.08 |
| bFGF (pg/mL) | 0 ± 0 | 0.7 ± 1.3 | 0.16 |
| Growth activity (%)* | 72 ± 20 | 101 ± 8 | 0.004 |

ACR—albumin/creatinine ratio;
HbA1c—hemoglobin A1c
*represents percent basal endothelial cell number after 48 hrs incubation with 30 ug/mL of the protein-A eluate fraction from plasma References in Example 12
1. Duhault J, Regnault F 1977 Diabetic microangiopathy: renal and retinal aspects. Paroi Arterielle 4:7-25
2. Ferris F L, 3rd, Patz A 1984 Macular edema. A complication of diabetic retinopathy. Surv Opthalmol 28 Suppl: 452-61
3. Deckert T, Feldt-Rasmussen B, Borch-Johnsen K, Jensen T, Kofoed-Enevoldsen A 1989 Albuminuria reflects widespread vascular damage. The Steno hypothesis. Diabetologia 32:219-26
4. Viberti G C 1983 Increased capillary permeability in diabetes mellitus and its relationship to microvascular angiopathy. Am J Med 75:81-4
5. Engerman R L, Kern T S 1986 Hyperglycemia as a cause of diabetic retinopathy. Metabolism 35:20-3
6. Anderson S, Brenner B M 1988 Pathogenesis of diabetic glomerulopathy: hemodynamic considerations. Diabetes Metab Rev 4:163-77
7. Aroca P R, Salvat M, Fernandez J, Mendez I 2004 Risk factors for diffuse and focal macular edema. J Diabetes Complications 18:211-5
8. Nguyen Q D, Tatlipinar S, Shah S M, et al. 2006 Vascular endothelial growth factor is a critical stimulus for diabetic macular edema. Am J Opthalmol 142:961-9
9. Esch F, Baird A, Ling N, et al. 1985 Primary structure of bovine pituitary basic fibroblast growth factor (FGF) and comparison with the amino-terminal sequence of bovine brain acidic FGF. Proc Natl Acad Sci USA 82:6507-11

10. Zimering M B, Eng J 1996 Increased basic fibroblast growth factor-like substance in plasma from a subset of middle-aged or elderly male diabetic patients with microalbuminuria or proteinuria. J Clin Endocrinol Metab 81:4446-52
11. Zimering M B, Anderson, R. J., Ge L., Moritz, T., Pardun, J. and the VADT Substudy Group 2008 Association between endothelial cell inhibitory autoantibodies and laser treatment for retinopathy in a baseline subset from the Veterans Affairs Diabetes Trial. Endocrine Society OR50-4:163
12. Zimering M B, Anderson, R. J., Luo, P., Pardun, J. and the VADT Substudy Group 2007 Inverse association between plasma basic fibroblast growth factor immunoreactivity and laser treatment for retinopathy in a baseline subset of adult type 2 diabetes from the Veterans Affairs Diabetes Trial. 89th Annual Meeting of the Endocrine Society P2:249
13. Zimering M B, Thakker-Varia S 2002 Increased fibroblast growth factor-like autoantibodies in serum from a subset of patients with cancer-associated hypercalcemia. Life Sci 71:2939-59
14. Pan Z, Damron D, Nieminen A L, Bhat M B, Ma J 2000 Depletion of intracellular Ca2+ by caffeine and ryanodine induces apoptosis of chinese hamster ovary cells transfected with ryanodine receptor. J Biol Chem 275:19978-84
15. Jones D B, Wallace R, Frier B M 1992 Vascular endothelial cell antibodies in diabetic patients. Association with diabetic retinopathy. Diabetes Care 15:552-5
16. van Paassen P, Duijvestijn A, Debrus-Palmans L, Damoiseaux J, Vroomen M, Tervaert J W 2007 Induction of endothelial cell apoptosis by IgG antibodies from SLE patients with nephropathy: a potential role for anti-endothelial cell antibodies. Ann N Y Acad Sci 1108:147-56
17. Song J, Park Y B, Lee W K, Lee K H, Lee S K 2000 Clinical associations of anti-endothelial cell antibodies in patients with systemic lupus erythematosus. Rheumatol Int 20:1-7
18. Belizna C, Duijvestijn A. Hamidou M, Cohen Tervaert J W 2006 Antiendothelial cell antibodies in vasculitis and connective tissue disease. Ann Rheum Dis 65:1545-50
19. Wangel A G, Kontiainen S, Scheinin T, Schlenzka A, Wangel D, Maenpaa J 1992 Anti-endothelial cell antibodies in insulin-dependent diabetes mellitus. Clin Exp Immunol 88:410-3
20. Reddi A S, Ramamurthi R, Miller M, Dhuper S, Lasker N 1991 Enalapril improves albuminuria by preventing glomerular loss of heparan sulfate in diabetic rats. Biochem Med Metab Biol 45:119-31
21. Jensen T 1997 Pathogenesis of diabetic vascular disease: evidence for the role of reduced heparan sulfate proteoglycan. Diabetes 46 Suppl 2:S98-100
22. Vlodavsky I, Miao H Q, Medalion B, Danagher P, Ron D 1996 Involvement of heparan sulfate and related molecules in sequestration and growth promoting activity of fibroblast growth factor. Cancer Metastasis Rev 15:177-86
23. Fillit H, Mulvihill M 1993 Association of autoimmunity to vascular heparan sulfate proteoglycan and vascular disease in the aged. Gerontology 39:177-82
24. Adamus G 2003 Autoantibody-induced apoptosis as a possible mechanism of autoimmune retinopathy. Autoimmun Rev 2:63-8
25. Reme C E, Grimm C, Hafezi F, Iseli H P, Wenzel A 2003 Why study rod cell death in retinal degenerations and how? Doc Opthalmol 106:25-9
26. van Nieuw Amerongen G P, Beckers C M, Achekar I D, Zeeman S, Musters R J, van Hinsbergh V W 2007 Involvement of Rho kinase in endothelial barrier maintenance. Arterioscler Thromb Vasc Biol 27:2332-9
27. Gospodarowicz D, Ferrara N, Schweigerer L, Neufeld G 1987 Structural characterization and biological functions of fibroblast growth factor. Endocr Rev 8:95-114
28. O'Driscoll C, Wallace D, Cotter T G 2007 bFGF promotes photoreceptor cell survival in vitro by PKA-mediated inactivation of glycogen synthase kinase 3 beta and CREB-dependent Bcl-2 up-regulation. J Neurochem 103:860-70
29. Vigny M, Ollier-Hartmann M P, Lavigne M, et al. 1988 Specific binding of basic fibroblast growth factor to basement membrane-like structures and to purified heparan sulfate proteoglycan of the EHS tumor. J Cell Physiol 137:321-8
30. Michel J B 2003 Anoikis in the cardiovascular system: known and unknown extracellular mediators. Arterioscler Thromb Vasc Biol 23:2146-54
31. Jeong J, Han I, Lim Y, et al. 2001 Rat embryo fibroblasts require both the cell-binding and the heparin-binding domains of fibronectin for survival. Biochem J 356:531-7
32. Sakata K, Kita M, Imanishi J, Onouchi Z, Liu Y, Mitsui Y 1995 Effect of Kawasaki disease on migration of human umbilical vein endothelial cells. Pediatr Res 38:501-5
33. Kato H, Ichinose E 1983 [Kawasaki disease: new and important problems in cardiology]. J Cardiogr 13:731-47
34. Zimering M B, Gurnani, L., Zimering, J., Pardun, J., Pan, Z. 2007 Pleiotrophic effects of diabetic plasma autoantibodies on rat differentiated pheochromocytoma PC-12 cells, endothelial cells and cardiomyocytes: associations with rho kinase, stress fiber activation, and increased intracellular calcium. Annual Meeting of the American Society for Cell Biology 2007
35. Kolavennu V, Zeng L, Peng H, Wang Y, Danesh F R 2008 Targeting of RhoA/ROCK signaling ameliorates progression of diabetic nephropathy independent of glucose control. Diabetes 57:714-23

What is claimed is:

1. A method for diagnosing an increased risk of pathological microvascular complications in diabetic patients having inhibitory endothelial cell antibodies comprising detecting plasma antibodies directed against heparan sulfate proteoglycan components of endothelial cells in a sample from the patient that inhibit endothelial cell growth and diagnosing an increased risk of pathological microvascular complications based on the presence of said plasma antibodies directed against heparan sulfate proteoglycan components.

2. The method of claim 1, comprising contacting the sample from the patient with an agent capable of forming a complex with the inhibitory endothelial cell antibodies in the sample.

3. The method of claim 1, wherein the sample is a biological fluid.

4. The method of claim 2, wherein the agent is selected from a group consisting of an antibody or portion thereof that binds to an Fc portion of an immunoglobulin; *Staphylococcus Aureus* Protein A; *Staphylococcus Aureus* Protein G; *Staphylococcus Aureus* Protein L; *Staphylococcus Aureus* Protein G/L; and Fc receptor.

5. The method of claim 4, wherein the antibody or portion thereof that binds to the Fc portion of an immunoglobulin is selected from a group consisting of an anti-IgE antibody; anti-IgG1 antibody; anti-IgG2 antibody; anti-IgG3 antibody; and anti-IgG4 antibody.

6. A method for monitoring the course of a pathological microvascular complication in a diabetic subject which comprises quantitatively determining in a first sample from the subject the presence of antibodies directed against heparan sulfate proteoglycan components of endothelial cells in a sample from the patient that inhibit endothelial cell growth, and comparing the amount so determined with the amount of said antibodies present in a second sample from the subject, such samples being taken at different points in time, an increase in the amount of said antibodies indicating progression of the pathological microvascular complication.

7. The method of claim 1 or 6, wherein the pathological microvascular complication is selected from the group comprising neuropathy, retinopathy, and macular edema.

8. A method for alleviating diabetic complications selected from a group consisting of macular edema and retinopathy in a subject comprising:
   a. determining whether a subject is at risk of pathological microvascular complications in diabetes by the method of claim 1; and
   b. administering insulin and/or fibrate drugs to the subject thereby alleviating said diabetic complications in the subject.

9. The method of claim 1 further comprising detecting levels of plasma bFGF in the sample.

10. The method of claim 8, wherein the fibrate drugs are selected from a group consisting of clofibrate, bezafibrate, aluminium clofibrate, gemfibrozil, fenofibrate, simfibrate, ronifibrate, ciprofibrate, etofibrate, clofibride, and clinofibrate.

11. The method of claim 1 further comprising determining the concentration of inhibitory endothelial cell antibodies so detected.

* * * * *